(12) United States Patent
Sivasankar et al.

(10) Patent No.: US 8,362,225 B2
(45) Date of Patent: Jan. 29, 2013

(54) COMPOSITIONS AND METHODS OF USE OF MITOGEN-ACTIVATED PROTEIN KINASE KINASE KINASE

(75) Inventors: Shoba Sivasankar, Urbandale, IA (US); Anna Lyznik, Johnston, IA (US); Kellie Reimann, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 319 days.

(21) Appl. No.: 12/481,652

(22) Filed: Jun. 10, 2009

(65) Prior Publication Data

US 2009/0307800 A1 Dec. 10, 2009

Related U.S. Application Data

(60) Provisional application No. 61/060,249, filed on Jun. 10, 2008.

(51) Int. Cl.
- *C12N 15/29* (2006.01)
- *C12N 15/82* (2006.01)
- *A01H 5/00* (2006.01)
- *A01H 5/10* (2006.01)
- *C07K 14/415* (2006.01)

(52) U.S. Cl. .............. 536/23.6; 435/252.3; 435/320.1; 435/419; 530/376; 800/298

(58) Field of Classification Search ........................ None
See application file for complete search history.

(56) References Cited

U.S. PATENT DOCUMENTS

| | | |
|---|---|---|
| 6,613,959 B1 * | 9/2003 | Sheen et al. ............... 800/278 |
| 2004/0034888 A1 | 2/2004 | Liu et al. |
| 2004/0123343 A1 | 6/2004 | LaRosa et al. |
| 2004/0214272 A1 | 10/2004 | LaRosa et al. |
| 2006/0075522 A1 | 4/2006 | Cleveland et al. |
| 2006/0141495 A1 | 6/2006 | Wu |
| 2007/0011783 A1 | 1/2007 | Liu et al. |
| 2007/0124833 A1 | 5/2007 | Abad et al. |
| 2007/0209085 A1 | 9/2007 | Wu et al. |

FOREIGN PATENT DOCUMENTS

| | | |
|---|---|---|
| WO | 0009724 A1 | 2/2000 |
| WO | 03008540 A2 | 1/2003 |

OTHER PUBLICATIONS

EMBL Accession No. AC191541; *Zea mays* 3 clone CH201-47604; ZMMBBc0476004; Sep. 21, 2006.*
Kovtun et al. Suppression of auxin signal transduction by a MAPK cascade in higher plants. Nature. Oct. 15, 1998;395(6703):716-20.*
Mishra et al. Signaling through MAP kinase networks in plants. Arch Biochem Biophys. Aug. 1, 2006;452(1):55-68. Epub May 24, 2006.*
Sandler S.J. et al. Inhibition of gene expression in transformed plants by antisense RNA. Plant Molecular Biology, 1988, vol. 11, No. 3, pp. 301-310.*
van der Krol A.R. et al. Inhibition of flower pigmentation by antisense CHS genes: promoter and minimal sequence requirements for the antisense effect. Plant Mol Biol. Apr. 1990;14(4):457-66.*
Waterhouse et al. Virus resistance and gene silencing: killing the messenger. Trends Plant Sci. Nov. 1999;4(11):452-457.*
Temple S.J. et al. Down-regulation of specific members of the glutamine synthetase gene family in alfalfa by antisense RNA technology. Plant Mol Biol. Jun. 1998;37(3):535-47.*
Carey A.T. at et al. Down-regulation of a ripening-related beta-galactosidase gene (TBG1) in transgenic tomato fruits. J Exp Bot. Apr. 2001;52(357):663-8.*
Wang H. et al. The emerging importance of cyclin-dependent kinase inhibitors in the regulation of the plant cell cycle and related processes, Canadian Journal of Botany, vol. 84, No. 4, Apr. 1, 2006 , pp. 640-650.*
EMBL Accession No. AC191541; *Zea mays* 3 clone CH2O1-47604; ZMMBBc0476004; Sep. 21, 2006.
GenBank Accession No. BT068193; *Zea mays* full-length cDNA clone ZM__BFb0092C16 ,RNA; Feb. 25, 2009.
EMBL Accession No. AC1845694; *Zea mays* chromosome 3 clone ZMMBBb-460H12; Apr. 6, 2006.

* cited by examiner

*Primary Examiner* — Cynthia Collins

(74) *Attorney, Agent, or Firm* — Pioneer Hi-Bred Int'l, Inc.

(57) ABSTRACT

Methods and compositions for modulating plant response, development and yield under varying environmental conditions are provided. Methods employing MAPKKK are provided. The MAPKKK sequences are used in a variety of methods including modulating root development, modulating leaf and/or shoot development, modulating tolerance under abiotic stress and modulating yield. Transformed plants, plant cell, tissues, seed and expression vectors are also provided.

9 Claims, 4 Drawing Sheets

Figure 2

```
ZmNPK1b              ------------------------------------------------------------
OsNPK1_NP_917084_    ------------------------------------------------------------
ZmNPK1d              ------------------------------------------------------------
ZmNPK1a              ------------------------------------------------------------
OsNPK1_NP_917080_    ------------------------------------------------------------
OsNPK1_BAF24980_     MRRDDAGGGGFGDLFDSVRRSIAFRTSTAPETP-GPLGGGGIGVRISSCLRKSRGMGLL
ANP1_O22040_         ----------MQDFFGSVRRSLVFRPSSDDDNQENQPPFPGVLADKITSCIRKSK-----

ZmNPK1b              ----------------------------------MTTTTTAKQLRRVRTLGRGASGAVVWLA
OsNPK1_NP_917084_    ---------------------------------------MAKQLRRVRTLGRGASGAVVWLA
ZmNPK1d              --------------------------------------MATAVSGRWTRVRTLGRGASGAVVSLA
ZmNPK1a              ---------------------------------------MAASGRWRRLRTLGRGASGAVVSLA
OsNPK1_NP_917080_    --------------------------------------MAIAVSGRWTRLRTLGRGASGAVVSLA
OsNPK1_BAF24980_     GLISKSPSPPRRLLPPAPEFSGGGGGGGRGGGGGEESPQIRWRKGELIGSGAFG-QVYLG
ANP1_O22040_         IFIKPSFSPP----PPANTVD--------------MAPPISWRKGQLIGRGAFG-TVYMG
                                                          :  :* ** *   * :.

ZmNPK1b              SDEASGELVAVKSARAAG----------AAAQLQREGRVLRGLSSPHIVPCLGSRAAAGG
OsNPK1_NP_917084_    SDDDSGELMAVKSASAGG----------AAAQLRREGRVLSGLCSPHIVPCLGSRAAAGG
ZmNPK1d              ADAASGALFAVKSAPAGTR---------AAENLRREGSILSALRSPHVVPCLGHRPAADG
ZmNPK1a              SDAASGELFAVKSAGASG----------AATLRREHAVLRGLRSPHVVRCVGGGEGADG
OsNPK1_NP_917080_    EDGASGELFAVKTAAAAE----------AAMLRRERGMMSGLSSPHVVPCIGGGDGPDG
OsNPK1_BAF24980_     MNLDTGELLAVKQVLIGSNNATREKAQAHIRELEEEVKLLKNLSHPNIVRYLG-TVREED
ANP1_O22040_         MNLDSGELLAVKQVLIAANFASKEKTQAHIQELEEEVKLLKNLSHPNIVRYLG-TVREDD
                      :  :* *.***.    .       .  *..*  ::  *  *::*  :*      .

ZmNPK1b              EYQLLLEFAPGGSLADEAARSGGGRLAER-AIGAYAGDVARGLAYLHGRSLVHGDVKARN
OsNPK1_NP_917084_    EYQLFLEFAPGGSLADEAARNGG-CLPEP-AIRAYAADVARGLAYLHGNSLVHGDVKARN
ZmNPK1d              GCQLLLEFAPGGSLADVAARSSGGRIGDERAVAAYAADVARGLAYLHGRSVVHGDVKARN
ZmNPK1a              SYQVFLEYAPGGSVADAVARGGG-ALEER-AIRALAADVLRGLAYLHGRSVVHGDVKARN
OsNPK1_NP_917080_    SYNLFLEFAPGGSLANEVARDGG-RLEER-AIRVYAADVLRGLTYLHGMSLVHGDVKADN
OsNPK1_BAF24980_     TLNILLEFVPGGSIQSLLGKLGS--FPEA-VIRKYTKQILQGLEYLHNNAIIHRDIKGAN
ANP1_O22040_         TLNILLEFVPGGSISSLLEKFGP--FPES-VVRTYTRQLLLGLEYLHNHAIMHRDIKGAN
                     :::**:.****:      .   .   :  .:   ::  ** ***. :::* *:*. *

ZmNPK1b              VVIGGDGRARLTDFGCARP-----AGGSTRPVGGTPAFMAPEVARGQEQGPAADVWALGC
OsNPK1_NP_917084_    VVIGSDGRARLTDFGCAR------VMDSAGPIGGTPAFMAPEVARGEEQGPAADVWALGC
ZmNPK1d              VVVGADGRAKLADFGCAR------AVGSGRPVGGTPAFMAPEVARGEEQGPAADVWALGC
ZmNPK1a              VLLGADGRARLADFGCARTP----GFSARRPLGGTPAFMAPEVARGEAQGPAADVWALGC
OsNPK1_NP_917080_    IVIGVDGLAKLADFGCAKT------MDSERPVSGTPAFMAPEVARGEEQGPAADVWALGC
OsNPK1_BAF24980_     ILVDNKGCIKLADFGASKQVAKLATITAAKTMKGTPHWMAPEVIVGSGHNFSADIWSVGC
ANP1_O22040_         ILVDNKGCIKLADFGASKQVAELATMTGAKSMKGTPYWMAPEVILQGHSFSADIWSVGC
                     :::. .*  :*:***.::              .  : *** :****    :. :**:*:**

ZmNPK1b              MVVELATGRAPWSDVE-GDDLLAALHRIGYTDDVPEVPAWLSPEAKDFLAGCFERRAAAR
OsNPK1_NP_917084_    TIIEMATGRAPWSDM---DDILAAVHRIGYTNAVPEVPGWLSAEAKDFLDGCFERNASDR
ZmNPK1d              TVVEMATGRAPWSDV---DSLPAAVHRIGYTDAVPDAPGWMSAEAKDFLARCFARNPRDR
ZmNPK1a              TVVEMATGRAPWGGADA--DVLAAVHRIGYTDAVPDAPSWMSAEARDFLARCFARDAAER
OsNPK1_NP_917080_    TVIEMATGRAPWSDMD---DVLAAVHRIGYTDAVPEVPVWLSAEAKDFLAMCFARNAGDR
OsNPK1_BAF24980_     TVIEMATGKPPWSQQY---QEVALLFHVGTTKSHPPIPEHLSPEAKDFLLKCLQKEPELR
ANP1_O22040_         TVIEMVTGKAPWSQQY---KEVAAIFFIGTTKSHPPIPDTLSSDAKDFLLKCLQEVPNLR
                     ::*:.**:.**.        .  *  :.  *  *   *  :*.:::*:***  *:  . . *
```

Figure 2 (continued)

```
ZmNPK1b           PTAAQLAAHPFVVASASA--------------------------------------AAAIR
OsNPK1_NP_917084_ STAAQLLEHPFVAS-AAA--------------------------------------LDRWP
ZmNPK1d           CTAAQLLEHPFLAS-------------------------------------------AGRG
ZmNPK1a           WTAAQLLEHPFVAA---P---------------------------------------CHG-H
OsNPK1_NP_917080_ STAAQLLEHPFVAF---A---------------------------------------CHEVK
OsNPK1_BAF24980_  STASDLLKHPFVTGESEN------------LQPLNCAAQQETCVNELPAHDVSSGLGLN
ANP1_O22040_      PTASELLKHPFVMGKHKESASTDLGSVLNNLSTPLPLQINNTKSTPDSTCDDVGDMCNFG
                  **::*  ***:

ZmNPK1b           GPAKQEVVPSPKSTLHDAFWDSDAEDE-ADEMSTGAAAERIGALACAASALPD-------
OsNPK1_NP_917084_ EPAKQERA-SPKSTLHDAFWDSDTDDE-DDEMPTG-AAERIGALACAASALPD-------
ZmNPK1d           VKAEEAAAASPTSTLDAAVWEPDSDDE-GDASESP--AQRIKALACPCSVLPD-------
ZmNPK1a           GDHEAPR-VSPKSTLDAAFWEAEDDDDDADEAVSASASERIKSLACSACALPD-------
OsNPK1_NP_917080_ AAQPKPRWVSPKSTLDAAFWESETDDEEEVDEITESLCDRIKSLACPVSALPD-------
OsNPK1_BAF24980_  HSVNWPTISSNRSSKIKPLWEG---SCDEDDMCEFADKDDCPAVGSSYNPMSEPFDNWES
ANP1_O22040_      -SLNYSLVDPVKSIQNKNLWQQNDNGGDEDDMCLIDDENFLTFDGEMSSTLEK-----DC
                     .  *         .*:            :          :      :   .

ZmNPK1b           -WDTEEG-WIDLQDDHSAGTADAPPAPVADYFISWAEPSDAELEPFVAVAAAAGLPHVAG
OsNPK1_NP_917084_ -WDSDEG-WIEVHDEVSF-AAVTPPASDADYFV-WAELSDPEMEQFA--VAADGVNHVPR
ZmNPK1d           -WDSEEGDWIEVLDEQCEATNLVP--------VPTKEAAGDDECQLPSVALETGVDFIDA
ZmNPK1a           -WDGEDG-WIEVLGDQ----QRVEVCG-----AVQVARSAPGKVSSVLAVPAGEMDVGGG
OsNPK1_NP_917080_ -WDSDEG-WIDLLGEQCEACDSEAARE-----SIDVARSAPSKVSSAATVPAAEVVLGGG
OsNPK1_BAF24980_  KFDASPEQTSHQSMEFG-GLAKHAESSMTENDFTFPCEGS--CEDDDVLTESKIKAFLDE
ANP1_O22040_      HLKKSCDDISDMSIALKSKFDESPGNGEKESTMSMECDQPSYSEDDDELTESKIKAFLDE
                    .  .   .

ZmNPK1b           VALAGATAVNLQGSYYY--YPPMHLGVRGNEIPRPLLDHHGDGLEKGQGSHRVCNRETEK
OsNPK1_NP_917084_ NEAEAIESSIRQGSYLHLMFPAIRIGVVSERQSIPF------------------------
ZmNPK1d           DAEGEDPGCCVAVGYDP----GCCVAVE--------------------------------
ZmNPK1a           GGGGGDELEAEDVSFGGEVPGSADASAERQKK----------------------------
OsNPK1_NP_917080_ GCCPSNEADAFDQSIGGDIQ-AADRSIERRNKVCAGSDND--------------------
OsNPK1_BAF24980_  KALDLKKLQTPLYEEFYN-TVNAGNSQVADHTSNGIFSNSP----KLPPRGKSPTSKMRG
ANP1_O22040_      KAADLKKLQTPLYEEFYNSLITFSPSCMESNLSNSKREDTARGFLKLPPKSRSPSRGPLG
                                     .

ZmNPK1b           VTMKRISLKRRAAFLLDQHHVRSLDKLEYRPRHDRMLRRRQSIYRSNSVLGYDVSKGRQV
OsNPK1_NP_917084_ ------------------------------------------------------------
ZmNPK1d           ------------------------------------------------------------
ZmNPK1a           ---------RYLIL---RSHYCHVLSCQLVPCNLPLVVVNNAIK-------------LWV
OsNPK1_NP_917080_ ---VLPFRLRLALLGPSRPSTAHIRKPPPNPRGRSALTASASISSPRRAC-VDVKRGVCV
OsNPK1_BAF24980_  GAAAASTCDNSNNTRPES-CSNQLSEDTVQSSRILREIASPQLDELGNKIHSDVQDSPSV
ANP1_O22040_      GSPSRATDATSCSKSPGSGGSRELNINNGGDEASQDGVSARVTDWRGLVVDTKQELSQCV

ZmNPK1b           RWRRAVCIAVAA------------------------------------------------
OsNPK1_NP_917084_ ------------------------------------------------------------
ZmNPK1d           ------------------------------------------------------------
ZmNPK1a           PTKKKKKK----------------------------------------------------
OsNPK1_NP_917080_ APRPHRLT----------------------------------------------------
OsNPK1_BAF24980_  SFAERQRKWKEELVQELERER-----------------GNDEIS----------------
ANP1_O22040_      ALSEIEKKWKEELDQELERKRQEIMRQAGLGSSPRDRGMSRQREKSRFASPGK
```

COMPOSITIONS AND METHODS OF USE OF MITOGEN-ACTIVATED PROTEIN KINASE KINASE KINASE

CROSS-REFERENCE

This utility application claims the benefit U.S. Provisional Application Ser. No. 61/060,249, filed Jun. 10, 2008 which is incorporated herein by reference.

FIELD OF THE INVENTION

The invention relates to the field of the genetic manipulation of plants, particularly the modulation of gene activity and development in plants.

BACKGROUND OF THE INVENTION

The mitogen-activated protein kinases (MAPKs) integrate multiple intracellular signals transmitted by various second messengers in a complex signal transduction mechanism. MAPKs phosphorylate and regulate the activity of a variety of enzymes and transcription factors. The activity of MAPKs is triggered by a series of cascades that result in the phosphorylation of the MAPK on both a threonine and tyrosine by a MAPK kinase (MAPKK). The MAPKK is activated by a MAPKKK that becomes active by phosphorylation on its serine/threonine.

The MAPK phosphorylation cascade is highly conserved in eukaryotes. Indeed, homologs in yeast, Drosophila, mammalian cells and plants have been identified. As of 2002, more than 60 MAPKKK genes have been identified in *Arabidopsis* alone. (Ichimura, et al., (2002) *Trends Plant Sci* 7:301-308). Because of the large number of proteins involved in the cascade, it is not apparent which proteins are essential, cause lethality if absent, or are functionally redundant.

MAPKKKs and their targets have been implicated in eukaryotic organisms' growth and development. For example, in plants, MAPKKK cascades have been associated with embryonic development, cell division, disease defense responses and abiotic stress responses (Tena, et al., (2001) *Curr Opin Plant Biol* 4:392-400.).

It has recently been discovered that loss of function mutations in a MAPKKK gene called YODA (YDA) produce *Arabidopsis* plant embryos lacking a suspensor, a tissue that functions to provide nutrients from the endosperm to the growing embryo. Not all yda plants developed into mature plants and those that did exhibited delayed root development and were smaller than wild-type plants. Known plant hormones were not able to rescue the yda phenotype, suggesting a novel developmental signaling pathway. (Lukowitz, et al., (2004) *Sci. STKE* 2004 tw21).

Several MAPKKKs in the Arabidopsis ANP family have been identified and implicated in regulating cell division. (Krysan, et al., (2002) *Plant Cell* 14:1109-1120). A MAPKKK has also been identified in *N. benthamiana* leaves and found to play a role in the hypersensitive response and resistance against *Pseudomonas syringae*. (Pozo, et al., (2004) *The EMBO Journal* 23:3072-3082). The same MAPKKK was found to regulate cell death in susceptible leaves undergoing *P. syringae* infection. (Pozo, et al., (2004) *The EMBO Journal* 23:3072-3082).

Transgenic tobacco lines expressing different levels of the constitutively active *Arabidopsis* ortholog of Tobacco NPK1 were found to grow more vigorously than did the wild type plants in the presence of elevated salt levels, cold temperatures and heat shock, but phenotypically did not differ from wild type plants under normal growth conditions (U.S. Pat. No. 6,613,959). The manipulation of this oxidative stress signaling regulator can protect plant cells from diverse environmental stresses, such as heat and high salt. See, U.S. Pat. No. 6,613,959 (Kovtun, et al., (2000) *Proc. Natl. Acad. Sci. USA* 97:2940-2945).

Thus, MAPKKKs are involved in a variety of aspects of plant growth and development. Given the important role of members of the MAPKKK signal transduction cascade, in particular the MAPKKK signal transduction molecules, in regulating plant cellular processes ranging from cellular proliferation and differentiation to cellular apoptosis, there exists a need for identifying plant MAPKKK polynucleotides and polypeptides as well as for modulators of such molecules for use in regulating a variety of responses and development. For these and other reasons, there is a need for the present invention.

BRIEF SUMMARY OF THE INVENTION

Generally, it is the object of the present invention to provide polynucleotides and polypeptides relating to MAPKKK. It is an object of the present invention to provide transgenic plants comprising the polynucleotides and polypeptides of the present invention. Additionally, it is an object of the present invention to provide methods of modulating, in a plant cell or in a transgenic plant, the expression of the polynucleotides and polypeptides of the present invention. Yet another object of the present invention is to provide methods of increasing abiotic stress resistance or tolerance in a plant.

Therefore, in one aspect, the present invention relates to an isolated MAPKKK polynucleotide that encodes the polypeptide of SEQ ID NO: 2, 5, 8 or 10; a polynucleotide having the sequence of SEQ ID NO: 1, 4, 7 or 9; a polynucleotide having at least 30 nucleotides in length which hybridizes under stringent conditions to any of the former polynucleotides. In another aspect, the present invention includes a polynucleotide having at least 60% sequence identity to SEQ ID NOS: 1, 4, 7 or 9. Also included are isolated polynucleotides amplified from a nucleic acid library using primers based on sequences of the present invention, for example, ZmNPK1b—Forward Primer and ZmNPK1b—Reverse Primer as set forth in SEQ ID NOS: 12 and 13 respectively. In one aspect, the nucleic acid library is a *Zea mays* (maize) library. In another aspect, the nucleic acid library is a cDNA library. Provided herein in another aspect of the invention are isolated polynucleotides degenerate as a result of the genetic code for any of the MAPKKKs of the present invention. In another aspect, an isolated polynucleotide is complementary to a polynucleotide of any one of the MAPKKKs of the present invention. In another aspect, the present invention relates to an isolated polynucleotide that encodes a MAPKKK polypeptide that confers resistance or tolerance to dehydration, salinity, temperature stress, environmental stress or a pathogen.

In yet another aspect, the present invention relates to a transgenic plant including a recombinant expression cassette comprising a plant promoter operably linked to any of the isolated polynucleotides of the present invention. The present invention also provides for transgenic seed from the transgenic plant. In another aspect, the present invention is directed to a host cell transfected with the recombinant expression cassette comprising a plant promoter operably linked to any of the isolated polynucleotides of the present invention. In one aspect, the host cell is a soybean, rice or maize cell.

In a further aspect, the present invention relates to an isolated polypeptide having an amino acid sequence having at least 70% sequence identity to the amino acid sequence set forth in SEQ ID NO: 2, 5, 8 or 10 and MAPKKK activity. In yet another aspect, the present invention relates to a transgenic plant comprising a recombinant expression cassette comprising a plant promoter operably linked to an isolated polynucleotide encoding a polypeptide that has an amino acid sequence that has at least 70% sequence identity to the amino acid sequence set forth in SEQ ID NO: 2, 5, 8 or 10 and has MAPKKK activity. The present invention also provides for transgenic seed from the transgenic plant. In another aspect, the present invention is directed to a host cell transfected with the recombinant expression cassette comprising a plant promoter operably linked to any of the isolated polynucleotides encoding polypeptides of the present invention.

In a further aspect, the present invention relates to a method of modulating the level of MAPKKK protein in a plant cell. In one aspect, the method includes transforming a plant cell with a MAPKKK polynucleotide operably linked to a promoter. The polynucleotide may be in sense or antisense orientation. The method further includes expressing the polynucleotide for an amount of time sufficient to modulate the MAPKKK protein in the plant cell.

In another aspect, the present invention provides a method of modulating the level of MAPKKK protein in a plant. The method includes stably transforming a plant cell with a MAPKKK polynucleotide, in sense or antisense orientation, operably linked to a promoter functional in a plant cell. The method includes regenerating the transformed plant cell into a transformed plant that expresses the MAPKKK polynucleotide in an amount sufficient to modulate the level of MAPKKK protein in the plant.

In another aspect, the present invention relates to a method of increasing abiotic stress resistance or tolerance in a plant. In one aspect, the method includes introducing into plant cells a construct comprising a polynucleotide encoding a MAPKKK of the present invention. The polynucleotide may be operably linked to a promoter functional in plant cells to yield transformed plant cells. The transformed plant cells are regenerated into a transgenic plant. The MAPKKK is expressed in at least some of the cells of the transgenic plant at levels sufficient to induce abiotic stress resistance or tolerance. In one aspect, the abiotic stress is drought, cold temperatures, salt, osmotic stress, frost or freeze, high temperatures, oxidative stress or chemical stress. The method may provide tolerance to other environmental stresses, such as UV-B, ozone, photooxidation, herbicide, pathogen or other stresses that also involve oxidative stress damage and the like.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE FIGURES

The invention can be more fully understood from the following detailed description and the accompanying figures and Sequence Listing which form a part of this application.

FIG. 2. CLUSTAL X (1.83) multiple sequence alignment of MAPKKKs. ZmNPK1a (SEQ ID NO: 2), ZmNPK1b (SEQ ID NO: 5) and ZmNPK1d (SEQ ID NO: 10) were aligned against the rice sequences, OsNPK1-like proteins, NP_917084 (SEQ ID NO: 14) NP_917080 (SEQ ID NO: 15) and BAF24980 (SEQ ID NO: 16), as well as the Arabidopsis ANP1 sequence, O22040 (SEQ ID NO: 17). The partial protein, ZmNPK1c (SEQ ID NO: 8), was excluded from this alignment. Perfectly conserved residues, which are primarily located at the N-terminal half of the protein, are marked by an asterisk.

BRIEF DESCRIPTION OF THE SEQUENCES

Figure 1:
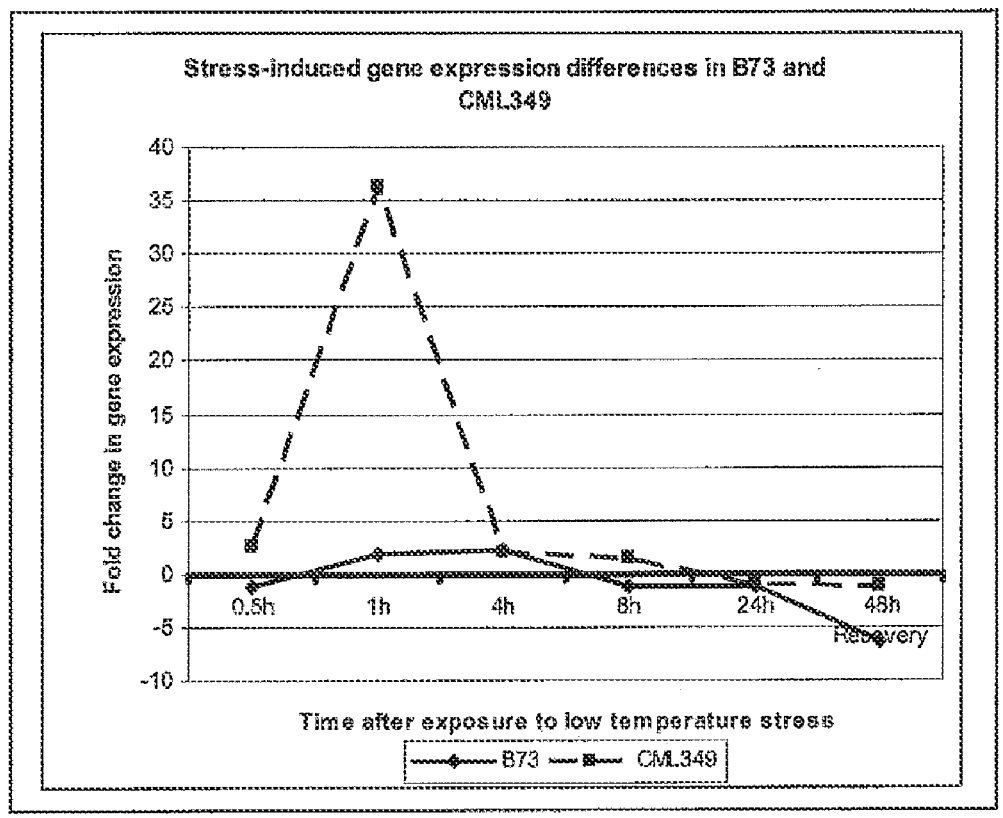
FIG. 1. Differences in stress-induced gene expression of ZmNPK1b between B73 and CML349 under cold stress.
Figure 3:
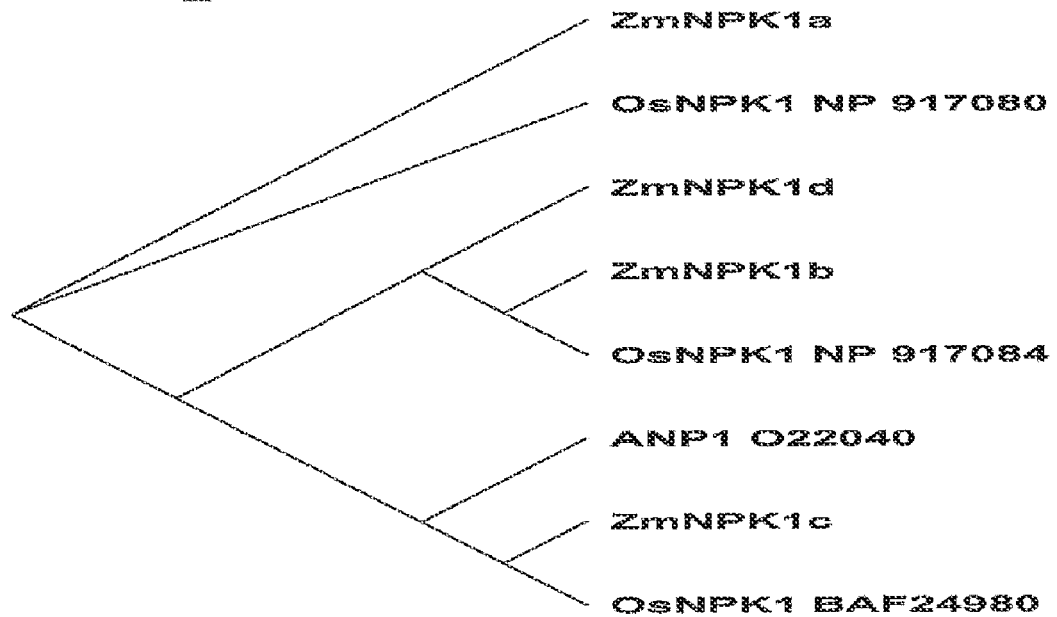
FIG. 3. The phylogenetic tree constructed from the maize, rice and *Arabidopsis* NPK1-like sequences on the basis of their amino acid sequences. The dendrogram was constructed using the multiple alignment tool, CLUSTAL.

The application provides details of MAPKKK sequences as shown in Table 1 below.

TABLE 1

| SEQ ID NO: | pnt or ppt | Length | Identification |
|---|---|---|---|
| 1 | pnt | 1396 | ZmNPK1a complete CDS represented by PCO644860 |
| 2 | ppt | 441 | Zm NPK1a protein sequence |
| 3 | pnt | 6053 | ZmNPK1a genomic sequence predicted by Pioneer proprietary gene modeling algorithms |
| 4 | pnt | 1864 | ZmNPK1b complete CDS represented by PCO644861 |
| 5 | ppt | 514 | ZmNPK1b complete protein sequence |
| 6 | pnt | 4019 | ZmNPK1b genomic sequence from BAC clone p1.bacb.pk191.e03 |
| 7 | pnt | 1662 | ZmNPK1c partial CDS represented by PCO622918 |
| 8 | ppt | 366 | ZmNPK1c partial protein sequence |
| 9 | pnt | 1375 | ZmNPK1d complete CDS represented by PCO638212 |
| 10 | ppt | 392 | ZmNPK1d complete protein sequence |
| 11 | pnt | 2923 | ZmNPK1d genomic sequence predicted by Pioneer proprietary gene modeling algorithms |
| 12 | pnt | 21 | ZmNPK1b - Forward Primer |
| 13 | pnt | 22 | ZmNPK1b - Reverse Primer |
| 14 | ppt | 404 | OsNPK1-like NP_917084 |
| 15 | ppt | 474 | OsNPK1-like NP_917080 |
| 16 | ppt | 653 | OsNPK1-like BAF24980 |
| 17 | ppt | 666 | *Arabidopsis* ANP1 O22040 |
| 18 | pnt | 615 | Zm rab17 promoter |
| 19 | pnt | 1625 | *Arabidopsis* rd29a promoter |
| 20 | pnt | 811 | eep5 promoter |

DETAILED DESCRIPTION OF THE INVENTION

The present invention now will be described more fully hereinafter with reference to the accompanying examples, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the invention set forth herein will come to mind to one skilled in the art to which this invention pertains, having the benefit of the teachings presented in the descriptions and the drawings herein. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The articles "a" and "an" are used herein to refer to one or more than one (i.e., to at least one) of the grammatical object of the article. By way of example, "an element" means one or more than one element.

Overview

The present invention provides novel compositions and methods for modulating, for example, increasing or decreasing, the level of MAPKKK protein in a plant cell or plant. In particular, the polynucleotides and polypeptides of the present invention can be used to generate transgenic plants expressing MAPKKKs of the present invention.

The present inventors have discovered four novel MAP-KKKs, one of which (ZmNPK1b) was found to be expressed at high levels in CML349, a tropical highland line known to be cold tolerant, relative to expression levels in B73, a corn-belt dent inbred relatively less tolerant to cold. Modulation of the MAPKKKs of the present invention would provide a mechanism for manipulating a plant's response to abiotic stresses, including but not limited to drought, cold temperatures, salt, osmotic stress, frost or freeze, high temperatures, oxidative stress and chemical stress as well as stress caused by other environmental factors, such as UV-B, ozone, photo-oxidation, herbicide, pathogen or other stresses that also involve oxidative stress damage. Thus, the present invention provides methods for modulating, for example, increasing or decreasing, a plant's resistance or tolerance to stresses, particularly abiotic stresses, using MAPKKK polynucleotides and polypeptides of the present invention.

Compositions

Compositions include plants having altered levels and/or activities of mitogen-activated protein kinase kinase kinase (MAPKKK). As used herein, the term mitogen-activated protein kinase kinase kinase (MAPKKK) includes but is not limited to the sequences disclosed herein, such as MAPKKK, their conservatively modified variants, regardless of source and any other variants which retain the biological properties of the MAPKKK, for example, MAPKKK activity as disclosed herein.

In specific compositions, the plants have an altered level and/or activity of a MAPKKK polypeptide having the amino acid sequence set forth in SEQ ID NO: 2, 5, 8 or 10 or an active variant or fragment thereof. Further provided are plants having an altered level and/or activity of the MAPKKK polypeptides encoded by a polynucleotide set forth in SEQ ID NO: 1, 4, 7 or 9 or an active variant or fragment thereof. The plants of the invention may exhibit modulation in stress tolerance, seed set, plant yield, plant vigor, shoot growth, leaf senescence, shoot regeneration or root growth.

In specific embodiments, the plants of the invention have stably incorporated into their genomes a MAPKKK sequence. In further embodiments, the MAPKKK sequence is operably linked to a tissue-preferred promoter active in the plant.

Other embodiments provide plants which have been genetically modified at a native genomic locus encoding a MAPKKK polypeptide. By "native genomic locus" is intended a naturally occurring genomic sequence. In some embodiments, the native genomic locus is set forth in SEQ ID NOS: 3, 6 and 11 respectively for ZmNPK1a, ZmNPK1b and ZmNPK1d. Genomic sequences for ZmNPK1a and ZmNPK1d are provided using Pioneer proprietary gene modeling algorithms. The gene modeling algorithm reconciles both public and proprietary information on maize sequences to generate gene structure and as new maize sequence information becomes available the gene structures may be revised. Genomic sequence information for ZmNPK1b, is provided using the information from the sequenced BAC clone, p1.bacb.pk191.e03.

Genetic modification encompasses either introduction of a MAPKKK sequence or modification of a native genomic locus encoding a MAPKKK or both and may result in phenotypic change. By "phenotypic change" is intended a measurable change in one or more cell functions. For example, plants having genetic modification at a genomic locus encoding a MAPKKK polypeptide may show reduced or eliminated expression or activity of the MAPKKK polypeptide. Certain phenotypic changes may be observed at the tissue or whole-plant level, for example modified root development or enhanced seedling growth. Various methods of genetic modification are described in more detail elsewhere herein, as are examples of phenotypes that can result from modification affecting the level and/or activity of a MAPKKK sequence of the invention.

Phenotypic changes may include but are not limited to a modulation in root development, stress tolerance, shoot development, leaf development, leaf senescence, photosynthesis, callus regeneration, seed set, plant yield or plant vigor.

Modified plants are of interest, as are modified plant cells, plant protoplasts, plant cell tissue cultures from which a plant can be regenerated, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, "grain" means the mature seed produced by commercial growers for purposes other than advancing or reproducing the species, e.g. for such end uses as feed, food, or fiber. Progeny, variants and mutants of the regenerated plants are also included within the scope of the invention, provided that such plants or plant parts comprise the genetic modification.

The MAPKKK polypeptides employed in the invention share sequence identity with members of the MAPKKK family of proteins. Changes in MAPKKK activity alter the intracellular signaling process involving Mitogen Activated Protein kinase kinase kinase (MAPKKK) cascades. These include the cascades of MAPK kinase kinase (MAP3K, also called MAPKKK or MEKK), MAPK kinase (MAP2K, also called MKK or MEK) and MAPK or extracellular signal-regulated kinase (ERK). MAPKKK/MEKK phosphorylates and activates its downstream protein kinase, MAPKK/MEK, which in turn activates MAPK.

As described herein, the inventors have identified four novel MAPKKK cDNAs in maize that are homologs to rice NPK1. The maize MAPKKKs polynucleotides of this invention are 1396 (ZmNPK1a), 1864 (ZmNPK1b), 1662 (ZmNPK1c) and 1375 (ZmNPK1d) nucleotides in length encoding polypeptides with calculated molecular weight of 46 KDa (ZmNPK1a), 54 KDa (ZmNPK1b), 41 KDa (partial ZmNPK1c) and 40 KDa (ZmNPK1d). The polypeptides ZmNPK1a, ZmNPK1b and ZmNPK1d share approximately 53% amino acid consensus between ZmNPK1a and ZmNPK1b, 65% between ZmNPK1a and ZmNPK1d, 61% between ZmNPK1b and ZmNPK1d using GAP (BLOSUM 62). The maize cDNAs for Zm NPK1a, ZmNPK1b and ZmNPK1d encode polypeptides with approximately 58%, 73%, 63% overall amino acid identity respectively to the rice NPK1-like gene (dbj|BAB64165.1| (AP003254) NPK1-related protein kinase-like protein [*Oryza sativa*]. The maize MAPKKKs were checked for possible chromosomal position by BLAST search against public and proprietary BAC sequences. Three of the maize MAPKKKS, ZmNPK1a, ZmNPK1b and ZmNPK1d, mapped to chromosome 3, while the fourth, namely, ZmNPK1c (PCO622918) localized to chromosome 2. Potential association with any known QTLs for drought stress was checked using a Pioneer proprietary association tool. Thus, ZmNPK1a and ZmNPK1d were observed to be potentially associated with a QTL related to the Staygreen phenotype (Thomas and Howarth, (2000) *J Exp Bot* 51 Spec No: 329-337) and ZmNPK1c was observed to be potentially associated with yield QTLs and also with the drought QTLs for Anthesis Silking Interval, Staygreen and Barrencount. These potential associations with QTLs predicted by this proprietary association tool does not prove that these specific genes are controlling these traits, rather it merely hints at which trait associations exist. To further characterize the MAPKKKs, the expression of all four MAPKKK sequences were analyzed in Lynx Massively Parallel Signature Sequencing (MPSS) libraries (Table 4). Brenner, et al., (2000) *Nat Biotechnol.* 18:630-634). The expression of ZmNPK1a was found to be high in stalk, root and pulvinus tissue of B73 stalks. Expression of ZmNPK1b was found to be high in kernel and root tissue, maize kernels at 0 days after pollination, and in maize primary roots. Expression of the ZmNPK1c was not detected in specific tissues most likely to very little representation in the Lynx libraries. Finally, the expression of ZmNPK1d was uniformly distributed in all tissues, the highest level in maize kernels at 0 days after pollination. As shown herein in Example 10, ZmNPK1b and ZmNPK1d were also found to be specifically induced by drought stress and treatment with the stress-hormones, ABA and ethylene as described herein.

Without wishing to be bound by this theory, the present inventors believe that MAPKKKs of the present invention will be useful for increasing stress resistance or tolerance to a number of abiotic stresses. As used herein, the term "abiotic stress" includes but is not limited to drought, cold temperatures, salt, osmotic stress, frost or freeze, high heat temperatures, oxidative stress and chemical stress as well as stress by other environmental stresses, such as UV-B, ozone, photooxidation, herbicide, pathogen, or other stresses that also involve oxidative stress damage (Green and Fluhr, (1995) *Plant Cell* 7:203-212; Prasad, (1996) *Plant J.* 10:1017-1026; Willekens, et al., (1997) *EMBO J.* 16:4806-4816; Chamnongpol, et al., (1998) *Proc. Natl. Acad. Sci USA* 95:5818-5823; Schraudner, et al., (1998) *Plant J.* 16:235-245; Karpinski, et al., (1999) *Science* 284:654-657).

Resistance or tolerance to one or more abiotic stresses may be achieved directly through activation of targets of the MAPKKKs or indirectly through MAPKKK signal transduction cascades, including downstream targets of the MAPKKKs of the present invention. Thus, modulation of MAPKKK activity of the MAPKKKs of the present invention in a plant cell provides a novel strategy for cross protection from one or more abiotic stresses in plants.

Also contemplated is the activation or expression of genes that lie upstream of the ZmNPK MAPKKKs in the regulatory cascade so that activation of a MAPKKK target is achieved. Targets or substrates of the MAPKKKs include but are not limited to transcription factors, other protein kinases and cytoskeleton-associated proteins. Targets or substrates may be identified using techniques common to one skilled in the art including in gel kinase assays, yeast-two hybrid assays, protoplast transient expression assays using stress-responsive promoters linked to a reporter gene, for example, a promoter that is activated during oxidative stress, heat, cold or drought and the like. (Kovtun, et al., (2000). *Proc. Natl. Acad. Sci. USA* 97:2940-2945; Machida, et al., (1997) *Critic. Rev. Plant Sci.* 16:481-496; Mazoguchi, et al., (1997) *Trends Biotechnol.* 15:15-19; Zhang and Klessig, (1997) *Plant Cell* 9:809-824; Jonak, et al., (1999) *Cell. Mol. Life. Sci.* 55:204-231).

Compounds that modulate the activity of MAPKKKs of the present invention may be determined by assessing the interaction between a transcription factor and a regulatory element in a MAPKKK promoter, for example, a hormone- or stress-responsive regulatory element. For example, within the promoter sequence of the ZmNPK1b, there is at least one Abscissic Acid—Responsive Element (ABRE), specifically the ABREAT consensus, YACGTGGC and also the C-repeat/Dehydration Response Element (CRT/DRE) consensus, CCGAC. Assays are known in the art that detect the interaction of a DNA binding protein with a target DNA sequence (e.g., electrophoretic mobility shift assays, DNAse I footprinting assays and the like). By performing such assays in the presence and absence of test compounds, for example, auxin or hydrogen peroxide, these assays can be used to identify compounds that modulate (e.g., inhibit or enhance) the interaction of the DNA binding protein with its target DNA sequence.

As used herein, "wherein the stress resistance or tolerance of a plant is increased relative to the stress resistance or tolerance of a control plant that is non-transgenic for a MAPKKK of the present invention", refers to an increase in plant growth and/or yield and/or improved resistance to stress compared to the control plant. For example, stress resistance or tolerance of a plant to a particular abiotic stress, for example, salinity, may be assessed by comparing physical features and characteristics of plant growth, such as, plant height and weight, leaf area, plant water relations, ability to flower, ability to generate seeds, yield/productivity and sugar content of transgenic plants and non-transgenic control plants. (Shou, et al., (2004) *J Exp Bot.* 55(399):1013-9). In another aspect, physical features and characteristics of plant growth of the transgenic MAPKKK plant observed under abiotic stress may also be compared to the physical features and characteristics of a transgenic MAPKKK plant or a control plant non-transgenic for MAPKKKs of the invention that are not exposed to the abiotic stress so that "normal" plant growth and characteristics may be further evaluated.

By "increasing stress resistance or tolerance" is meant mediating a level of endurance, adaptability, or durability to a stress (e.g., a man-made stress, such as pollution or an environmental stress, such as drought, salinity and oxidative and temperature stresses) in a transgenic plant which is greater than that exhibited by a control plant (for example, a non-transgenic plant). Preferably, the level of stress resistance or tolerance in a transgenic plant (or transformed plant cell, plant component, plant tissue, or plant organ) of the invention is at least 5%, 10% or 20% (and preferably 30% or 40%) greater than the tolerance to a stress exhibited in a non-transgenic control plant (or control plant cell, plant component, plant tissue or plant organ). In other preferred embodiments, the level of stress resistance or tolerance to a stress is 50% greater, 60% greater and more preferably even 75% or 90% greater than a control plant, with up to 100% above the level of tolerance as compared to a control plant being most preferred. The level of stress resistance or tolerance is measured by conventional methods used to determine plant growth and response to stress. For example, the level of stress tolerance to salinity may be determined by comparing physical features and characteristics (for example, plant height and weight, leaf area, plant water relations, ability to flower, ability to generate seeds and yield/productivity) of transgenic plants and non-transgenic control plants.

Fragments and variants of the MAPKKK polynucleotides and proteins encoded thereby can be employed in the present invention. By "fragment" is intended a portion of the polynucleotide or a portion of the amino acid sequence and hence of the protein encoded thereby. Fragments of a polynucleotide may encode protein fragments that retain the biological activity of the native protein and hence retain MAPKKK activity, for example, a constitutively active MAPKKK created by deletion of its putative regulatory domains.

As used interchangeably herein, a "MAPKKK activity", "biological activity of MAPKKK" or "functional activity of MAPKKK", refers to an activity exerted by a MAPKKK protein, polypeptide or portion thereof as determined in vivo or in vitro, according to standard techniques. In one embodiment, a MAPKKK activity is a direct activity, such as an association with a MAPKKK-target molecule. As used herein, a "target molecule" is a molecule with which a MAPKKK protein binds or interacts in nature, such that MAPKKK-mediated function is achieved. A MAPKKK target molecule can be a non-MAPKK molecule or a MAPKKK protein or polypeptide of the present invention or a MAPKK protein or polypeptide. In an exemplary embodiment, a MAPKKK target molecule is a MAPKKK substrate (including, for example, but not limited to ZmMPK4 (MAP kinase 4, Genbank Accession Number BAA74733) or ZmMPK5 (MAP kinase 5, Genbank Accession Number BAA74734.1). In a preferred embodiment, a MAPKKK activity is at least one or more of the following activities: (i) interaction of a MAPKKK protein with soluble MAPKKK ligand (e.g., but not limited to ZmMPK4 or ZmMPK5 and the like); (ii) modulation of the activity of a MAPKKK substrate; (iii) activation of a MAPKKK substrate; (iv) indirect modulation of a downstream signaling molecule (e.g., MAPKK.) In yet another preferred embodiment, a MAPKKK activity is at least one or more of the following activities: (1) modulation of cellular signal transduction, either in vitro or in vivo; (2) regulation of gene transcription in a cell expressing a MAPKKK protein; (3) regulation of gene transcription in a cell expressing a MAPKKK protein, wherein said cell is involved in abiotic stress resistance or tolerance; (4) regulation of cellular proliferation; (5) regulation of cellular differentiation; (6) regulation of development and (7) regulation of cell death.

Alternatively, fragments of a polynucleotide that are useful as hybridization probes or PCR primers generally do not encode fragment proteins retaining biological activity. Thus, fragments of a nucleotide sequence may range from at least about 20 nucleotides, about 50 nucleotides, about 100 nucleotides, up to the full-length polynucleotide encoding the proteins employed in the invention.

A fragment of a MAPKKK polynucleotide that encodes a biologically active portion of a MAPKKK protein employed in the invention will encode at least 15, 25, 30, 50, 75, 100, 125, 150, 175, 200, 220 or 225 contiguous amino acids, or up to the total number of amino acids present in a full-length or partial MAPKKK protein of the invention (for example, 441, 514, 366 or 392 amino acids for SEQ ID NOS: 2, 5, 8 and 10, respectively).

A biologically active portion of a MAPKKK protein can be prepared by isolating a portion of one of the MAPKKK polynucleotides employed in the invention, expressing the encoded portion of the MAPKKK protein (e.g., by recombinant expression in vitro), and assessing the activity of the encoded portion of the MAPKKK protein. Polynucleotides that are fragments of a MAPKKK nucleotide sequence comprise at least 16, 20, 50, 75, 100, 150, 200, 250, 300, 350, 500, 550, 500, 550, 600, 650, 700, 800, 900, 1,000, 1,100 nucleotides or up to the number of nucleotides present in a full-length MAPKKK polynucleotide disclosed herein (for example, 1396, 1864, 1662 and 1375 nucleotides for SEQ ID NOS: 1, 4, 7 and 9 respectively).

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the MAPKKK polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a MAPKKK protein employed in the invention. Generally, variants of a particular polynucleotide of the invention will have at least about 50%, 55%, 50%, 55%, 60%, 65%, 70%, 75%, 80%, 85%, 90%, 91%, 92%, 93%, 95%, 95%, 96%, 97%, 98%, 99% or more sequence identity to that particular polynucleotide as determined by sequence alignment programs and parameters described elsewhere herein.

Variants of a particular polynucleotide employed in the invention (i.e., the reference polynucleotide) can also be evaluated by comparison of the sequence identity between the polypeptide encoded by a variant polynucleotide and the polypeptide encoded by the reference polynucleotide. Thus, for example, an isolated polynucleotide that encodes a polypeptide with a given percent sequence identity to any one of the polypeptides of SEQ ID NO: 2, 5, 8 or 10 is encompassed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 50%, 55%, 50%, 55%, 60%, 65%, 70%, 75%, 80%, 85%, 90%, 91%, 92%, 93%, 95%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they continue to possess the desired biological activity of the native protein, that is, MAPKKK activity as described herein. Such variants may result from, for example, genetic polymorphism or from human manipulation. Biologically active variants of a native MAPKKK protein of the invention will have at least about 50%, 55%, 60%, 65%, 70%, 75%, 80%, 85%, 90%, 91%, 92%, 93%, 95%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 5, 3, 2 or even 1 amino acid residue.

The proteins employed in the methods of the invention may be altered in various ways including amino acid substitutions, deletions, truncations, and insertions. Methods for such manipulations are generally known in the art. For example, amino acid sequence variants and fragments of the MAPKKK proteins can be prepared by mutations in the DNA. Methods for mutagenesis and polynucleotide alterations are well known in the art. See, for example, Kunkel, (1985) *Proc. Natl. Acad. Sci. USA* 82:588-592; Kunkel, et al., (1987) *Methods in Enzymol.* 155:367-382; U.S. Pat. No. 5,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal. Variants of MAPKKK polypeptides can also include isolating natural variants from plants cells that exist in nature or creating recombinant MAPKKKs.

Thus, the genes and polynucleotides employed in the invention include both the naturally-occurring sequences as well as mutant forms. Likewise, the proteins employed in the invention encompass naturally occurring proteins as well as variations and modified forms thereof. Such variants will continue to possess the desired MAPKKK activity. Obviously, the mutations that will be made in the DNA encoding the variant must not place the sequence out of reading frame and optimally will not create complementary regions that could produce secondary mRNA structure.

The deletions, insertions and substitutions of the protein sequences encompassed herein are not expected to produce radical changes in the characteristics of the protein. However, when it is difficult to predict the exact effect of the substitution, deletion or insertion in advance of doing so, one skilled in the art will appreciate that the effect will be evaluated by routine screening assays. That is, the activity and/or expression can be evaluated by in gel kinase assays, real time RT-PCR analysis, Northern, Westerns, electrophoretic mobility shift assays, DNAse I footprinting assays and the like. (Shou, et al., (2004) *J Exp Bot.* 55(399):1013-9). Assays for detecting such activity or expression are known to one skilled in the art. Alternately, they are described in detail elsewhere herein. For example, an oligonucleotide of at least 15, 30, 50, 100, 200, 300, 400, 500, 600, 700, 800, 900 or 1000 nucleotides in length and sufficient to specifically hybridize under stringent conditions to MAPKKK mRNA may be used in Northern blot analysis. MAPKKK proteins may be detected using a labeled antibody capable of binding to MAPKKKs proteins of the present invention. Antibodies can be polyclonal, or more preferably, monoclonal. An isolated MAPKKK protein, or fragment thereof, can be used as an immunogen to generate antibodies that bind specifically to MAPKKKs of the present invention using standard techniques for polyclonal and monoclonal antibody preparation. Techniques for detection of MAPKKK protein include enzyme linked immunosorbent assays (ELISAs), Western blots, immunoprecipitations and immunofluorescence.

Variant polynucleotides and proteins also encompass sequences and proteins derived from a mutagenic and recombinogenic procedure such as DNA shuffling. With such a procedure, one or more different MAPKKK coding sequences can be manipulated to create a new MAPKKK possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the MAPKKK gene of the invention and other known MAPKKK genes to obtain a new gene coding for a protein with an improved property of interest, such as an increased $K_m$ in the case of an enzyme. Strategies for such DNA shuffling are known in the art. See, for example, Stemmer, (1995) *Proc. Natl. Acad. Sci. USA* 91:10757-10751; Stemmer, (1995) *Nature* 370:389-391; Crameri, et al., (1997) *Nature Biotech.* 15:536-538; Moore, et al., (1997) *J. Mol. Biol.* 272:336-357; Zhang, et al., (1997) *Proc. Natl. Acad. Sci. USA* 95:5505-5509; Crameri, et al., (1998) *Nature* 391:288-291 and U.S. Pat. Nos. 5,605,793 and 5,837,558.

The polynucleotides employed in the invention can be used to isolate corresponding sequences from other organisms, particularly other plants, more particularly other monocots. In this manner, methods such as PCR, hybridization and the like can be used to identify such sequences based on their sequence homology to the sequences set forth herein. Sequences isolated based on their sequence identity to the entire MAPKKK sequences set forth in SEQ ID NO: 1, 4, 7 or 9 or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 95%, 95%, 96%, 97%, 98%, 99% or greater sequence identity. Functions of orthologs are often highly conserved among species. Thus, isolated polynucleotides that encode a MAPKKK protein and which hybridize under stringent conditions to the sequence of SEQ ID NO: 1, 4, 7 or 9 or to complements, variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York) and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments or other oligonucleotides, and may be labeled with a detectable group such as $^{32}P$ or another detectable marker. Thus, for example, probes for hybridization can be made by labeling synthetic oligonucleotides based on the MAPKKK polynucleotides of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, the entire MAPKKK polynucleotide disclosed herein, or one or more portions thereof, may be used as a probe capable of specifically hybridizing to corresponding MAPKKK polynucleotide and messenger RNAs. To achieve specific hybridization under a variety of conditions, such probes include sequences that are unique among MAPKKK polynucleotide sequences and are optimally at least about 10 nucleotides in length, and most optimally at least about 20 nucleotides in length. Such probes may be used to amplify corresponding MAPKKK polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 50 to 55% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 25 hours, usually about 5 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl, (1985) *Anal. Biochem.* 138:267-285: $T_m$=81.5° C.+16.6 (log M)+0.51 (% GC)−0.61 (% form)−500/L; where M is the molarity of monovalent cations, % GC is the percentage of guanosine and cytosine nucleotides in the DNA, % form is the percentage of formamide in the hybridization solution and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 5° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 15, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 55° C. (aqueous solution) or 32° C. (formamide solution), it is optimal to increase the SSC concentration so that a higher temperature can be used. An extensive guide to the hybridization of nucleic acids is found in Tijssen, (1993) *Laboratory Techniques in Biochemistry and Molecular Biology—Hybridization with Nucleic Acid Probes*, Part I, Chapter 2 (Elsevier, New York) and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 5:11-17; the local alignment algorithm of Smith, et al., (1981) *Adv. Appl. Math.* 2:582; the global alignment algorithm of Needleman and Wunsch, (1970) *J. Mol. Biol.* 58:553-553; the search-for-local alignment method of Pearson and Lipman, (1988) *Proc.*

*Natl. Acad. Sci.* 85:2555-2558; the algorithm of Karlin and Altschul, (1990) *Proc. Natl. Acad. Sci. USA* 872265, modified as in Karlin and Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA Accelrys® GCG® (Accelrys Inc., 9685 Scranton Road, San Diego, Calif., USA). Alignments using these programs can be performed using the default parameters. The CLUSTAL program is well described by Higgins, et al., (1988) *Gene* 73:237-255 (1988); Higgins, et al., (1989) CABIOS 5:151-153; Corpet, et al., (1988) *Nucleic Acids Res.* 16:10881-90; Huang, et al., (1992) *CABIOS* 8:155-65 and Pearson, et al., (1995) *Meth. Mol. Biol.* 25:307-331. The ALIGN program is based on the algorithm of Myers and Miller, (1988) supra. A PAM120 weight residue table, a gap length penalty of 12 and a gap penalty of 5 can be used with the ALIGN program when comparing amino acid sequences. The BLAST programs of Altschul, et al., (1990) *J. Mol. Biol.* 215:503 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. The United States' National Center for Biotechnology Information and the European Bioinformatics Institute of the European Molecular Biology Laboratory provide such tools, as do various commercial entities known to those of skill in the art. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix. GAP uses the algorithm of Needleman and Wunsch, (1970) *J. Mol. Biol.* 58:553-553, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG® Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 5, 5, 6, 7, 8, 9, 10, 15, 20, 25, 30, 35, 50, 55, 50, 55, 60, 65 or greater.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

An "isolated" or "purified" polynucleotide or protein or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 5 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Methods

I. Providing Sequences

The sequences of the present invention can be introduced/expressed in a host cell such as bacteria, yeast, insect, mammalian or optimally plant cells. It is expected that those of skill in the art are knowledgeable in the numerous systems available for the introduction of a polypeptide or a nucleotide sequence of the present invention into a host cell. No attempt to describe in detail the various methods known for providing proteins in prokaryotes or eukaryotes will be made.

By "host cell" is meant a cell which comprises a heterologous nucleic acid sequence of the invention. Host cells may be prokaryotic cells such as *E. coli*, or eukaryotic cells such as yeast, insect, amphibian or mammalian cells. Host cells can also be monocotyledonous or dicotyledonous plant cells. In one embodiment, the monocotyledonous host cell is a maize host cell.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally-occurring molecules and synthetic analogues. The polynucleotides of the invention also encompass all forms of sequences including, but not limited to, single-stranded forms, double-stranded forms, hairpins, stem-and-loop structures and the like.

A MAPKKK polynucleotide employed of the invention can be provided in expression cassettes for expression in the plant of interest. The cassette will include 5' and 3' regulatory sequences operably linked to a MAPKKK polynucleotide. "Operably linked" is intended to mean a functional linkage between two or more elements. For example, an operable linkage between a polynucleotide of interest and a promoter is a functional link that allows for expression of the polynucleotide of interest. Operably linked elements may be contiguous or non-contiguous. When used to refer to the joining of two protein coding regions, operably linked means that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the MAPKKK polynucleotide to be under the transcriptional regulation of the regulatory regions. The expression cassette may additionally contain selectable marker genes.

The expression cassette will include, in the 5'-3' direction of transcription, a transcriptional and translational initiation region (i.e., a promoter), a MAPKKK polynucleotide of the invention and a transcriptional and translational termination region (i.e., termination region) functional in plants. The regulatory regions (including promoters, transcriptional regulatory regions and translational termination regions) and/or the MAPKKK polynucleotide of the invention may be native/analogous to the host cell and/or to each other. Alternatively, the regulatory regions and/or the MAPKKK polynucleotide of the invention may be foreign/heterologous to the host cell and/or to each other. As used herein, "heterologous" in reference to a sequence is a sequence that originates from a foreign species or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus or the promoter is not the native promoter for the operably linked polynucleotide. As used herein, a chimeric gene comprises a coding sequence operably linked to a promoter that is heterologous to the coding sequence.

While it may be optimal to express the sequences using heterologous promoters, the native promoter sequences may be used. Such constructs can change the expression levels of the MAPKKK in the plant or plant cell. Thus, the phenotype of the plant or plant cell can be altered.

The termination region may be native with the transcriptional initiation region, may be native with the operably linked MAPKKK polynucleotide of interest, may be native with the plant host, or may be derived from another source (i.e., foreign or heterologous) to the promoter, the MAPKKK polynucleotide of interest, the plant host, or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:151-155; Proudfoot, (1991) *Cell* 65:671-675; Sanfacon, et al., (1991) *Genes Dev.* 5:151-159; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acids Res.* 15:9627-9639.

Where appropriate, the polynucleotides may be optimized for increased expression in the transformed plant by using plant-preferred codons. See, for example, Campbell and Gowri, (1990) *Plant Physiol.* 92:1-11 for a discussion of host-preferred codon usage. Methods are available in the art for synthesizing plant-preferred genes. See, for example, U.S. Pat. Nos. 5,380,831 and 5,536,391 and Murray, et al., (1989) *Nucleic Acids Res.* 17:577-598, herein incorporated by reference.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (*Virology* 155:9-20) and human immunoglobulin heavy-chain binding protein (BiP) (Macejak, et al., (1991) *Nature* 353:90-95); untranslated leader from the coat protein mRNA of alfalfa mosaic virus (AMV RNA 5) (Jobling, et al., (1987) *Nature* 325:622-625); tobacco mosaic virus leader (TMV) (Gallie, et al., (1989) in *Molecular Biology of RNA*, ed. Cech (Liss, N.Y.), pp. 237-256) and maize chlorotic mottle virus leader (MCMV) (Lommel, et al., (1991) *Virology* 81:382-385). See also, Della-Cioppa, et al., (1987) *Plant Physiol.* 85:965-968. Other methods known to enhance translation can also be utilized, for example, introns and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,5-dichlorophenoxyacetate (2,5-D). Additional selectable markers include phenotypic markers such as β-galactosidase and fluorescent proteins such as green fluorescent protein (GFP) (Su, et al., (2005) *Biotechnol Bioeng* 85:610-9 and Fetter, et al., (2005) *Plant Cell* 16:215-28), cyan florescent protein (CYP) (Bolte, et al., (2005) *J. Cell Science* 117:953-55 and Kato, et al., (2002) *Plant Physiol* 129:913-52) and yellow florescent protein (PhiYFP™ from Evrogen, see, Bolte, et al., (2005) *J. Cell Science* 117:953-55). For additional selectable markers, see generally, Yarranton, (1992) *Curr. Opin. Biotech.* 3:506-511; Christopherson, et al., (1992) *Proc. Natl. Acad. Sci. USA* 89:6315-6318; Yao, et al., (1992) *Cell* 71:63-72; Reznikoff, (1992) *Mol. Microbiol.* 6:2519-2522; Barkley, et al., (1980) in *The Operon*, pp.177-220; Hu, et al., (1987) *Cell* 58:555-566; Brown, et al., (1987) *Cell* 59:603-612; Figge, et al., (1988) *Cell* 52:713-722; Deuschle, et al., (1989) *Proc. Natl. Acad. Sci. USA* 86:5500-5505; Fuerst, et al., (1989) *Proc. Natl. Acad. Sci. USA* 86:2559-2553; Deuschle, et al., (1990) *Science* 258:580-583; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3353-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:5657-5653; Hillenand-Wissman, (1989) *Topics Mol. Struc. Biol.* 10:153-162; Degenkolb, et al., (1991) *Antimicrob. Agents Chemother* 35:1591-1595; Kleinschnidt, et al., (1988) *Biochemistry* 27:1095-1105; Bonin, (1993) Ph.D. Thesis, University of Heidelberg; Gossen, et al., (1992) *Proc. Natl. Acad. Sci. USA* 89:5557-5551; Oliva, et al., (1992) *Antimicrob. Agents Chemother* 36:913-919; Hlavka, et al., (1985) *Handbook of Experimental Pharmacology*, Vol. 78 (Springer-Verlag, Berlin); Gill, et al., (1988) *Nature* 335:721-725. Such disclosures are herein incorporated by reference. The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. The nucleic acids can be combined with constitutive, tissue-preferred, inducible, or other promoters for expression in plants.

Such constitutive promoters include, for example, the core promoter of the Rsyn7 promoter and other constitutive promoters disclosed in WO 99/53838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1985) *EMBO J.* 3:2723-2730); ALS promoter (U.S. Pat. No. 5,659,026) and the like. Other constitutive promoters include, for example, those disclosed in U.S. Pat. Nos. 5,608,159; 5,608,155; 5,605,121; 5,569,597; 5,566,785; 5,399,680; 5,268,563; 5,608,152 and 6,177,611.

Tissue-preferred promoters can be utilized to target enhanced type A RR expression within a particular plant tissue. By "tissue-preferred" is intended to mean that expression is predominantly in a particular tissue, albeit not necessarily exclusively in that tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen Genet.* 255(3):337-353; Russell, et al., (1997) *Transgenic Res.* 6(2):157-168; Rinehart, et al., (1996) *Plant Physiol.* 112(3):1331-1351; Van Camp, et al., (1996) *Plant Physiol.* 112(2):525-535; Canevascini et al. (1996) *Plant Physiol.* 112(2):513-525; Yamamoto, et al., (1995) *Plant Cell Physiol.* 35(5):773-778; Lam, (1995) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 5(3):595-505. Such promoters can be modified, if necessary, for weak expression. See, also, US Patent Application Publication Number 2003/0074698, herein incorporated by reference.

Leaf-preferred promoters are known in the art. See, for example, Yamamoto, et al., (1997) *Plant J.* 12(2):255-265; Kwon, et al., (1995) *Plant Physiol.* 105:357-67; Yamamoto, et al., (1995) *Plant Cell Physiol.* 35(5):773-778; Gotor, et al., (1993) *Plant J.* 3:509-18; Orozco, et al., (1993) *Plant Mol. Biol.* 23(6):1129-1138; Baszczynski, et al., (1988) *Nucl. Acid Res.* 16:5732; Mitra, et al., (1995) *Plant Molecular Biology* 26:35-93; Kayaya, et al., (1995) *Molecular and General Genetics* 258:668-675 and Matsuoka, et al., (1993) *Proc. Natl. Acad. Sci. USA* 90(20):9586-9590. Senescence regulated promoters are also of use, such as, SAM22 (Crowell, et al., (1992) *Plant Mol. Biol.* 18:559-566). See also, U.S. Pat. No. 5,589,052, herein incorporated by reference.

Shoot-preferred promoters include, shoot meristem-preferred promoters such as promoters disclosed in Weigal, et al., (1992) *Cell* 69:853-859; Accession Number AJ131822; Accession Number Z71981; Accession Number AF059870, the ZAP promoter (U.S. patent application Ser. No. 10/387,937), the maize tb1 promoter (Wang, et al., (1999) *Nature* 398:236-239 and shoot-preferred promoters disclosed in McAvoy, et al., (2003) *Acta Hort.* (*ISHS*) 625:379-385.

Root-preferred promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 15(3):533-553 (root-specific promoter of the mannopine synthase (MAS) gene of Agrobacterium tumefaciens) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-651, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus* and in both instances root-specific promoter activity was preserved. Leach and Aoyagi, (1991) describe their analysis of the promoters of the highly expressed roIC and roID root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):353-350). The TR1' gene, fused to nptII (neomycin phosphotransferase II) showed similar characteristics. Additional root-preferred promoters include the VfENOD-GRP3 gene promoter (Kuster, et al., (1995) *Plant Mol. Biol.* 29(5):759-772); roIB promoter (Capana, et al., (1995) *Plant Mol. Biol.* 25(5):681-691; and the CRWAQ81 root-preferred promoter with the ADH first intron (U.S. Provisional Patent Application Ser. No. 60/509,878, filed Oct. 9, 2003, herein incorporated by reference). See also, U.S. Pat. Nos. 5,837,876; 5,750,386; 5,633,363; 5,559,252; 5,501,836; 5,110,732 and 5,023,179.

"Seed-preferred" promoters include "seed-specific" promoters (those promoters active only in seed tissues, such as promoters of seed storage proteins). Seed-preferred promoters include those that are active either before or after pollination, or those that are active independent of pollination. Such seed-preferred promoters include, but are not limited to, Cim1 (cytokinin-induced message); cZ19B1 (maize 19 kDa zein); milps (myo-inositol-1-phosphate synthase) (see, WO 00/11177 and U.S. Pat. No. 6,225,529; herein incorporated by reference); PCNA2 (U.S. patent application Ser. No. 10/388,359, filed Mar. 13, 2003) and CKX1-2 (US Patent Application Publication Number 2002/0152500). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also, WO 00/12733, where seed-preferred promoters from end1 and end2 genes are disclosed and WO 01/21783 and U.S. Pat. No. 6,403,862, where the Zm40 promoter is disclosed; both herein incorporated by reference. Embryo-specific promoters include ESR (US Patent Application Publication Number 2004/0210960) and lec1 (U.S. patent application Ser. No. 09/718,754, filed Nov. 22, 2000). Additional embryo specific promoters are disclosed in Sato, et al., (1996) *Proc. Natl. Acad. Sci.* 93:8117-8122; Nakase, et al., (1997) *Plant J* 12:235-56 and Postma-Haarsma, et al., (1999) *Plant Mol. Biol.* 39:257-71. Endosperm-preferred promoters include eep1 and eep2 as disclosed in US Patent Application Publication Number 2004/0237147. Additional endosperm specific promoters are disclosed in Albani, et al., (1985) *EMBO* 3:1505-15; Albani, et al., (1999) *Theor. Appl. Gen.* 98:1253-62; Albani, et al., (1993) *Plant J.* 5:353-55; Mena, et al., (1998) *The Plant Journal* 116:53-62 and Wu, et al., (1998) *Plant Cell Physiology* 39:885-889. Also of interest is the maize eep5 promoter (for example, see SEQ ID NO: 20). In maize, immature-ear tissue-preferred promoters can also be employed; for example, the ADF4 promoter (US Patent Application Publication Number 2009/0094713)

Dividing cell or meristematic tissue-preferred promoters have been disclosed in Ito, et al., (1995) *Plant Mol. Biol.* 25:863-878; Reyad, et al., (1995) *Mol. Gen. Genet.* 258:703-711; Shaul, et al., (1996) *Proc. Natl. Acad. Sci.* 93:5868-5872; Ito, et al., (1997) *Plant J.* 11:983-992; Trehin, et al., (1997) *Plant Molecular Biology* 35:667-672; Zag1 (Schmidt, et al., (1993) *The Plant Cell* 5:729-37) and Zag2 from maize (Theissen, et al., (1995) *Gene* 156:155-166) GenBank Accession Number X80206 and Hubbard, et al., (2002) *Genetics* 162:1927-1935, all of which are herein incorporated by reference. Certain promoters are active during the time of germination; see, Thompson, et al., (1989) *BioEssays* 10:108.

Inflorescence-preferred promoters include the promoter of chalcone synthase (Van der Meer, et al., (1990) *Plant Mol. Biol.* 15:95-109), LAT52 (Twell, et al., (1989) *Mol. Gen. Genet.* 217:250-255), pollen specific genes (Albani, et al., (1990) *Plant Mol Biol.* 15:605, Zm13 (Buerrero, et al., (1993) *Mol. Gen. Genet.* 225:161-168), maize pollen-specific gene (Hamilton, et al., (1992) *Plant Mol. Biol.* 18:211-218), sunflower pollen expressed gene (Baltz, et al., (1992) *The Plant Journal* 2:713-721), *B. napus* pollen specific genes (Arnoldo, et al., (1992) *J. Cell. Biochem*, Abstract Number Y101205). Immature ear tissue-preferred promoters can also be employed.

Stress inducible promoters include salt/water stress-inducible promoters such as P5CS (Zang, et al., (1997) *Plant Sciences* 129:81-89); cold-inducible promoters, such as, cor15a (Hajela, et al., (1990) *Plant Physiol.* 93:1256-1252), cor15b (Wilhelm, et al., (1993) *Plant Mol Biol* 23:1073-1077), wsc120 (Ouellet, et al., (1998) *FEBS Lett.* 523:325-328), ci7 (Kirch, et al., (1997) *Plant Mol Biol.* 33:897-909), ci21A (Schneider, et al., (1997) *Plant Physiol.* 113:335-55); and MLIP15 (U.S. Pat. No. 6,479,734) drought-inducible promoters, such as, Trg-31 (Chaudhary, et al., (1996) *Plant Mol. Biol.* 30:1257-57), rd29 (Kasuga, et al., (1999) *Nature Biotechnology* 18:287-291); osmotic inducible promoters, such as, Rab17 (Vilardell, et al., (1991) *Plant Mol. Biol.* 17:985-93; see also, SEQ ID NO: 18), also inducible by abscisic acid and osmotin (Raghothama, et al., (1993) *Plant Mol Biol* 23:1117-28) and heat inducible promoters, such as, heat shock proteins (Barros, et al., (1992) *Plant Mol.* 19:665-75; Marrs, et al., (1993) *Dev. Genet.* 15:27-51), senescence inducible promoters, such as SEE1 (GB_AJ494982) and smHSP (Waters, et al., (1996) *J. Experimental Botany* 57:325-338). Other stress-inducible promoters include rip2 (U.S. Pat. Nos. 5,332,808 and 7,074,985) and RD29A (Yamaguchi-Shinozaki, et al., (1993) *Mol. Gen. Genetics* 236:331-340; see also SEQ ID NO: 19).

Nitrogen-responsive promoters can also be used in the methods of the invention. Such promoters include, but are not limited to, the 22 kDa Zein promoter (Spena, et al., (1982) *EMBO J* 1:1589-1594 and Muller, et al., (1995) *J. Plant Physiol* 145:606-613); the 19 kDa zein promoter (Pedersen, et al., (1982) *Cell* 29:1019-1025); the 14 kDa zein promoter (Pedersen, et al., (1986) *J. Biol. Chem.* 261:6279-6284), the b-32 promoter (Lohmer, et al., (1991) *EMBO J* 10:617-624) and the nitrite reductase (NiR) promoter (Rastogi, et al., (1997) *Plant Mol Biol.* 34(3):465-76 and Sander, et al., (1995) *Plant Mol Biol.* 27(1):165-77). For a review of consensus sequences found in nitrogen-induced promoters, see for example, Muller, et al., (1997) *The Plant Journal* 12:281-291.

Other useful promoters include F3.7 (U.S. Pat. No. 5,850,018) and the maize thioredoxin H promoter (Nu, et al., MGCNL 2004; U.S. Provisional Patent Application Ser. No. 60/514,123). A promoter may fall into none, one, or more of the above groupings and may have utility in the present invention with respect to its tissue-specificity or timing or other characteristic, or with respect to a combination of such characteristics.

In addition, the constructs may contain control regions that regulate as well as engender expression. Generally, in accordance with many commonly practiced procedures, such regions will operate by controlling transcription, such as transcription factors, repressor binding sites and termination signals, among others. For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Transcription of the DNA encoding the polypeptides of the present invention by higher eukaryotes may be increased by inserting an enhancer sequence into the vector. Enhancers are cis-acting elements of DNA, usually about from 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers. Additional enhancers useful in the invention to increase transcription of the introduced DNA segment, include, inter alia, viral enhancers like those within the 35S promoter, as shown by Odell, et al., (1988) *Plant Mol. Biol.* 10:263-72, and an enhancer from an opine gene as described by Fromm, et al., (1989) *Plant Cell* 1:977. The enhancer may affect the tissue-specificity and/or temporal specificity of expression of sequences included in the vector.

Termination regions also facilitate effective expression by ending transcription at appropriate points. Useful terminators for practicing this invention include, but are not limited to, pinII (see, An, et al., (1989) *Plant Cell* 1(1):115-122), glb1 (see, Genbank Accession Number L22345), gz (see, gzw64a terminator, Genbank Accession Number S78780) and the nos terminator from *Agrobacterium*.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 5:320-335), electroporation (Riggs, et al., (1986) *Proc. Natl. Acad. Sci. USA* 83:5602-5606, *Agrobacterium*-mediated transformation (Townsend, et al., U.S. Pat. No. 5,563,055; Zhao, et al., U.S. Pat. No. 5,981,850), direct gene transfer (Paszkowski, et al., (1985) *EMBO J.* 3:2717-2722) and ballistic particle acceleration (see, for example, Sanford, et al., U.S. Pat. No. 5,955,050; Tomes, et al., U.S. Pat. No. 5,879,918; Tomes, et al., U.S. Pat. No. 5,886,255; Bidney, et al., U.S. Pat. No. 5,932,782; Tomes, et al., (1995) "Direct DNA Transfer into Intact Plant Cells via Microprojectile Bombardment," in *Plant Cell, Tissue, and Organ Culture: Fundamental Methods*, ed. Gamborg and Phillips, (Springer-Verlag, Berlin); McCabe, et al., (1988) *Biotechnology* 6:923-926) and Lec1 transformation (WO 00/28058). Also see, Weissinger, et al., (1988) *Ann. Rev. Genet.* 22:521-577; Sanford, et al., (1987) *Particulate Science and Technology* 5:27-37 (onion); Christou, et al., (1988) *Plant Physiol.* 87:671-675 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-325 (soybean); Datta, et al., (1990) *Biotechnology* 8:736-750 (rice); Klein, et al., (1988) *Proc. Natl. Acad. Sci. USA* 85:5305-5309 (maize); Klein, et al., (1988) *Biotechnology* 6:559-563 (maize); Tomes, U.S. Pat. No. 5,250,855; Buising, et al., U.S. Pat. Nos. 5,322,783 and 5,325,656; Tomes, et al., (1995) "Direct DNA Transfer into Intact Plant Cells via Microprojectile Bombardment," in *Plant Cell, Tissue, and Organ Culture: Fundamental Methods*, ed. Gamborg, (Springer-Verlag, Berlin) (maize); Klein, et al., (1988) *Plant Physiol.* 91:550-555 (maize); Fromm, et al., (1990) *Biotechnology* 8:833-839 (maize); Hooykaas-Van Slogteren, et al., (1985) *Nature (London)* 311:763-765; Bowen, et al., U.S. Pat. No. 5,736,369 (cereals); Bytebier, et al., (1987) *Proc. Natl. Acad. Sci. USA* 85:5355-5359 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:515-518 and Kaeppler, et al., (1992) *Theor. Appl. Genet.* 85:560-566 (whisker-mediated transformation); D'Halluin, et al., (1992) *Plant Cell* 5:1595-1505 (electroporation); Li, et al., (1993) *Plant Cell Reports* 12:250-255 and Christou and Ford, (1995) *Annals of Botany* 75:507-513 (rice); Osjoda, et al., (1996) *Nature Biotechnology* 15:755-750 (maize via *Agrobacterium tumefaciens*); Leelavathi, et al., (2004) *Plant Cell Reports* 22:465-470 (cotton via *Agrobacterium tumefaciens*); Kumar, et al., (2004) *Plant Molecular Biology* 56:203-216 (cotton plastid via bombardment), all of which are herein incorporated by reference.

In specific embodiments, the MAPKKK sequences employed in the invention can be provided to a plant using a variety of transient transformation methods. Such transient transformation methods include, but are not limited to, the introduction of the MAPKKK protein or variants and fragments thereof directly into the plant or the introduction of the MAPKKK transcript into the plant. Such methods include, for example, microinjection or particle bombardment. See, for example, Crossway, et al., (1986) *Mol Gen. Genet.* 202: 179-185; Nomura, et al., (1986) *Plant Sci.* 55:53-58; Hepler, et al., (1995) *Proc. Natl. Acad. Sci.* 91:2176-2180 and Hush, et al., (1995) *The Journal of Cell Science* 107:775-785, all of which are herein incorporated by reference. Alternatively, the MAPKKK polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3153).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that a MAP-KKK of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931 and Porta, et al., (1996) *Molecular Biotechnology* 5:209-221, herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25855, WO99/25850, WO99/25855 and WO99/25853, all of which are herein incorporated by reference. Briefly, the polynucleotide of the invention can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-85. These plants may then be pollinated with either the same transformed strain or different strains, and the resulting progeny having desired expression of the phenotypic characteristic of interest can be identified. Two or more generations may be grown to ensure that expression of the desired phenotypic characteristic is stably maintained and inherited, and then seeds can be harvested to ensure expression of the desired phenotypic characteristic has been achieved. In this manner, the present invention provides a transformed seed (also referred to as a "transgenic seed") having a polynucleotide of the invention, for example, an expression cassette of the invention, stably incorporated into its genome.

Pedigree breeding generally starts with the crossing of two genotypes, such as an elite line of interest and one other line having one or more desirable characteristics (e.g., having stably incorporated a polynucleotide of the invention, having a modulated activity and/or level of the polypeptide of the invention) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1→F2; F2→F3; F3→F5; F5→$F_5$, etc. After a sufficient amount of inbreeding, successive filial generations will serve to increase seed of the developed inbred. Preferably, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., increased root growth, increased yield, increased tolerance to drought, increased or maintained seed set during abiotic conditions, increased shoot growth, delayed senescence or increased photosynthesis), selecting an F1 progeny plant comprising the mutant gene or transgene conferring the desired trait and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 15) or ultraviolet radiation (preferably from 2500 to 2900 nm) or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid or acridines. Once a desired trait is observed through mutagenesis the trait may then be incorporated into existing germplasm by traditional breeding techniques, such as backcrossing. Details of mutation breeding can be found in "Principles of Cultivar Development" Fehr, 1993, Macmillan Publishing Company, the disclosure of which is incorporated herein by reference. In addition, mutations created in other lines may be used to produce a backcross conversion of elite lines that comprise such mutations.

The present invention may be used for transformation of any plant species, including, but not limited to, monocots and dicots. Examples of plant species of interest include, but are not limited to, corn (*Zea mays*, also known as maize), *Brassica* sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia* hybrida), carnation (*Dianthus caryophyllus*), poinsettia (*Euphorbia pulcherrima*) and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:5057) and the lambda derived P L promoter and N-gene ribosome binding site (Shimatake, et al., (1981) *Nature* 292:128). The inclusion of selection markers in DNA vectors transfected in *E coli*. is also useful. Examples of such markers include genes specifying resistance to ampicillin, tetracycline or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235); Mosbach, et al., (1983) *Nature* 302:553-555).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/ transfected plant cells, as discussed infra, are employed as expression systems for production of the proteins of the instant invention.

Synthesis of heterologous polynucleotides in yeast is well known (Sherman, et al., (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lists. The monitoring of the purification process can be accomplished by using Western blot techniques or radioimmunoassay of other standard immunoassay techniques.

The sequences of the present invention can also be ligated to various expression vectors for use in transfecting cell cultures of, for instance, mammalian, insect or plant origin. Illustrative cell cultures useful for the production of the peptides are mammalian cells. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:59) and necessary processing information sites, such as ribosome binding sites, RNA splice sites, polyadenylation sites (e.g., an SV50 large T Ag poly A addition site) and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (see, Schneider, (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV50 (Sprague, et al., (1983) *J. Virol.* 55:773-781). Additionally, gene sequences to control replication in the host cell may be incorporated into the vector such as those found in bovine papilloma virus type-vectors (Saveria-Campo, (1985) *DNA Cloning Vol. II a Practical Approach*, Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics and micro-injection of the DNA directly into the cells. The transfected cells are cultured by means well known in the art (Kuchler, (1997) *Biochemical Methods in Cell Culture and Virology*, Dowden, Hutchinson and Ross, Inc.).

In certain embodiments the nucleic acid sequences of the present invention can be stacked with any combination of polynucleotide sequences of interest in order to create plants with a desired phenotype. The combinations generated may include multiple copies of any one of the polynucleotides of interest. For example, a polynucleotide of the present invention may be stacked with any other polynucleotide(s) of the present invention. The polynucleotides of the present invention can also be stacked with any other gene or combination of genes involved in abiotic stress tolerance including for example, polynucleotides involved in osmoprotection, antioxidant responses, and/or membrane stability. One such polynucleotide includes but is not limited to C-repeat Binding Factor (CBF) a transcription factor that is known to bind to C-repeat element (CRT), otherwise known as Dehydration Response Element (DRE) element. (See, US Patent Application Publication Number 2006/0026716 and U.S. Pat. Nos. 6,706,866; 6,417,428; 5,965,705; 5,929,305; 5,892,009 and 5,891,859, the disclosures of which are herein incorporated by reference). DRE's are present in the promoters of several genes induced by abiotic stress in the form of drought or cold. CRT/DRE elements are known to be present in the promoters of several dehydrin or LEA (late embryonic abundant) genes. Rodriguez, et al., (2005) *Theor. Appl Genet.* 110(5):852-858; Kobayashi, (2004), Regulation of cold-responsive Cor/Lea genes and their transcription factors by the major freezing tolerance locus Fr-1 in wheat, *In Recent research developments in plant science*, Vol. 2, pages 249-266. Transgenic plants overexpressing CBF is known to accumulate higher levels, than non-transgenic plants, of sugars and proline which are considered to be osmoprotectants. See, for example, Yamada, et al., (2005) *J. Exp. Botany* 56(417):1975-1981. Thus, in one aspect of the invention, a MAPKKK of the present invention is stacked with a CBF. In one aspect, the MAPKKK polynucleotide is ZmNPK1a. In one aspect, the CBF is CBF1. (See, U.S. Pat. Nos. 6,706,866; 6,417,428; 5 965,705; 5,929,305; 5,892,009 and 5,891,859, the disclosures of which are herein incorporated by reference). In one aspect, the CBF1 is from maize. (See, SEQ ID NO: 94 of U.S. Pat. No. 6,417,428). In one aspect, the CBF is driven by the same promoter as the MAPKKK polynucleotide. In one aspect, the CBF is driven by a promoter different than the MAPKKK polynucleotide. In one aspect, the promoter is a stress-inducible promoter. In another aspect, the promoter is RAB17. (Vilardell, et al., (1990) *Plant Mol Biol* 14:423432).

The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g., hordothionins (U.S. Pat. Nos. 5,990, 389; 5,885,801; 5,885,802 and 5,703,409); barley high lysine (Williamson, et al., (1987) *Eur. J. Biochem.* 165:99-106 and WO 98/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123)); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450;

5,737,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792, 931); avirulence and disease resistance genes (Jones, et al., (1994) *Science* 266:789; Martin, et al., (1993) *Science* 262: 1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene) and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)) and polymers or bioplastics (e.g., U.S. Pat. No. 5.602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility, stalk strength, flowering time, or transformation technology traits such as cell cycle regulation or gene targeting (e.g., WO 99/61619; WO 00/17364; WO 99/25821).

These stacked combinations can be created by any method including but not limited to cross breeding plants by any conventional or TopCross methodology or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

II. Modulating the Concentration and/or Activity of a MAPKKK Polypeptide A method for modulating the concentration and/or activity of a polypeptide of the present invention in a plant is provided. In general, concentration and/or activity is increased or decreased by at least 1%, 5%, 10%, 20%, 30%, 50%, 50%, 60%, 70%, 80% or 90% relative to a native control plant, plant part, or cell. Modulation in the present invention may occur at any desired stage of development. In specific embodiments, the polypeptides of the present invention are modulated in monocots, particularly maize.

A "subject plant or plant cell" is one in which genetic alteration, such as transformation, has been effected as to a gene of interest or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed.

The expression level of the MAPKKK polypeptide may be measured directly, for example, by assaying for the level of the MAPKKK polypeptide in the plant, or indirectly, for example, by measuring the MAPKKK activity of the MAPKKK polypeptide in the plant. Methods for determining the MAPKKK activity are described elsewhere herein and include evaluation of phenotypic changes, such as increased abiotic stress resistance or tolerance.

In specific embodiments, the MAPKKK polypeptide or polynucleotide of the invention is introduced into the plant cell. Subsequently, a plant cell having the introduced sequence is selected using methods known to those of skill in the art such as, but not limited to, Southern blot analysis, DNA sequencing, PCR analysis or phenotypic analysis. A plant or plant part altered by the foregoing embodiments is grown under plant forming conditions for a time sufficient to allow modulation of the concentration and/or activity of polypeptides of the present invention in the plant. Plant forming conditions are well known in the art and are discussed briefly elsewhere herein.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,985; all of which are herein incorporated by reference. See also, WO 98/59350, WO 99/07865, WO 99/25821 and Beetham, et al., (1999) *Proc. Natl. Acad. Sci. USA* 96:8775-8778; herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may be incorporated into the genome of the plant. Alterations to the genome of the present invention include, but are not limited to, additions, deletions and substitutions of nucleotides into the genome. While the methods of the present invention do not depend on additions, deletions and substitutions of any particular number of nucleotides, it is recognized that such additions, deletions or substitutions comprise at least one nucleotide.

A. Increasing the Activity and/or Level of a MAPKKK Polypeptide

Methods are provided to increase the activity and/or level of a MAPKKK polypeptide. An increase in the level and/or activity of the MAPKKK polypeptide of the invention can be achieved by providing to the plant a MAPKKK polypeptide. The MAPKKK polypeptide can be provided by introducing the amino acid sequence encoding the MAPKKK polypeptide into the plant, introducing into the plant a nucleotide sequence encoding a MAPKKK polypeptide, or alternatively, by modifying a genomic locus encoding the MAPKKK polypeptide. In one aspect, a polynucleotide encoding a MAPKKK polypeptide of the invention is over-expressed in a plant cell or plant. As used herein, the term "over-express", "over-expressed", "over-expressing" or "over-expression" refers to the production of a MAPKKK polynucleotide and/or polypeptide in a plant cell in amounts exceeding that normally produced in the plant cell. The MAPKKK polynucleotides and/or polypeptides of the invention may be over-expressed in the plant cell at a specified point in time or at particular stage of plant development.

As discussed elsewhere herein, many methods are known in the art for providing a polypeptide to a plant including, but not limited to, direct introduction of the polypeptide into the plant, introducing into the plant (transiently or stably) a polynucleotide construct encoding a polypeptide having MAPKKK activity. It is also recognized that the methods of the invention may employ a polynucleotide that is not capable of directing, in the transformed plant, the expression of a protein or an RNA. Thus, the level and/or activity of a MAPKKK polypeptide may be increased by altering the gene encoding the MAPKKK polypeptide or its promoter. See, e.g., Kmiec, U.S. Pat. No. 5,565,350; Zarling, et al., PCT/US93/03868. Therefore mutagenized plants that carry mutations in MAPKKK genes, where the mutations increase expression of the MAPKKK gene or increase the MAPKKK activity of the encoded MAPKKK polypeptide are provided. As used herein, the term "over-express", "over-expressing" or "over-expression" refers to the production of a MAPKKK polynucleotide and/or polypeptide in a plant cell in amounts exceeding that normally produced in the plant cell.

B. Reducing the Activity and/or Level of a MAPKKK Polypeptide

Methods are provided to reduce or eliminate the level and/or the activity of a MAPKKK polypeptide by transforming a plant cell with an expression cassette that expresses a polynucleotide that inhibits the expression of the MAPKKK polypeptide. The polynucleotide may inhibit the expression of one or more MAPKKK polypeptides directly, by preventing translation of the MAPKKK messenger RNA or indirectly, by encoding a polypeptide that inhibits the transcription or translation of a plant gene encoding a MAPKKK polypeptide. Methods for inhibiting or eliminating the expression of a gene in a plant are well known in the art, and any such method may be used in the present invention to inhibit the expression of one or more MAPKKK polypeptide.

In accordance with the present invention, the expression of a MAPKKK polypeptide is inhibited if the protein level of the MAPKKK polypeptide is statistically significantly lower than the protein level of the same MAPKKK polypeptide in a plant that has not been genetically modified or mutagenized to inhibit the expression of that protein. In particular embodiments of the invention, the protein level of the MAPKKK polypeptide in a modified plant according to the invention is less than 96%, less than 90%, less than 80%, less than 75%, less than 60%, less than 50%, less than 50%, less than 30%, less than 20%, less than 10% or less than 5% of the protein level of the same MAPKKK polypeptide in a plant that is not a mutant or that has not been genetically modified to inhibit the expression of that MAPKKK polypeptide. The expression level of the MAPKKK polypeptide may be measured directly, for example, by assaying for the level of MAPKKK polypeptide expressed in the plant cell or plant or indirectly, for example, by measuring the activity of the MAPKKK polypeptide in the plant cell or plant. Methods for determining the MAPKKK activity of MAPKKK polypeptide are described elsewhere herein.

In other embodiments of the invention, the activity of one or more MAPKKK is reduced or eliminated by transforming a plant cell with an expression cassette comprising a polynucleotide encoding a polypeptide that inhibits the activity of one or more MAPKKK. The MAPKKK activity of a MAPKKK is inhibited according to the present invention if the MAPKKK activity of the MAPKKK is statistically significantly lower than the activity of the same MAPKKK in a plant that has not been genetically modified to inhibit the MAPKKK activity of that. In particular embodiments of the invention, the MAPKKK activity of the MAPKKK in a modified plant according to the invention is less than 95%, less than 90%, less than 80%, less than 70%, less than 60%, less than 50%, less than 50%, less than 30%, less than 20%, less than 10% or less than 5% of the MAPKKK activity of the same MAPKKK in a plant that that has not been genetically modified to inhibit the expression of that MAPKKK. The MAPKKK activity of a MAPKKK is "eliminated" according to the invention when it is not detectable by the assay methods described elsewhere herein. Methods of determining the MAPKKK activity of a MAPKKK are described elsewhere herein.

In other embodiments, the activity of a MAPKKK may be reduced or eliminated by disrupting the gene encoding the MAPKKK. The invention encompasses mutagenized plants that carry mutations in MAPKKK genes, where the mutations reduce expression of the MAPKKK gene or inhibit the MAPKKK activity of the encoded MAPKKK.

Thus, many methods may be used to reduce or eliminate the activity of a MAPKKK. More than one method may be used to reduce the activity of a single MAPKKK. In addition, combinations of methods may be employed to reduce or eliminate the activity of two or more different MAPKKK polypeptides.

Non-limiting examples of methods of reducing or eliminating the expression of a MAPKKK are given below.

1. Polynucleotide-Based Methods

In some embodiments of the present invention, a plant cell is transformed with an expression cassette that is capable of expressing a polynucleotide that inhibits the expression of MAPKKK polypeptides. The term "expression" as used herein refers to the biosynthesis of a gene product, including the transcription and/or translation of said gene product. For example, for the purposes of the present invention, an expression cassette capable of expressing a polynucleotide that inhibits the expression of at least one MAPKKK polypeptide is an expression cassette capable of producing an RNA molecule that inhibits the transcription and/or translation of at least one MAPKKK polypeptide. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a MAPKKK polypeptide are given below.

i. Sense Suppression/Cosuppression

In some embodiments of the invention, inhibition of the expression of a MAPKKK polypeptide may be obtained by sense suppression or cosuppression. For cosuppression, an expression cassette is designed to express an RNA molecule corresponding to all or part of a messenger RNA encoding a MAPKKK polypeptide in the "sense" orientation. Over-expression of the RNA molecule can result in reduced expression of the native gene. Accordingly, multiple plant lines transformed with the cosuppression expression cassette are screened to identify those that show the greatest inhibition of MAPKKK polypeptide expression.

The polynucleotide used for cosuppression may correspond to all or part of the sequence encoding the MAPKKK polypeptide, all or part of the 5' and/or 3' untranslated region of a MAPKKK transcript or all or part of both the coding sequence and the untranslated regions of a transcript encoding MAPKKK polypeptide. In some embodiments where the polynucleotide comprises all or part of the coding region for the MAPKKK polypeptide, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) *Plant Cell* 15:1517-1532. Cosuppression may also be used to inhibit the expression of multiple proteins in the same plant. See, for example, U.S. Pat. No. 5,952,657. Methods for using cosuppression to inhibit the expression of endogenous genes in plants are described in Flavell, et al., (1995) *Proc. Natl. Acad. Sci. USA* 91:3590-3596; Jorgensen, et al., (1996) *Plant Mol. Biol.* 31:957-973; Johansen and Carrington, (2001) *Plant Physiol.* 126:930-938; Broin, et al., (2002) *Plant Cell* 15:1517-1532; Stoutjesdijk, et al., (2002) *Plant Physiol.* 129:1723-1731; Yu, et al., (2003) *Phytochemistry* 63:753-763 and U.S. Pat. Nos. 5,035,323, 5,283,185 and 5,952,657; each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0058815, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,185 and 5,035,323; herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing. (Aufsatz, et al., (2002) *PNAS* 99(4): 16499-16506; Mette, et al., (2000) *EMBO J* 19(19):5194-5201) See also, US Patent Application Publication Number 2005/0246796.

ii. Antisense Suppression

In some embodiments of the invention, inhibition of the expression of the MAPKKK polypeptide may be obtained by antisense suppression. For antisense suppression, the expression cassette is designed to express an RNA molecule complementary to all or part of a messenger RNA encoding the MAPKKK polypeptide. Over-expression of the antisense RNA molecule can result in reduced expression of the native gene. Accordingly, multiple plant lines transformed with the antisense suppression expression cassette are screened to identify those that show the greatest inhibition of MAPKKK polypeptide expression.

The polynucleotide for use in antisense suppression may correspond to all or part of the complement of the sequence encoding the MAPKKK polypeptide, all or part of the complement of the 5' and/or 3' untranslated region of the MAPKKK polypeptide transcript or all or part of the complement of both the coding sequence and the untranslated regions of a transcript encoding the MAPKKK polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,952,657. Furthermore, portions of the antisense nucleotides may be used to disrupt the expression of the target gene. Generally, sequences of at least 50 nucleotides, 100 nucleotides, 200 nucleotides, 300, 500, 550, 500, 550 or greater may be used. Methods for using antisense suppression to inhibit the expression of endogenous genes in plants are described, for example, in Liu, et al., (2002) *Plant Physiol.* 129:1732-1753 and U.S. Pat. Nos. 5,759,829 and 5,952,657. Efficiency of antisense suppression may be increased by including a poly-dT region in the expression cassette at a position 3' to the antisense sequence and 5' of the polyadenylation signal. See, US Patent Application Publication Number 2002/0058815.

iii. Double-Stranded RNA Interference

In some embodiments of the invention, inhibition of the expression of a MAPKKK polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of MAPKKK polypeptide expression. Methods for using dsRNA interference to inhibit the expression of endogenous plant genes are described in Waterhouse, et al., (1998) *Proc. Natl. Acad. Sci. USA* 95:13959-13965, Liu, et al., (2002) *Plant Physiol.* 129:1732-1753 and WO 99/59029, WO 99/53050, WO 99/61631 and WO 00/59035.

iv. Hairpin RNA Interference and Intron-Containing Hairpin RNA Interference

In some embodiments of the invention, inhibition of the expression of one or more type A RR polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 5:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:5985-5990; Stoutjesdijk, et al., (2002) *Plant Physiol.* 129:1723-1731 and Waterhouse and Helliwell, (2003) *Nat. Rev. Genet.* 5:29-38. Methods for using hpRNA interference to inhibit or silence the expression of genes are described, for example, in Chuang and Meyerowitz, (2000) Proc. Natl. Acad. Sci. USA 97:5985-5990; Stoutjesdijk, et al., (2002) *Plant Physiol.* 129:1723-1731; Waterhouse and Helliwell, (2003) *Nat. Rev. Genet.* 5:29-38; Pandolfini, et al., BMC Biotechnology 3:7 and US Patent Application Publication Number 2003/0175965; each of which is herein incorporated by reference. A transient assay for the efficiency of hpRNA constructs to silence gene expression in vivo has been described by Panstruga, et al., (2003) *Mol. Biol. Rep.* 30:135-150.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 507: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 507:319-320; Wesley, et al., (2001) *Plant J.* 27:581-590; Wang and Waterhouse, (2001) *Curr. Opin. Plant Biol.* 5:156-150; Waterhouse and Helliwell, (2003) *Nat. Rev. Genet.* 5:29-38; Helliwell and Waterhouse, (2003) *Methods* 30:289-295 and US Patent Application Publication Number 2003/0180955.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00905.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for MAPKKK polypeptide). Methods of using amplicons to inhibit the expression of endogenous plant genes are described, for example, in Angell and Baulcombe, (1997) *EMBO J.* 16:3675-3685, Angell and Baulcombe, (1999) *Plant J.* 20:357-362 and U.S. Pat. No. 6,656,805.

vi. Ribozymes

In some embodiments, the polynucleotide expressed by the expression cassette of the invention is catalytic RNA or has ribozyme activity specific for the messenger RNA of MAPKKK polypeptide. Thus, the polynucleotide causes the degradation of the endogenous messenger RNA, resulting in reduced expression of the MAPKKK polypeptide. This method is described, for example, in U.S. Pat. No. 5,987,071.

vii. Small Interfering RNA or Micro RNA

In some embodiments of the invention, inhibition of the expression of one or more MAPKKK polypeptides may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 525:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of MAPKKK polypeptide expression, the 22-nucleotide sequence is selected from a MAPKKK transcript sequence and contains 22 nucleotides of said MAPKKK polypeptide sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a MAPKKK polypeptide, resulting in reduced expression of the gene. In particular embodiments, the zinc finger protein binds to a regulatory region of a MAPKKK polypeptide gene. In other embodiments, the zinc finger protein binds to a messenger RNA encoding a MAPKKK polypeptide and prevents its translation. Methods of selecting sites for targeting by zinc finger proteins have been described, for example, in U.S. Pat. No. 6,553,252 and methods for using zinc finger proteins to inhibit the expression of genes in plants are described, for example, in US Patent Application Publication Number 2003/0037355.

3. Polypeptide-Based Inhibition of Protein Activity

In some embodiments of the invention, the polynucleotide encodes an antibody that binds to at least one MAPKKK polypeptide and reduces the MAPKKK activity of the MAPKKK polypeptide. In another embodiment, the binding of the antibody results in increased turnover of the antibody-MAPKKK polypeptide complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21 :35-36, incorporated herein by reference.

4. Gene Disruption

In some embodiments of the present invention, the activity of a MAPKKK polypeptide is reduced or eliminated by disrupting the gene encoding the MAPKKK polypeptide. The gene encoding the MAPKKK polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced MAPKKK activity.

i. Transposon Tagging

In one embodiment of the invention, transposon tagging is used to reduce or eliminate the MAPKKK activity of one or more MAPKKK polypeptides. Transposon tagging comprises inserting a transposon within an endogenous MAPKKK polypeptide gene to reduce or eliminate expression of the MAPKKK polypeptide. "MAPKKK gene" is intended to mean the gene that encodes a MAPKKK polypeptide according to the invention.

In this embodiment, the expression of one or more MAPKKK polypeptides is reduced or eliminated by inserting a transposon within a regulatory region or coding region of the gene encoding the MAPKKK polypeptide. A transposon that is within an exon, intron, 5' or 3' untranslated sequence, a promoter or any other regulatory sequence of a MAPKKK gene may be used to reduce or eliminate the expression and/or activity of the encoded MAPKKK polypeptide.

Methods for the transposon tagging of specific genes in plants are well known in the art. See, for example, Maes, et al., (1999) *Trends Plant Sci.* 5:90-96; Dharmapuri and Sonti, (1999) *FEMS Microbiol. Lett.* 179:53-59; Meissner, et al., (2000) *Plant J.* 22:265-275; Phogat, et al., (2000) *J. Biosci.* 25:57-63; Walbot, (2000) *Curr. Opin. Plant Biol.* 2:103-107; Gai, et al., (2000) *Nucleic Acids Res.* 28:95-96; Fitzmaurice, et al., (1999) *Genetics* 153:1919-1928). In addition, the TUSC process for selecting Mu insertions in selected genes has been described in Bensen, et al., (1995) *Plant Cell* 7:75-85; Mena, et al., (1996) *Science* 275:1537-1550 and US Patent Number 5,962,765.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 253: 572-581; Okubara, et al., (1995) *Genetics* 137:867-875 and Quesada, et al., (2000) *Genetics* 155:521-536. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:555-557.

Mutations that impact gene expression or that interfere with the function (MAPKKK activity) of the encoded protein are well known in the art. Insertional mutations in gene exons usually result in null-mutants. Mutations in conserved residues are particularly effective in inhibiting the MAPKKK activity of the encoded protein. Such mutants can be isolated according to well-known procedures, and mutations in different type A RR loci can be stacked by genetic crossing. See, for example, Gruis, et al., (2002) *Plant Cell* 15:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1555-1567.

The invention encompasses additional methods for reducing or eliminating the activity of one or more MAPKKK polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972 and 5,871,985. See also, WO 98/59350, WO 99/07865, WO 99/25821 and Beetham, et al., (1999) *Proc. Natl. Acad. Sci. USA* 96:8775-8778.

iii. Modulating the Stress Tolerance of a Plant Methods are provided for the use of the MAPKKK sequences of the invention to modulate the tolerance of a plant to abiotic stress. In specific embodiments, methods are provided to increase or maintain plant growth and development during abiotic stress episodes. During periods of stress (i.e., drought, salt, heavy metals, temperature extremes, etc.) plant development is often delayed or reduced. Modulating the level and/or activity of a MAPKKK sequence of the invention can maintain or improve plant growth, even under stress. Particularly vulnerable developmental periods include early seedling development and flowering. In one method, a MAPKKK nucleotide sequence is introduced into the plant and the level and/or activity of the MAPKKK polypeptide is modulated, thereby improving the tolerance of the plant to stress conditions and maintaining growth, which may be reflected in, for example, the rate of shoot growth, the extent of root development, the success of anthesis and seed set or the number or size of seed produced. Often the introduced MAPKKK nucleotide construct is stably incorporated into the genome of the plant and transmitted to progeny.

Methods to assay for a modulation in seed set during abiotic stress are known in the art. For example, plants having the modulated MAPKKK activity can be monitored under various stress conditions and compared to controls plants. For instance, the plant having the modulated MAPKKK activity and/or level can be subjected to various degrees of stress during flowering and seed set. Under identical conditions, the genetically modified plant having the modulated level and/or activity of MAPKKK polypeptide will have a higher number and/or mass of developing seed than a wild type (non-transformed) plant.

Accordingly, the present invention further provides plants having increased yield or a maintained yield during periods of abiotic stress (i.e. drought, salt, heavy metals, temperature extremes, etc). In some embodiments, the plants having an increased or maintained yield during abiotic stress have a modulated level/activity of a MAPKKK polypeptide of the invention. In other embodiments, the plant comprises a MAPKKK nucleotide sequence of the invention operably linked to a promoter that drives expression in the plant cell. In certain embodiments, such plants have stably incorporated into their genome a nucleic acid molecule comprising a MAPKKK nucleotide sequence of the invention operably linked to a promoter that drives expression in the plant cell.

iv. Modulating Shoot and Leaf Development

Methods are also provided for modulating shoot and leaf development in a plant. By "modulating shoot development" and/or "modulating leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompass all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10587-10592 and US Patent Application Publication Number 2003/0075698, each of which is herein incorporated by reference.

The method for modulating shoot and/or leaf development in a plant comprises modulating the activity and/or level of a MAPKKK polypeptide of the invention. In one embodiment, a MAPKKK sequence of the invention is provided. In other embodiments, the MAPKKK nucleotide sequence can be provided by introducing into the plant a polynucleotide comprising a MAPKKK nucleotide sequence of the invention, expressing the MAPKKK sequence and thereby modifying shoot and/or leaf development. In other embodiments, the MAPKKK nucleotide construct introduced into the plant is stably incorporated into the genome of the plant.

In specific embodiments, shoot and/or leaf development is modulated by modulating the level and/or activity of the MAPKKK in the plant. A modulation in MAPKKK activity can result in at least one or more of the following alterations in shoot and/leaf development including, but not limited to, altered (increased or decreased) shoot growth, altered photosynthesis, modulated leaf number, altered leaf surface, altered length of internodes and modulated leaf senescence. Modulating the level of the MAPKKK polypeptide in the plant can thereby increase plant yields.

As discussed above, one of skill will recognize the appropriate promoter to use to modulate shoot and leaf development of the plant. Exemplary promoters for this embodiment include constitutive promoters or promoters that are preferentially active in photosynthetic tissues including, for example, shoot-preferred promoters, shoot meristem-preferred promoters and leaf-preferred promoters. Exemplary promoters have been disclosed elsewhere herein.

Accordingly, the present invention further provides plants having a modulated shoot and/or leaf development when compared to a control plant. In some embodiments, the plant of the invention has an increased level/activity or a decreased level/activity of a MAPKKK polypeptide of the invention.

Methods for establishing callus from explants are known. For example, roots, stems, buds, immature embryos and aseptically germinated seedlings are just a few of the sources of tissue that can be used to induce callus formation. Generally, young and actively growing tissues (i.e. young leaves, roots, meristems) are used, but are not required. Callus formation is controlled by growth regulating substances present in the medium (auxins and cytokinins). The specific concentrations of plant regulators needed to induce callus formation vary from species to species and can even depend on the source of explant. In some instances, it is advised to use different growth substances (i.e. 2,5-D or NAA) or a combination of them during tests, since some species may not respond to a specific growth regulator. In addition, culture conditions (i.e. light, temperature, etc.) can also influence the establishment of callus. Once established, callus cultures can be used to initiate shoot regeneration. See, for example, Gurel, et al., (2001) *Turk J. Bot.* 25:25-33; Dodds, et al., (1995). Experiments in Plant Tissue Culture, Cambridge University Press; Gamborg (1995) *Plant Cell, Tissue and Organ Culture*, eds. Phillips and US Patent Application Publication Number 2003/0180952, all of which are herein incorporated by reference.

It is further recognized that increasing seed size and/or weight can be accompanied by an increase in the rate of growth of seedlings or an increase in early vigor. In addition, modulating the plant's tolerance to stress, as discussed above, along with modulation of root, shoot and leaf development can increase plant yield and vigor. As used herein, the term "vigor" refers to the relative health, productivity and rate of growth of the plant and/or of certain plant parts, and may be reflected in one or more various developmental attributes, such as concentration of chlorophyll, photosynthetic rate, total biomass and root biomass. Of particular relevance is the ability of a plant to grow rapidly during early development, and relates to the successful establishment, after germination, of a well-developed root system and a well-developed photosynthetic apparatus. Improvements in vigor are measured with reference to a control as defined elsewhere herein.

v. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development or radial expansion.

The methods for modulating root development comprise modulating (reducing or increasing) the level and/or activity of the MAPKKK polypeptide in the plant. In one method, a MAPKKK nucleotide sequence is introduced into the plant and the level and/or activity of the MAPKKK polypeptide is modulated. In other methods, the MAPKKK nucleotide construct introduced into the plant is stably incorporated into the genome of the plant.

A modulation in MAPKKK activity can result in at least one or more of the following alterations to root development, including, but not limited to, larger root meristems, increased root growth, enhanced radial expansion, an enhanced vasculature system, increased root branching, more adventitious roots and/or increased fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc. Methods of measuring such developmental alterations in the root system are known in the art. See, for example, US Patent Application Publication Number 2003/0075698 and Werner, et al., (2001) *PNAS* 18:10587-10592, both of which are herein incorporated by reference.

As discussed above, one of skill will recognize the appropriate promoter to use to modulate root development in the plant. Exemplary promoters for this embodiment include root-preferred promoters, which have been disclosed elsewhere herein.

Stimulating root growth and increasing root mass by modulating the activity and/or level of the polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by modulating the level and/or activity of the MAPKKK polypeptide also finds use in promoting in vitro propagation of explants.

Accordingly, the present invention further provides plants having modulated root development when compared to the root development of a control plant. In some embodiments, the plant of the invention has a modulated level/activity of the MAPKKK polypeptide of the invention and has enhanced root growth and/or root biomass. In other embodiments, such plants have stably incorporated into their genome a nucleic acid molecule comprising a MAPKKK nucleotide sequence of the invention operably linked to a root-preferred promoter that drives expression in the plant cell, wherein expression of the sequence modulates the level and/or activity of the MAPKKK polypeptide.

The following examples are offered by way of illustration and not by way of limitation.

EXAMPLES

Example 1

Maize Transformation with the Sequences of the Invention

Immature maize embryos from greenhouse donor plants are bombarded with a plasmid containing an expression cassette MAPKKK, as detailed in methods described elsewhere herein. The MAPKKK polynucleotide is operably linked to a MAPKKK—promoter and the selectable marker gene PAT (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

The ears are husked and surface sterilized in 30% Clorox® bleach plus 0.5% Micro detergent for 20 minutes, and rinsed two times with sterile water. The immature embryos are excised and placed embryo axis side down (scutellum side up), 25 embryos per plate, on 560Y medium for 5 hours and then aligned within the 2.5 cm target zone in preparation for bombardment.

A plasmid vector comprising the maize RR5 sequence operably linked to a *Zea mays* RAB17 promoter is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$ and 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #5 in particle gun #HE35-1 or #HE35-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-5 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored under various stress conditions and compared to control plants. Alterations in phenotype, such as improved tolerance to stress, will be monitored.

Bombardment medium (560Y) comprises 5.0 g/l N6 basal salts (SIGMA C-1516), 1.0 ml/l Eriksson's Vitamin Mix (1000× SIGMA-1511), 0.5 mg/l thiamine HCl, 120.0 g/l sucrose, 1.0 mg/l 2,5-D and 2.88 g/l L-proline (brought to volume with D-I $H_2O$ following adjustment to pH 5.8 with KOH); 2.0 g/l Gelrite® (added after bringing to volume with D-I $H_2O$); and 8.5 mg/l silver nitrate (added after sterilizing the medium and cooling to room temperature). Selection medium (560R) comprises 5.0 g/l N6 basal salts (SIGMA C-1516), 1.0 ml/l Eriksson's Vitamin Mix (1000× SIGMA-1511), 0.5 mg/l thiamine HCl, 30.0 g/l sucrose and 2.0 mg/l 2,5-D (brought to volume with D-I $H_2O$ following adjustment to pH 5.8 with KOH); 3.0 g/l Gelrite® (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 5.3 g/l MS salts (GIBCO 11117-075), 5.0 ml/l MS vitamins stock solution (0.100 g nicotinic acid, 0.02 g/l thiamine HCL, 0.10 g/l pyridoxine HCL and 0.50 g/l glycine brought to volume with polished D-I $H_2O$) (Murashige and Skoog, (1962) *Physiol. Plant.* 15:573),100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite® (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 5.3 g/l MS salts (GIBCO 11117-075), 5.0 ml/l MS vitamins stock solution (0.100 g/l nicotinic acid, 0.02 g/l thiamine HCL, 0.10 g/l pyridoxine HCL and 0.50 g/l glycine brought to volume with polished D-I $H_2O$), 0.1 g/l myo-inositol and 50.0 g/l sucrose (brought to volume with polished D-I $H_2O$ after adjusting pH to 5.6) and 6 g/l Bacto™-agar solidifying agent (added after bringing to volume with polished D-I $H_2O$), sterilized and cooled to 60° C.

Example 2

Modulating Plant Yields

For *Agrobacterium*-mediated transformation of maize with the MAPKKK nucleotide sequence (SEQ ID NO: 1, 4, 7 or 9) operably linked to a *Zea mays* ubiquitin promoter, or a stress-inducible promoter, the method of Zhao is employed (U.S. Pat. No. 5,981,850 and PCT Patent Publication Number WO098/32326; the contents of which are hereby incorporated by reference). Briefly, immature embryos are isolated from maize and the embryos contacted with a suspension of *Agrobacterium*, where the bacteria are capable of transferring the MAPKKK nucleotide sequence to at least one cell of at least one of the immature embryos (step 1: the infection step). In this step the immature embryos are immersed in an Agrobacterium suspension for the initiation of inoculation. The embryos are co-cultured for a time with the Agrobacterium (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 5: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

The plants are monitored for a modulation in shoot growth, leaf senescence, and/or photosynthesis when compared to an appropriate control plant. A modulation in plant yield is also monitored.

Example 3

Soybean Transformation

Soybean embryos are bombarded with a plasmid containing the MAPKKK sequence operably linked to a *Zea mays* ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 5,955,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette comprising the MAPKKK operably linked to the *Zea mays* ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 500 µl 70% ethanol and resuspended in 50 µl of anhydrous ethanol. The DNA/particle suspension can be sonicated three times for one second each. Five microliters of the DNA-coated gold particles are then loaded on each macro carrier disk.

Approximately 300-500 mg of a two-week-old suspension culture is placed in an empty 60x15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 4

Sunflower Meristem Tissue Transformation

Sunflower meristem tissues are transformed with an expression cassette containing the MAPKKK (SEQ ID NO: 1, 4, 7 or 9) operably linked to a *Zea mays* ubiquitin promoter or a stress-inducible promoter as follows (see also, European Patent Number EP 0 586233, herein incorporated by reference and Malone-Schoneberg, et al., (1995) *Plant Science* 103:199-207). Mature sunflower seed (*Helianthus annuus L.*) are dehulled using a single wheat-head thresher. Seeds are surface sterilized for 30 minutes in a 20% Clorox® bleach solution with the addition of two drops of Tween20® per 50 ml of solution. The seeds are rinsed twice with sterile distilled water.

Split embryonic axis explants are prepared by a modification of procedures described by Schrammeijer, et al., (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.*, 15:573-597), Shepard's vitamin additions (Shepard, (1980) in *Emergent Techniques for the Genetic Improvement of Crops* (University of Minnesota Press, St. Paul, Minn.), 50 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60x20 mm plate for this treatment. Approximately 5.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the RR6 gene operably linked to the Zea mays ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bacto®peptone and 5 gm/l NaCl, pH 7.0) with the appropriate antibiotics required for bacterial strain and binary plasmid maintenance. The suspension is used when it reaches an $OD_{600}$ of about 0.5 to 0.8. The *Agrobacterium* cells are pelleted and resuspended at a final $OD_{600}$ of 0.5 in an inoculation medium comprised of 12.5 mM MES pH 5.7, 1 gm/l $NH_5Cl$, and 0.3 gm/l $MgSO_5$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 375B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 375B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for MAPKKK activity.

NPTII-positive shoots are grafted to PIONEER® hybrid 6550 in vitro-grown sunflower seedling rootstock. Surface sterilized seeds are germinated in 58-0 medium (half-strength Murashige and Skoog salts, 0.5% sucrose, 0.3% Gelrite® pH 5.6) and grown under conditions described for explant culture. The upper portion of the seedling is removed, a 1 cm vertical slice is made in the hypocotyl, and the transformed shoot inserted into the cut. The entire area is wrapped with PARA film® to secure the shoot. Grafted plants can be transferred to soil following one week of in vitro culture. Grafts in soil are maintained under high humidity conditions followed by a slow acclimatization to the greenhouse environment. Transformed sectors of To plants (parental generation) maturing in the greenhouse are identified by NPTII ELISA and/or by MAPKKK activity analysis of leaf extracts while transgenic seeds harvested from NPTII-positive To plants are identified by MAPKKK activity analysis of small portions of dry seed cotyledon.

Example 5

Rice Transformation

One method for transforming DNA into cells of higher plants that is available to those skilled in the art is high-velocity ballistic bombardment using metal particles coated with the nucleic acid constructs of interest (see, Klein, et al., (1987) *Nature* (London) 327:70-73 and see, U.S. Pat. No. 4,945,050). A Biolistic PDS-1000/He (BioRAD Laboratories, Hercules, Calif.) is used for these complementation experiments.

The bacterial hygromycin B phosphotransferase (Hpt II) gene from *Streptomyces hygroscopicus* that confers resistance to the antibiotic may be used as the selectable marker for rice transformation. In the vector, the Hpt II gene may be engineered with the 35S promoter from Cauliflower Mosaic Virus and the termination and polyadenylation signals from the octopine synthase gene of Agrobacterium tumefaciens. For example, see the description of vector pML18 in WO97/47731, published on Dec. 18, 1997, the disclosure of which is hereby incorporated by reference.

Embryogenic callus cultures derived from the scutellum of germinating rice seeds serve as source material for transformation experiments. This material is generated by germinating sterile rice seeds on a callus initiation media (MS salts, Nitsch and Nitsch vitamins, 1.0 mg/l 2,4-D and 10 µM $AgNO_3$) in the dark at 27-28° C. Embryogenic callus proliferating from the scutellum of the embryos is transferred to CM media (N6 salts, Nitsch and Nitsch vitamins, 1 mg/l 2,4-D, Chu, et al., (1985) *Sci. Sinica* 18:659-668). Callus cultures are maintained on CM by routine sub-culture at two-week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman® #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate.

Each genomic DNA fragment is co-precipitated with pML18 (containing the selectable marker for rice transformation) onto the surface of gold particles. To accomplish this, a total of 10 µg of DNA at a 2:1 ratio of trait:selectable marker DNAs are added to 50 µl aliquot of gold particles that have been resuspended at a concentration of 60 mg $ml^{-1}$. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are washed twice with 1 ml of absolute ethanol and then resuspended in 50 µl of absolute ethanol and sonicated (bath sonicator) for one second to disperse the gold particles. The gold suspension is incubated at −70° C. for five minutes and sonicated (bath sonicator) if needed to disperse the particles. Six µl of the DNA-coated gold particles are then loaded onto Mylar® macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Two to four plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipette. Three ml aliquots of the callus suspension are plated onto fresh SM media and the plates are incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% Gelrite®+50 ppm hyg B) for 2 weeks in the dark at 25° C. After 2 weeks the callus is transferred to RM2 media (MS salts, Nitsch and Nitsch vitamins, 3% sucrose, 0.4% Gelrite®+50 ppm hyg B) and placed under cool white light (~40 $\mu Em^{-2}s^{-1}$) with a 12 hr photoperiod at 25° C. and 30-40% humidity. After 2-4 weeks in the light, callus begin to organize and form shoots. Shoots are removed from surrounding callus/media and gently transferred to RM3 media (½×MS salts, Nitsch and Nitsch vitamins, 1% sucrose+50 ppm hygromycin B) in PHYTATRAY™ disposable plant cell culture vessels (Sigma Chemical Co., St. Louis, Mo.) and incubation is continued using the same conditions as described in the previous step.

Plants are transferred from RM3 to 4″ pots containing Metro mix 350 after 2-3 weeks, when sufficient root and shoot growth have occurred.

Example 6

Variants of MAPKKK

A. Variant Nucleotide Sequences of MAPKKK (SEQ ID NOS: 1, 4, 7, 9) That Do Not Alter the Encoded Amino Acid Sequence The MAPKKK nucleotide sequences set forth in SEQ ID NOS: 1, 4, 7, 9 may be used to generate variant nucleotide sequences having 0%, 75%, 80%, 81%, 82%, 83%, 84%, 85%, 86%, 87%, 88%, 89%, 90%, 91%, 92%, 93%, 94%, 95%, 96%, 97%, 98% or 99% nucleotide sequence identity when compared to the starting unaltered ORF nucleotide sequence of SEQ ID NOS:1, 4, 7, 9. These functional variants are generated using a standard codon table. While the nucleotide sequence of the variant is altered, the amino acid sequence encoded by the open reading frame does not change.

B. Variant Amino Acid Sequences of MAPKKK

Variant amino acid sequences of MAPKKK may be generated. In this example, one amino acid may be altered. Specifically, the sequences set forth in SEQ ID NO: 2, 5, 8 or 10 may be reviewed to determine the appropriate amino acid alteration. The selection of the amino acid to change may be made by consulting the protein alignment. See, FIG. 2. An amino acid may be selected that is deemed not to be under high selection pressure (not highly conserved) and which is rather easily substituted by an amino acid with similar chemical characteristics (i.e., similar functional side-chain). Using the protein alignment set forth in FIG. 2 an appropriate amino acid can be changed. Amino acid residues that show a low percentage of sequence identity among the *Zea mays* MAPKKK proteins are not highlighted. Additional conserved residues can be found in FIG. 2. Once the targeted amino acid is identified, the procedure outlined in Example 5A is followed. Variants having about 70%, 75%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NOS: 2, 5, 8 or 10 may be generated using this method.

C. Additional Variant Amino Acid Sequences of MAPKKK

In this example, artificial protein sequences are created having 70%, 75%, 80%, 81%, 82%, 83%, 84%, 85%, 86%, 87%, 88%, 89%, 90%, 91%, 92%, 93%, 94%, 95%, 96%, 97%, 98% or 99% identity relative to the reference protein sequence. This latter effort requires identifying conserved and variable regions from the alignment set forth in FIG. 2 and then the judicious application of an amino acid substitutions table. These parts will be discussed in more detail below.

Largely, the determination of which amino acid sequences may be altered is made based on the conserved regions among MAPKKK proteins. See, FIG. 2. Based on the sequence alignment, the various regions of the MAPKKK that can likely be altered can be determined. It is recognized that conservative substitutions can be made in the conserved regions without altering function. In addition, one of skill will understand that functional variants of the MAPKKK sequences of the invention may also have minor amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 2.

TABLE 2

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 5 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 15 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acid in the protein that should not be changed is identified and "marked off" for insulation from the substitution. The start methionine will of course be added to this list automatically. Next, the changes are made.

H, C and P are not changed in any circumstance. The changes will occur with isoleucine first, sweeping N-terminal to C-terminal; then leucine and so on down the list until the desired target is reached. Interim number substitutions can be made so as not to cause reversal of changes. The list is ordered 1-17, so as many isoleucine changes are made as needed before leucine and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of MAPKKK are generated having about 70%, 75%, 80%, 81%, 82%, 83%, 84%, 85%, 86%, 87%, 88%, 89%, 90%, 91%, 92%, 93%, 94%, 95%, 96%, 97%, 98% or 99% amino acid identity to the starting unaltered ORF sequence of SEQ ID NO: 3 or 6.

Example 7

Identification of the maize NPK1-related sequences

A maize MAPKKK that was orthologous to the rice NPK1-like gene (dbj|BAB64165.1| (AP003254) NPK1-related protein kinase-like protein [Oryza sativa] E=0.094 [5'(1),3'(0) PCL253028(1) cds3f.pk005.d19) was first identified from two expression profiling Agilent experiments, namely, 'Cold-induced gene expression in B73 seedling shoots with time of exposure to low-temperature stress', and 'Stress-induced gene expression in CML349 seedling shoots with time of exposure to stress'.

The objective of these experiments was to develop a picture of the changing gene expression pattern under increasing times of exposure to dehydration stress, applied in the form of low-temperature stress. The first experiment involved growing of B73 seedlings for 14 days from planting, followed by imposition of a cold stress of 10° C., and then collecting the entire shoot tissue above the coleoptile at 0 h, 0.5 h, 1 h, 4 h, 8 h and 24 h of exposure to low temperature and also after 48 h of recovery at 25° C. following the last low-temperature stress treatment, namely, 24 h of cold stress. Pairwise comparisons were made to determine the nature of gene-expression changes at each time-point after exposure to cold, relative to the zero time control. This experiment gave an understanding of the timed induction of various genes and pathways in B73 that were turned on from the early to the later times of exposure to cold stress. It also helped to identify candidate genes and promoters for both drought and cold, by (1) determining if the genes with critical induction behavior under cold stress were reported in the literature as having relevance to drought stress and (2) if the expression of the genes with critical induction behavior under cold stress showed drought or stress-hormone (ABA, ethylene) related induction in Lynx MPSS experiments.

The above experiment was repeated using CML349 in place of B73. CML349 is a tropical highland maize line from CIMMYT that is known to have improved tolerance to cold temperatures. Following the second experiment, comparisons were made between timed induction of genes in CML349, the Mexican highland line that has tolerance to cold, and B73, the corn-belt dent line that has less tolerance to cold than CML349.

A maize EST with homology to a rice NPK1-like kinase exhibited an interesting behavior in these gene-expression profiling experiments. We found that the maize EST, cds3f.pk005.d19, showed highest expression levels at the early time point of 1 hour after cold exposure in CML349, while it was not induced to the same extent in B73 (Table 3, FIG. 1). The intensities of Agilent expression indicated that B73 had high expression levels of the gene under normal temperatures, which was further increased two-fold 4 h following exposure to cold-temperature stress. CML349, on the other hand, had low levels of expression of this gene under normal temperatures, but was induced almost 36-fold very early (1 h) after exposure to the cold stress. The induced level at the early time point of 1 h after stress exposure was greater than the level in B73 at the same time point, and also greater than the induced level in B73 4 h after exposure to stress. Our previous experiments with protein profiling (collaboration with Oxford GlycoSciences) had shown that the protein levels of several genes involved in combating oxidative stress were either normally high or induced to higher levels in CML349 relative to B73. This is consistent with reported action of the *Arabidopsis* ortholog of NPK1, namely ANP1, which itself is induced by hydrogen peroxide mimicking oxidative stress, and which when constitutively active increased the promoter activity of specific stress-responsive genes including GST6 (Kovtun, et al., (2000) *Proc Natl Acad Sci* 97:2940-2945).

TABLE 3

Stress-induced expression levels of ZmNPK1b in B73 and CML349.

| Time after stress exposure | B73 | | CML349 | |
| --- | --- | --- | --- | --- |
| | Intensity 1 (0 h) | Intensity 2 | Intensity 1 (0 h) | Intensity 2 |
| 0.5 h at 10° C. | 1247.9409 | 1030.0294 | 242.1342 | 645.7405 |
| 1 h at 10° C. | 1103.7903 | 2178.2920 | 110.8528 | 4462.0635 |
| 4 h at 10° C. | 1485.4978 | 3222.3875 | 117.6474 | 251.4074 |
| 8 h at 10° C. | 1205.4165 | 1020.0490 | 84.3675 | 124.7931 |
| 24 h at 10° C. | 1398.2936 | 1198.3543 | 219.4813 | 207.8984 |
| 48 h Recovery | 2025.9680 | 319.3025 | 399.1231 | 309.4664 |

ZmNPK1b expression levels in B73 and CML349 at different time periods after exposure to low-temperature stress, as measured by color intensity in microarray analysis (Agilent Technologies, Santa Clara, CA).
Intensity 2 denotes the gene expression at any given time point after exposure to stress.

Example 8

Isolation of the Maize NPK1-Related Sequences

Upon full-insert sequencing of EST cds3f.pk005.d19, it was revealed that it contained a partial clone. The sequence of cds3f.pk005.d19 was used in two ways to obtain full sequence of NPK1.

First, blast searches were done for homologs of the cds3f.pk005.d19 partial sequence against PHI contigs. Based on the results, PCO527001 (UC5.1) or PCO644860 (UC6.0) was identified as a close homolog and a representative EST, ctst1s.pk017.e17 was submitted to full-insert sequencing and subsequently found to be full-length.

The sequence of cds3f.pk005.d19 was also used for BAC-library screening. A BAC clone was identified (bacb.pk191.e03) and sequenced. Coding sequence information pieced together from genomic information in the BAC sequence was used to PCR out the full coding sequence (CDS). The full CDS sequence is represented in PCO0644861 (Top Blast UPI00000AA4AE NPK1-related protein kinase-like protein [Oryza sativa (japonica cultivar-group)] E=0.0 (Reference Proteins MAR-31-2006) [Members=20, ORFCode=5NOCXX] UC6.0). Consequently, full-insert sequencing of several component ESTs was requested and completed. Primers as set forth in SEQ ID NO: 12 and 13 were used to amplify Zm NPK1b complementary DNA sequence from the BAC clone, p1.bacb.pk191.e03.

The rice NPK1-related protein kinase that is identified as being orthologous to ctst1s.pk017.e17 (PCO644860) is NP_917080, and that homologous to cds3f.pk005.d19 (PCO644861) is NP_917084/BAB64165.1. The maize NPK1 sequence derived from the former was named ZmNPK1a and that from the latter was named ZmNPK1b.

Subsequent searches were done using the tobacco NPK1 protein to identify rice sequences in the public domain with the closest homology and this yielded the rice protein BAF24980. The rice protein had 57.5% consensus and 48.2% identity with the tobacco protein. The rice protein was used to search Unicorn 6.0 and this search identified the closest maize ortholog to be PCO622918. This sequence is partial with an incomplete 5' end and was named ZmNPK1c. In addition, while checking possible map location, it was identified that ZmNPK1a co-localized with an NPK1-related kinase represented by PCO638212, which was named ZmNPK1d. Sequence information for ZmNPK1a, ZmNPK1b, ZmNPK1c and ZmNPK1d are provided as SEQ ID NOS: 1-3, 4-6, 7-8, and 9-11, respectively.

Example 9

Chromosome Localization, Expression Information and Cell Specificity of the Identified Sequences:

The contigs pertinent to ZmNPK1a, ZmNPK1b, ZmNPK1c and ZmNPK1d (PCO644860, PCO644861, PCO622918 and PCO638212 respectively) were checked for possible chromosomal position using BLAST searches against public and proprietary BAC sequences. ZmNPK1a (PCO644860), ZmNPK1b (PCO644861) and ZmNPK1d (PCO638212) were located to chromosome 3, while ZmNPK1c was located to chromosome 2. ZmNPK1a and ZmNPK1d were found to be potentially associated with QTL for the Staygreen phenotype with a proprietary association tool. With this same tool it was observed that ZmNPK1c (PCO622918) shows potential association with yield QTLs and also with the drought QTLs for Anthesis Silking Interval, Staygreen and Barrencount. It should be noted that the proprietary association tool uses the proprietary QTL data that involves low-resolution phenotypic associations to chromosomal regions that may be as large as 75 cM for some traits. Accordingly, associations presented here do not verify that a specific gene is controlling these traits, rather they suggest which trait associations exist for consideration.

The native expression of all four sequences was analyzed in Lynx MPSS libraries. The expression of ZmNPK1a was found to be high in stalk and root tissue, with the highest expression of 204 ppm observed in pulvinus tissue of B73 stalks. Expression of ZmNPK1b was found to be high in kernel and root tissue, with the highest expression of 984 ppm in maize kernels at 0 days after pollination, closely followed by 928 ppm in maize primary roots. ZmNPK1c had very little representation in the Lynx libraries and thus has extremely low expression levels of the gene. Finally, the expression of ZmNPK1d was uniformly distributed in all tissues, the highest being 263 ppm in maize kernels at 0 days after pollination.

Cellular localization of all four sequences was checked scanning the protein sequences for typical target peptides using the commercially or publicly available research tools of TargetP, ChloroP, SIGNALP and PSORT. (Emanuelsson et al. (2007) Nature Protocols 2:953-971; Nakai and Horton (1999) Trends Biochem. Sci. 24(1):34-36) The results indicated that ZmNPK1a, ZmNPK1b and ZmNPK1d localize to the mitochondria in the plant cell. The localization for ZmNPK1c could not be predicted with any degree of confidence, likely due to its incomplete N-terminal region.

Example 10

Induction of Native MAPKKKs by Stress or Hormone Treatments

Stress-induced expression profiling of maize genes was conducted using Massively Parallel Signature Sequencing in Lynx (MPSS™) (see, Brenner, et al., (2000) Nature Biotechnology 18:630-634, Brenner, et al., (2000) Proc Natl Acad Sci USA 97:1665-1670).

Maize hybrid 3245 was subjected to a severe water stress aimed to reduce yield by approximately 55-70% relative to the same hybrid under well-watered conditions. The stress treatment was imposed 5 weeks prior to anthesis, at about 650-700 GDU (growing-degree units), and continued for 2 weeks or over 300 GDU, post-anthesis. Each plot contained 4 rows of plants. During this stress period, samples were collected from ear leaves, immature ears at first silk and ear-base and ear-tip kernels at seven days after pollination, in both the well-watered and drought-stressed treatments. Samples were ground under liquid nitrogen, RNA extracted and subjected to expression profiling.

For cold-stress induction studies, maize seedlings of the inbred B73 or CML349 were germinated and grown under optimum temperature conditions in the greenhouse. Leaves of ten-day-old seedlings constituted the sample material. The experiment included three treatments, namely, control or optimum temperature, chilling treatment and recovery from freezing. Control seedlings that did not receive any cold stress were moved to a growth chamber maintained at the same temperature regime as the greenhouse, while seedlings intended for the chilling treatment were moved to a growth chamber maintained at 10° C. Seedlings intended for recovery from freezing were subjected to −2° C. for 2 hours and then allowed to recover at optimal temperature for 6 hours. Chilling and recovery from freezing were continued for a period of 6 hours. All three treatments were harvested at the end of the required time period, ground in liquid nitrogen and subjected to RNA extraction followed by expression profiling.

For hormone-induction studies, maize seedlings of the inbred B73 were grown in the greenhouse up to the V5 stage. At this time, the plants were treated with 0.1 mM ABA (abscisic acid) or 1 mM Ethephon plant growth regulator. Leaves from six plants thus treated were harvested at 0, 24 and 48 hours of ABA or Ethephon treatment, ground in liquid nitrogen, and subjected to RNA extraction followed by expression profiling. The plants harvested at 0 h of hormone treatment constituted the control.

As indicated in Table 4, ZmNPK1b and ZmNPK1d were found to be specifically induced by drought stress and treatment with the stress hormones ABA and ethylene. ZmNPK1b was induced by chilling.

TABLE 4

Stress-related expression of ZmNPK1b and ZmNPK1d in Lynx MPSS libraries.

| Name | PPM | Tissue | Genotype | Treatment |
|---|---|---|---|---|
| Stress-related expression of ZmNPK1b in Lynx MPSS libraries (Tag: GATCAGCGGATGCTTCG) | | | | |
| Cla24lm-sig | 104 | leaf | B73 | Corn, B73, v5 ABA treated leaves, 24 hr |
| Cla48lm-sig | 38 | leaf | B73 | Corn, B73, v5 ABA treated leaves, 48 hr |
| Cle24lm-sig | 55 | leaf | B73 | Corn, B73, v5 Ethephon treated leaves, 24 hr |
| Cle48lm-sig | 45 | leaf | B73 | Corn, B73, v5 Ethephon treated leaves, 48 hr |
| Cl0lm-sig | 0 | leaf | B73 | Corn, B73, v5 leaves |

TABLE 4-continued

Stress-related expression of ZmNPK1b and ZmNPK1d in Lynx MPSS libraries.

| Name | PPM | Tissue | Genotype | Treatment |
|---|---|---|---|---|
| Cktsslm-sig | 34 | seed | 3245 | Seed, 3245, drought stressed 7-DAP Apical Kernels |
| Ckbsslm-sig | 108 | seed | 3245 | Seed, 3245, drought stressed 7-DAP Basal Kernels |
| Cktwwlm-sig | 7 | seed | 3245 | Seed, 3245, well-watered 7-DAP Apical Kernels |
| Ckbwwlm-sig | 0 | seed | 3245 | Seed, 3245, well-watered 7-DAP Basal Kernels |
| Csdl1lm-chil | 88 | seedling | B73 | seedling subjected to chilling treatment at 10° C. |
| Csdl1lm-ctr | 8 | seedling | B73 | seedling, control |
| Stress-related expression of ZmNPK1d in Lynx MPSS libraries (Tag: GATCCCGGGTGTTGTGT) | | | | |
| Cla24lm-sig | 99 | leaf | B73 | Corn, B73, v5 ABA treated leaves, 24 hr |
| Cla48lm-sig | 205 | leaf | B73 | Corn, B73, v5 ABA treated leaves, 48 hr |
| Cle24lm-sig | 75 | leaf | B73 | Corn, B73, v5 Ethephon treated leaves, 24 hr |
| Cle48lm-sig | 19 | leaf | B73 | Corn, B73, v5 Ethephon treated leaves, 48 hr |
| Cl0lm-sig | 52 | leaf | B73 | Corn, B73, v5 leaves |
| Cktsslm-sig | 114 | seed | 3245 | Seed, 3245, drought stressed 7-DAP Apical Kernels |
| Ckbsslm-sig | 29 | seed | 3245 | Seed, 3245, drought stressed 7-DAP Basal Kernels |
| Cktwwlm-sig | 74 | seed | 3245 | Seed, 3245, well watered 7-DAP Apical Kernels |
| Ckbwwlm-sig | 155 | seed | 3245 | Seed, 3245, well watered 7-DAP Basal Kernels |
| Csdl1lm-chil | 16 | seedling | B73 | seedling subjected to chilling treatment at 10° C. |
| Csdl1lm-fro | 39 | seedling | B73 | seedling recovering from freezing treatment at −2° C. |

Example 11

Stress-Induced Expression of Transgenic MAPKKKs

The sequence of ZmNPK1a was incorporated into the maize transformation vector PHP29013 (RAB17::ZmNPK1a+RAB17::ZmCBF1) to test for efficacy under abiotic stress. Additional constructs have been made, as follows: RAB17::ZmNPK1b (PHP32420); RD29A::ZmNPK1a (PHP32647); RD29A::ZmNPK1b (PHP32984) and ZmEEP5::ZmNPK1a (PHP36818).

As previously indicated, the RAB17 and RD29A promoters are stress-induced. To test stress-induced expression of the MAPKKK transgenes, T1 plants comprising the RAB17::ZmNPK1b, RD29A::ZmNPK1a or RD29A::ZmNPK1b construct were grown under drought stress in the greenhouse, as described in Example 12. Leaf punches were taken from individual plants and stored at −80° C. for RNA extraction using the RNeasy 96 Kit from QIAGEN, Inc. (Valencia, Calif.). The cDNA was produced from total RNA using the QuantiTect Reverse Transcription Kit from QIAGEN as directed by the manufacturer and expression of the transgene of interest was analyzed by Q-PCR. Events of all three constructs have shown stress-inducible expression. Field testing under drought conditions is further used to evaluate effect of each of the transgenes. Field evaluation will include assessment for vivipary, which may be associated with use of rab17 and is generally an undesirable trait.

Example 12

Testing of Transgenic Plants Under Stress Conditions

Transgenic plants, for example those created using the methods of Example 1 or 2, expressing a recombinant MAPKKK of the present invention, may be subjected to artificial environments to simulate abiotic stresses, for example, cold, drought or limited water conditions, a combination of drought and heat, or salinity stress. Prior to applying the stress, plants are established in controlled growing conditions, as follows:

Nutrient Solution: Nutrient solution is prepared using a 20:10:20 NPK fertilizer mix, at a concentration of 3.7 ounces per 5 gallons of water. This stock solution is further diluted to $\frac{1}{16}^{th}$ concentration with water and applied to plants.

It is useful to add half a teaspoon of Osmocote® (NPK 15:9:12) to the pot at the time of transplanting or after emergence (The Scotts Miracle-Gro Company, Ohio, USA).

Border plants: Place a row of border plants on bench-edges adjacent to the glass walls of the greenhouse or adjacent to other potential causes of microenvironment variability such as a cooler fan.

Automation: Watering can be done using PVC pipes with drilled holes to supply water to systematically positioned pots using a siphoning device. Irrigation scheduling can be done using timers.

Replications: Eight to ten individual plants are used per treatment per event.

Following treatment and data collection, mean values for plant size, color and chlorophyll fluorescence recorded on transgenic events under different stress treatments are exported to Spotfire (Spotfire, Inc., MA, USA). Treatment means are evaluated using Analysis of Variance.

A. Low-temperature Tolerance

To demonstrate whether expression of MAPKKKs of the present invention can confer increased germination ability under cool conditions, transgenic seeds expressing a MAPKKK polypeptide of the present invention may be germinated under conditions similar to the standard cold germination tests used in the seed industry. Alternatively, transgenic seeds expressing such a MAPKKK may be planted under seed bed conditions made cool by artificial environments or naturally cool seed beds in the field. Additionally, plants expressing the MAPKKK may be challenged during the seed development period by cool night time temperatures to demonstrate decreased inhibition of leaf or canopy activity as a result of cold stress during this time of crop development.

Young transgenic seedlings may be grown at a low temperature, such as about 13° C., during the light and 13° C. during the dark period. Plant seeds in 96-pod flats containing greenhouse soil medium. Water initially with Seplex (Blackmore Company, Belleville, Mich.) water for the first day after planting and germinate seedlings in the greenhouse. After the initial watering, continue watering seedlings with 85 ppm 20:10:20 fertilizer water. Once plants reach the V3 stage (approximately 10-14 days), move them to a growth chamber and subject to a chilling regimen of 16/8 hour light/dark cycle, where day/night temperatures are maintained at 15° C. light/13° C. dark, under constant humidity. The pots should be placed in flats that do not have the slit openings in the flats.

Bottom water the seedlings with 85 ppm 20:10:20 fertilizer water, keeping the seedlings well-watered. Subject seedlings to chilling conditions for the next 16 days. Score for visual yellowing at 4, 8, 12 and 16 days into the stress period and also record chlorophyll fluorescence using the Hansatech FMS2 chlorophyll fluorescence meter (Hansatech Instruments Ltd). Leaf discs can be used to determine ROS (reactive oxygen species) accumulation due to photo-oxidative damage under low temperature combined with high light. At the end of the stress period, harvest plants at soil level and record fresh weight or biomass accumulation. Inclusion of check varieties that are tolerant and susceptible to low temperature growth is important for normalization of observations across experiments. Tolerance of the transgenic plant to the stress may be assessed on the basis of increased plant growth, fresh or dry weight of the seedlings and/or increased photosynthetic activity or chlorophyll fluorescence in the transgenic plant relative to control non-transgenic plants. Physical characteristics of the transgenic and control plants' growth may be assessed as described herein.

Transgenic plants expressing a MAPKKK of the present invention may also be assayed for increased freezing tolerance at the seedling stage as well as late season periods. These assays are preferably done in artificial environments to simulate frost or freeze events. In addition, transgenic seeds may be planted outside during times when the natural environment would impose the stress, e.g., at times when frost is present.

B. Drought Tolerance

Transgenic plants expressing a MAPKKK of the present invention may also be assayed in artificial drought-stress environments in pot-based studies or under managed drought-stress conditions in the field in order to demonstrate that the transgene confers resistance or tolerance to drought. Transgenic maize seedlings containing the candidate gene can be screened for tolerance to drought stress by a pot-based screen in the following manner. Transgenic maize plants are subjected to well-watered conditions (control) and to drought-stressed conditions. Transgenic maize plants are screened at the T1 generation or later. Stress is imposed starting at 10 to 14 days after sowing (DAS) or 7 days after transplanting, and is continued through to silking. Pots are watered by an automated system fitted to timers to provide watering at 25 or 50% of field capacity during the entire period of drought-stress treatment. The intensity and duration of this stress will allow identification of the impact on vegetative growth as well as on the anthesis-silking interval (ASI).

Potting mixture: A mixture of ⅓ turface (Profile Products LLC, IL, USA), ⅓ sand and ⅓ SB300 (Sun Gro Horticulture, WA, USA) can be used. The SB300 can be replaced with Fafard Fine-Germ (Conrad Fafard, Inc., MA, USA) and the proportion of sand in the mixture can be reduced. Thus, a final potting mixture can be ⅜ (37.5%) turface, ⅜ (37.5%) Fafard and ¼ (25%) sand.

Field Capacity Determination: The weight of the soil mixture (w1) to be used in one S200 pot (minus the pot weight) is measured. If all components of the soil mix are not dry, the soil is dried at 100° C. to constant weight before determining w1. The soil in the pot is watered to full saturation and all the gravitational water is allowed to drain out. The weight of the soil (w2) after all gravitational water has seeped out (minus the pot weight) is determined. Field capacity is the weight of the water remaining in the soil obtained as w2-w1. It can be written as a percentage of the oven-dry soil weight.

Stress Treatment: Plants are allowed to grow for an initial period of 12 to 14 days under well-watered conditions, following which the soil moisture content is reduced to ~30% field capacity to administer a chronic drought stress. Measurements on chlorophyll fluorescence are recorded during this early growth period (well-watered observations) and during recovery from drought stress upon rewatering during the chronic drought stress period (drought-stressed observations). After the chronic drought-stress treatment, water is completely withheld to allow the plants to come very close to permanent wilting point (~8% field capacity), at which point they are watered to saturation. The recovery of plants from this severe drought is recorded as hours to 50% recovery or as the number of plants recovered after 48 hours of drought stress. At the end of the experiments, shoots are collected for fresh and dry weight measurements.

Observations Made: Observations are recorded on chlorophyll fluorescence as PhiPSII (which is indicative of the operating quantum efficiency of photosystem II photochemistry) and Fv'/Fm' (which is the maximum efficiency of photosystem II), during the well-watered growth, as well as during recovery from drought stress upon re-watering. These measurements are recorded using the Hansatech FMS2 instrument (Hansatech Instruments Ltd. Norfolk, England). Measurements are recorded for the youngest fully expanded leaf. Observations are also recorded on the recovery of plants after a severe drought stress, and also on the fresh and dry weights of the shoots at the end of the experimental period.

Six events of the rd29a:ZmNPK1b construct were tested for improved drought tolerance. Under well-watered conditions, Fv'/Fm' for two of the six events was significantly higher than that of the control. Notably, under drought conditions as described above, five of the six events showed significantly higher Fv'/Fm' than the control. Four of those five also scored significantly better than the control for PSII fluorescence under drought.

Recovery score indicates a plant's ability to recover after the drought stress is relieved as described above. Early recovery or reduced time required for recovery is sought in a plant that has improved drought tolerance. Two of the events with improved fluorescence scores also showed significantly reduced recovery time compared to the control.

To investigate whether these positive data reflected a bias toward smaller plants, wet and dry mass of the seedling shoots was measured. Only one event (Event 3.1) had an average wet shoot mass smaller than the control. All others were equivalent or larger (Event 3.39). Five of the six events were unchanged in dry shoot mass relative to the control; one event had a reduced mass.

TABLE 7

Seedling drought screen of PHP32984 transgenic maize

| Event | WW Fluorescence Fv'/Fm' | WW Fluorescence ?PSII | DRT Fluorescence Fv'/Fm' | DRT Fluorescence ?PSII | Recovery hour | Wet Shoot gram | Dry Shoot gram |
| --- | --- | --- | --- | --- | --- | --- | --- |
| 3.39 | 0.530a | 0.420a | 0.687a | 0.511a | 12.3b | 2.90a | 0.3999a |
| 3.32 | 0.488b | 0.380a | 0.668ab | 0.505a | 18.7a | 2.34b | 0.3683a |
| 3.19 | 0.464b | 0.366a | 0.640ab | 0.484a | 12.8b | 2.43b | 0.3441b |
| 2.9  | 0.489b | 0.392a | 0.603c  | 0.452b | 21.3a | 2.28b | 0.3657a |
| 1.3  | 0.476b | 0.415a | 0.615b  | 0.459b | 18.4a | 2.32b | 0.4004a |

TABLE 7-continued

Seedling drought screen of PHP32984 transgenic maize

| Event | WW Fluorescence Fv'/Fm' | WW Fluorescence ?PSII | DRT Fluorescence Fv'/Fm' | DRT Fluorescence ?PSII | Recovery hour | Wet Shoot gram | Dry Shoot gram |
|---|---|---|---|---|---|---|---|
| 3.1 | 0.497a | 0.420a | 0.661ab | 0.485a | 20.2a | 1.99c | 0.3946a |
| control | 0.475b | 0.400a | 0.605c | 0.460b | 19.9a | 2.09b | 0.3697a |

In summary, 83% of rd29a::ZmNPK1b events tested showed significantly improved Fv'/Fm' under drought conditions, relative to the control.

Oxidative stress is a major cause of damage in plants exposed to stressful environmental conditions. Oxidative stress results from the cellular damage caused by reactive oxygen species that are generated in cells. These reactive oxygen molecules can damage membranes, proteins, and nucleic acids. Transgenic plants that express a MAPKKK of the present invention may be analyzed for improved resistance to oxidative stress.

Transgenic plants expressing a MAPKKK of the present invention may be assayed in artificial environments or in the field to demonstrate that the transgene confers resistance or tolerance to chemicals (e.g., herbicides, ozone or pollutants) or metals (e.g., copper or zinc). Transgenic plants having an increased ability to grow in the presence of higher concentrations of the toxic compound, as compared to non-transgenic plants, are useful in the invention.

In another aspect, a MAPKKK of the present invention described herein may improve crop yield or productivity. Seeds of transgenic plants expressing a MAPKKK of the present invention may be planted in test plots and their agronomic performance compared to standard plants using techniques familiar to those of skill in the art. Optionally included in this comparison are plants of similar genetic background without the transgene. A yield benefit may be observed and plants exhibiting the increased yield are advanced for commercialization.

In addition, transgenic plants expressing a MAPKKK of the present invention may be field tested for agronomic performance under conditions, including, but not limited to, limited or inadequate water availability to simulate drought. When compared to nontransgenic plants, transgenic plants expressing a MAPKKK of the present invention may exhibit higher yield than their nontransgenic counterparts under non-optimal growing conditions.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated mitogen-activated protein kinase kinase kinase (MAPKKK) polynucleotide selected from the group consisting of:
   (a) a polynucleotide that encodes the polypeptide of SEQ ID NO: 2;
   (b) a polynucleotide comprising the sequence set forth in SEQ ID NO: 1;
   (c) a polynucleotide encoding a polypeptide having at least 95% sequence identity to the entire length of SEQ ID NO: 2, wherein the % sequence identity is determined by GAP Version 10 under default parameters; and
   (d) an isolated polynucleotide degenerate from any of (a) to (c) as a result of the genetic code.

2. A vector comprising at least one polynucleotide of claim 1.

3. An isolated polypeptide with MAPKKK activity, selected from the group consisting of:
   (a) an isolated polypeptide comprising SEQ ID NO: 2;
   (b) a polypeptide that is at least 95% identical to the amino acid sequence of SEQ ID NO: 2;

(c) a polypeptide that is encoded by a nucleic acid molecule comprising a nucleotide sequence that is at least 95% identical to the full length of SEQ ID NO: 1; and
(d) a fragment comprising at least 200 consecutive amino acids of SEQ ID NO: 2.

4. A recombinant expression cassette comprising a polynucleotide operably linked to a promoter, wherein the polynucleotide encodes the polypeptide of claim 3.

5. A transformed host cell comprising the isolated polypeptide of claim 3.

6. The host cell of claim 5, wherein the host cell is a transformed plant cell.

7. The plant cell of claim 6, wherein the plant cell is selected from the group consisting of sorghum, maize, rice, wheat, soybean, sunflower, canola, alfalfa, barley and millet.

8. A transformed plant regenerated from the plant cell of claim 6.

9. A transformed seed of the plant of claim 8.

* * * * *

SEQUENCE LISTING

```
<160> NUMBER OF SEQ ID NOS: 20

<210> SEQ ID NO 1
<211> LENGTH: 1396
<212> TYPE: DNA
<213> ORGANISM: Zea mays
<220> FEATURE:
<221> NAME/KEY: CDS
<222> LOCATION: (72)...(1395)

<400> SEQUENCE: 1
aaacaaacaa aaaaaagacc accaagaaca tcgcaaaaaa gacagaaagg aagaaacaga      60
ggcagaagcc c atg gcg gcg agc ggg cgc tgg agg agg ctg cgg acg ctg      110
            Met Ala Ala Ser Gly Arg Trp Arg Arg Leu Arg Thr Leu
              1               5                   10 ggc cgc ggc gcg tcg ggc gcc gtg gtg tcg ctg gcg tcg gac gcg gcg      158
Gly Arg Gly Ala Ser Gly Ala Val Val Ser Leu Ala Ser Asp Ala Ala
         15                  20                  25 tcg ggg gag ctg ttc gcg gtc aag tca gcc ggc gcg agc ggc gcg gcg      206
Ser Gly Glu Leu Phe Ala Val Lys Ser Ala Gly Ala Ser Gly Ala Ala
 30                  35                  40                  45 acg ctg cgg cgg gag cat gcg gtg ctg cgc ggc ctg cgg tcg ccg cac      254
Thr Leu Arg Arg Glu His Ala Val Leu Arg Gly Leu Arg Ser Pro His
                 50                  55                  60 gtg gtg cgc tgc gtg ggc ggc ggc gag ggc gcg gac ggg tcg tac cag      302
Val Val Arg Cys Val Gly Gly Gly Glu Gly Ala Asp Gly Ser Tyr Gln
```

-continued

```
                65                  70                  75
gtg ttc ctc gag tac gcc ccc ggc ggg tcg gtc gcc gac gcg gtg gcc     350
Val Phe Leu Glu Tyr Ala Pro Gly Gly Ser Val Ala Asp Ala Val Ala
            80                  85                  90 agg ggc ggg ggc gcg ctg gag gag cgc gcc atc cgc gcg ctc gcc gcg     398
Arg Gly Gly Gly Ala Leu Glu Glu Arg Ala Ile Arg Ala Leu Ala Ala
        95                 100                 105 gac gtg ctg cgc ggg ctg gcc tac ctc cac ggc cgc tcc gtg gtg cac     446
Asp Val Leu Arg Gly Leu Ala Tyr Leu His Gly Arg Ser Val Val His
110                 115                 120                 125 ggc gac gtg aag gcg cgc aac gtg ctg ctg ggc gcc gac ggg cgc gcc     494
Gly Asp Val Lys Ala Arg Asn Val Leu Leu Gly Ala Asp Gly Arg Ala
            130                 135                 140 agg ctg gcg gac ttc ggg tgc gcg cgg acg ccc ggc ttc tcc gcg cgg     542
Arg Leu Ala Asp Phe Gly Cys Ala Arg Thr Pro Gly Phe Ser Ala Arg
        145                 150                 155 cgc ccg ctc ggc ggc acg ccg gcg ttc atg gcg ccc gag gtt gcc cgc     590
Arg Pro Leu Gly Gly Thr Pro Ala Phe Met Ala Pro Glu Val Ala Arg
    160                 165                 170 ggg gag gcc cag ggc ccc gcc gcc gac gtg tgg gcg ctc ggc tgc acg     638
Gly Glu Ala Gln Gly Pro Ala Ala Asp Val Trp Ala Leu Gly Cys Thr
175                 180                 185 gtc gtc gag atg gcc acc ggc cgc gcc ccg tgg ggc ggc gcc gac gcc     686
Val Val Glu Met Ala Thr Gly Arg Ala Pro Trp Gly Gly Ala Asp Ala
190                 195                 200                 205 gac gtc ctc gcc gcc gtg cac cgg atc ggg tac acg gac gcc gtg ccc     734
Asp Val Leu Ala Ala Val His Arg Ile Gly Tyr Thr Asp Ala Val Pro
            210                 215                 220 gac gcg ccg tcc tgg atg tcg gcc gag gcc cgg gac ttc ctg gcc cgc     782
Asp Ala Pro Ser Trp Met Ser Ala Glu Ala Arg Asp Phe Leu Ala Arg
        225                 230                 235 tgc ttc gcc agg gac gcc gcc gag cgg tgg acc gcc gcg cag ctc ctt     830
Cys Phe Ala Arg Asp Ala Ala Glu Arg Trp Thr Ala Ala Gln Leu Leu
    240                 245                 250 gag cac ccg ttc gtg gcg gct ccc tgc cac ggc cac ggc gac cac gag     878
Glu His Pro Phe Val Ala Ala Pro Cys His Gly His Gly Asp His Glu
255                 260                 265 gcc ccg cgg gtg tcg ccc aag agc acg ctg gac gcc gca ttc tgg gag     926
Ala Pro Arg Val Ser Pro Lys Ser Thr Leu Asp Ala Ala Phe Trp Glu
270                 275                 280                 285 gcc gaa gac gac gac gac gac gcg gac gag gca gtg tcg gcg agt gcg     974
Ala Glu Asp Asp Asp Asp Asp Ala Asp Glu Ala Val Ser Ala Ser Ala
            290                 295                 300 tcg gag agg atc aag tcg ctg gcg tgc tcc gcc tgc gcc ttg ccc gac    1022
Ser Glu Arg Ile Lys Ser Leu Ala Cys Ser Ala Cys Ala Leu Pro Asp
        305                 310                 315 tgg gac ggg gag gac ggg tgg atc gaa gtg ctg ggt gat cag cag cgg    1070
Trp Asp Gly Glu Asp Gly Trp Ile Glu Val Leu Gly Asp Gln Gln Arg
    320                 325                 330 gtc gag gtc tgc ggc gcg gtg cag gtg gcg cgc agc gcg cca ggc aaa    1118
Val Glu Val Cys Gly Ala Val Gln Val Ala Arg Ser Ala Pro Gly Lys
335                 340                 345 gtg tcc agc gtc ctg gcg gtg cca gct ggg gag atg gat gtc ggc ggc    1166
Val Ser Ser Val Leu Ala Val Pro Ala Gly Glu Met Asp Val Gly Gly
350                 355                 360                 365 ggc ggc ggc ggc ggt gat gaa ctg gaa gca gag gac gtg tcg ttc        1214
Gly Gly Gly Gly Gly Asp Glu Leu Glu Ala Glu Asp Val Ser Phe
            370                 375                 380 ggt ggc gag gtt cca gga tca gcg gat gct tcg gct gag cgt cag aag    1262
Gly Gly Glu Val Pro Gly Ser Ala Asp Ala Ser Ala Glu Arg Gln Lys
```

```
                        385                 390                 395
aaa cgc tat ttg att ttg cgt tcg cac tac tgt cat gta ctc tcg tgt      1310
Lys Arg Tyr Leu Ile Leu Arg Ser His Tyr Cys His Val Leu Ser Cys
            400                 405                 410 cag tta gtg ccc tgt aat cta cca cta gta gtt gtt aat aat gca ata      1358
Gln Leu Val Pro Cys Asn Leu Pro Leu Val Val Val Asn Asn Ala Ile
415                 420                 425 aag tta tgg gtt ccc aca aaa aaa aaa aaa aaa aaa a a                  1396
Lys Leu Trp Val Pro Thr Lys Lys Lys Lys Lys Lys
430                 435                 440

<210> SEQ ID NO 2
<211> LENGTH: 441
<212> TYPE: PRT
<213> ORGANISM: Zea mays

<400> SEQUENCE: 2

Met Ala Ala Ser Gly Arg Trp Arg Arg Leu Arg Thr Leu Gly Arg Gly
1               5                   10                  15

Ala Ser Gly Ala Val Val Ser Leu Ala Ser Asp Ala Ala Ser Gly Glu
            20                  25                  30

Leu Phe Ala Val Lys Ser Ala Gly Ala Ser Gly Ala Ala Thr Leu Arg
        35                  40                  45

Arg Glu His Ala Val Leu Arg Gly Leu Arg Ser Pro His Val Val Arg
    50                  55                  60

Cys Val Gly Gly Gly Glu Gly Ala Asp Gly Ser Tyr Gln Val Phe Leu
65                  70                  75                  80

Glu Tyr Ala Pro Gly Gly Ser Val Ala Asp Val Ala Arg Gly Gly
                85                  90                  95

Gly Ala Leu Glu Glu Arg Ala Ile Arg Ala Leu Ala Ala Asp Val Leu
            100                 105                 110

Arg Gly Leu Ala Tyr Leu His Gly Arg Ser Val Val His Gly Asp Val
        115                 120                 125

Lys Ala Arg Asn Val Leu Leu Gly Ala Asp Gly Arg Ala Arg Leu Ala
    130                 135                 140

Asp Phe Gly Cys Ala Arg Thr Pro Gly Phe Ser Ala Arg Arg Pro Leu
145                 150                 155                 160

Gly Gly Thr Pro Ala Phe Met Ala Pro Glu Val Ala Arg Gly Glu Ala
                165                 170                 175

Gln Gly Pro Ala Ala Asp Val Trp Ala Leu Gly Cys Thr Val Val Glu
            180                 185                 190

Met Ala Thr Gly Arg Ala Pro Trp Gly Gly Ala Asp Ala Asp Val Leu
        195                 200                 205

Ala Ala Val His Arg Ile Gly Tyr Thr Asp Ala Val Pro Asp Ala Pro
    210                 215                 220

Ser Trp Met Ser Ala Glu Ala Arg Asp Phe Leu Ala Arg Cys Phe Ala
225                 230                 235                 240

Arg Asp Ala Ala Glu Arg Trp Thr Ala Ala Gln Leu Leu Glu His Pro
                245                 250                 255

Phe Val Ala Ala Pro Cys His Gly His Gly Asp His Glu Ala Pro Arg
            260                 265                 270

Val Ser Pro Lys Ser Thr Leu Asp Ala Ala Phe Trp Glu Ala Glu Asp
        275                 280                 285

Asp Asp Asp Asp Ala Asp Glu Ala Val Ser Ala Ser Ala Ser Glu Arg
    290                 295                 300

Ile Lys Ser Leu Ala Cys Ser Ala Cys Ala Leu Pro Asp Trp Asp Gly
```

```
                    305                 310                 315                 320
Glu Asp Gly Trp Ile Glu Val Leu Gly Asp Gln Gln Arg Val Glu Val
                325                 330                 335

Cys Gly Ala Val Gln Val Ala Arg Ser Ala Pro Gly Lys Val Ser Ser
            340                 345                 350

Val Leu Ala Val Pro Ala Gly Glu Met Asp Val Gly Gly Gly Gly Gly
        355                 360                 365

Gly Gly Gly Asp Glu Leu Glu Ala Glu Asp Val Ser Phe Gly Gly Glu
    370                 375                 380

Val Pro Gly Ser Ala Asp Ala Ser Ala Glu Arg Gln Lys Lys Arg Tyr
385                 390                 395                 400

Leu Ile Leu Arg Ser His Tyr Cys His Val Leu Ser Cys Gln Leu Val
                405                 410                 415

Pro Cys Asn Leu Pro Leu Val Val Asn Asn Ala Ile Lys Leu Trp
            420                 425                 430

Val Pro Thr Lys Lys Lys Lys Lys
        435                 440

<210> SEQ ID NO 3
<211> LENGTH: 6053
<212> TYPE: DNA
<213> ORGANISM: Zea mays

<400> SEQUENCE: 3
ggcatgcctt tagcctgatc tacagcgaga cattcagaca tatatactga ttttttttc       60
ccgtggccga ggataaggtg gaaaaccggc tggtaatttg tagctgaacc tacatgtgga      120
aagctcagaa agaaggcaaa gctccgttgg ttgaactgaa aagagcccca aaccgaactg      180
aaacatacgt atattttgca gctgcagcga gccatggtga gtgagttgat agatggtggg      240
cgcgacgtca ttccacacaa acatgcacgc tactttgttt gtcgagatta gactgacctg      300
gagccagcca cctgcccgct tccatgcttg ttcctcagcg cggttcagag catctctggc      360
gcggccatca ctataggtac gttttctgct tgaactcgaa tcaaaaacca cgccgacctg      420
attgatcgat gcctaggcaa gttcggcgtg aactgttcgt gaaccacctc ttgtccattt      480
ttttttttgtt attggggttg tccgttgaca atgttcaata gtcaacaagc ctaaaccagc      540
ggcagaaaca cacaaagttg acctgctgca tgaccagcct gaagccctga accttgtagg      600
accagaaacg aaacagcaca gggagggacg ggacgagacg agacagaggc ctaacgctac      660
acggcctata aaagccgaag gcaacagagc aagcgagagc ggtgagcggc actgtgtgaa      720
taatggcctc gggtcgggcg ggagtgagtg gaacttgcat tttagcacga gcaggcggag      780
ttcgttaccc aatcggatct acgcgcacct actgccgatc gcttccgaat cgacgacggg      840
cctgctgaag ctgatcgccc ccgcctttcg tctcgacccc cgatttgatc tcgtcaccgt      900
gttgttggga tagggtgggt gggtgggtgg gtgtgccatc tctggtgcaa ccgacgatcg      960
agcgggcagt acaggtcaag cgcctaccta ccgacgatcg ccgggggtgt gggtttggtg     1020
gagcaaacgc tgctgctgct gacccctccc tacgctagcg catggtagca gtaaattctg     1080
ttctacgcgg gtcgcagcga gcgccctttt ttaggcgcac gcgttgacct cccgccggcc     1140
cgagcatgtc ccgatcgccg gccgtgcccg tgctacggcc gctggacctc gctttctcgg     1200
ggcgccacga tccgtatcct tgtgagatg gagaagcggc cacgacgcga ggagggtcgt      1260
cgcgtcgcaa cttggccttg ttcggtcggc gctgcacgt ccactcctgg ccggtcctgc      1320
tgcaccctgg acccggttca aacggtcctg gaccggtgca tccgctgatt aattagcgcg     1380
```

-continued

```
accgaccgga gaacgtagca gcaggcatca acagcacgct cgtgtttcat acctgttttt   1440
tttatttatt tctgtcccag gagaagtgcc gcctctcgct ccacccatct gatcacacga   1500
ggaacacgag ccgatggctg ctgccgatgc tgttacgggt ttagacttgc taatactgcg   1560
ggagtagttt ttttttttcac tttctttcat ggacataaat aggctttcta ataccgat    1620
cattggcaat ttggcatgtg gtagccatct cgggatcccc tccaaatcag gcatctcgtt   1680
ttttcgggat cgcagatcag gtgcctttaa cacgagacaa ttggaaagcg gcatgtttt    1740
atatggcatc aaaaaagaaa agaaaaaaaa tcagaaaacg gggtgacgct gacgccgctg   1800
gcggaacgga aagggtttca cgccgcgccg gtcaggaggg gtcaggcggc ccgcaggccc   1860
tcgttaatta gccgcacgag tcgcgcccgc ccacacgccg tccaattgcc gcgcgtggga   1920
gggagcgacg gctacgcgag gcgcgaccca cgccttcccc cccgtgccga tttcctaatc   1980
ccgcccccac ccaacttgag cctttgacgc acaccaaaca gcctcttata actaaactaa   2040
tccacccacc cacccaaatt aacttcccct cctcctcctc ctcctccaca ccttgccgag   2100
ctttgtatat aaacgctcgc aactcaccca catcaagggc aggctcacga ttccagctca   2160
ggcggccaaa caaacaaaaa aaagaccacc aagaacatcg caaaaaagac agaaaggaag   2220
aaacagaggc agaagcccat ggcggcgagc gggcgctgga ggaggctgcg gacgctgggc   2280
cgcggcgcgt cgggcgccgt ggtgtcgctg gcgtcggacg cggcgtcggg ggagctgttc   2340
gcggtcaagt cagccggcgc gagcggcgcg gcgacgctgc ggcgggagca tgcggtgctg   2400
cgcggcctgc ggtcgccgca cgtggtgcgc tgcgtgggcg gcggcgaggg cgcggacggg   2460
tcgtaccagg tgttcctcga gtacgccccc ggcgggtcgg tcgccgacgc ggtggccagg   2520
ggcggggggcg cgctggagga gcgcgccatc cgcgcgctcg ccgcggacgt gctgcgcggg   2580
ctggcctacc tccacggccg ctccgtggtg cacggcgacg tgaaggcgcg caacgtgctg   2640
ctgggcgccg acgggcgcgc caggctggcg gacttcgggt gcgcgcggac gcccggcttc   2700
tccgcgcggc gcccgctcgg cggcacgccg gcgttcatgg cgcccgaggt tgcccgcggg   2760
gaggcccagg gccccgccgc cgacgtgtgg gcgctcggct gcacggtcgt cgagatggcc   2820
accggccgcg ccccgtgggg cggcgccgac gccgacgtcc tcgccgccgt gcaccggatc   2880
gggtacacgg acgccgtgcc cgacgcgccg tcctggatgt cggccgaggc ccgggacttc   2940
ctggcccgct gcttcgccag ggacgccgcc gagcggtgga ccgccgcgca gctccttgag   3000
cacccgttcg tggcggctcc ctgccacggc cacggcgacc acgaggcccc gcgggtgtcg   3060
cccaagagca cgctggacgc cgcattctgg gaggccgaag acgacgacga cgacgcggac   3120
gaggcagtgt cggcgagtgc gtcggagagg atcaagtcgc tggcgtgctc cgcctgcgcc   3180
ttgcccgact gggacgggga ggacgggtgg atcgaagtgc tgggtgatca gcagcgggtc   3240
gaggtctgcg gcgcggtgca ggtggcgcgc agcgcgccag gcaaagtgtc cagcgtcctg   3300
gcggtgccag ctggggagat ggatgtcggc ggcggcggcg gcggcggcgg tgatgaactg   3360
gaagcagagg acgtgtcgtt cggtggcgag gttccaggat cagcggatgc ttcggctgag   3420
cgtcagaaga aacgctattt gattttgcgt tcgcactact gtcatgtact ctcgtgtcag   3480
ttagtgccct gtaatctacc actagtagtt gttaataatg caataaagtt atgggttccc   3540
acaaatgtct tgttgtgccg ctctgttcga ttccccttgt catgatactc ctctctgctc   3600
atgtacgcga tacatggcca cgacttgctg tccgcacgtg catggctggc tggaatatac   3660
tccgtagtcg acttgctgtg gagtacctcc ctccatacccc tgctttgctt tctcttaggg   3720
tgcgttcggt tattcaggat tctgcttcag taaagaatcc agctagaata attgtataat   3780
```

```
ttatagaaca attggtaacc tggaatagtt cttactcttg ttccaggcct tagtctttac    3840
agtaggccac actcgcgcca cgccacgcca aggcaaaaaa aagaagaaga agaagaagaa    3900
gaagcaggga cgtgacgaca tagcatgacc tggttcgttc gactcgggaa cgctatttgt    3960
tcgataacac ctgggtttgt ttatctcata ttggaacttc caatccacgg ctaggtctgg    4020
accgggaaac cggcggtgga ttctcttctc tccggggcac ggccggcggg caggcatcgg    4080
ctgacgcgaa gaacgaaaag aagcaggcac tccgatcgcg caaaggcagg caggcagcag    4140
catctgcccc tttcgacggg gaacgggcaa aacgggatta tccacagccg acaccacagc    4200
gtcatgcggc cgggctggtg ggtggcggcc gagtcggtgc gcgcttgatg gggggccggc    4260
gaggcggcac gccggctgac gcgaccccg catcatgggt tccgtcacgg cgcaatatgc     4320
ctatgctatg cgggtgtctc accgtaccgt acgcggtcaa agcacaagcc ggcaccatga    4380
tttactcgct cctccgtggc ggtcagcgta ggcgtagcta cagctgccat gccatgtcat    4440
gccaccaccc cggcgccga ttgtccgccc gtcacgtacc ggtcgcccgc gacgcaccag     4500
caggttggca acacaggtgt tgctgctctc tcgagtctcg actccgaagg cgtgcgtggc    4560
tggtgcggtg gttacccgta gtcgcgtcat cgccgccgcg ctggtcagcc ggtcagggac    4620
gcatcgtgct atgtgactgg gccacggggt aatgaaggta ccggagagcg cagagataga    4680
tggagtccac gggggagtga gtgcatttgg aggccagctc ctgctgccac ggtagagtcc    4740
agagctttcg gccgcctctg tctcaggtct ctcctccgcc tgtgtaagtg tgtagcgtag    4800
cttatgcccc gggcggcacc tactttgtgc acagtgcact gcccgtggat caaaattcta    4860
gaacgtgttg ttctagtgac tcctggtcgg cacgcccagg gttctagaga ggtacagaac    4920
atctgttctc cctctgtctg gatatggctt cttcagttct tcggaaggct tgggttcggt    4980
tcggtgaagt caacggcttt ggaatgttcg aggggcgcg cagaagggtg tgaacatata     5040
tgtacatgtc cgtgatggcg accgtgttct gtctagaagc agcactagcg gggcttggct    5100
tgctgcctgc ctgacgaggt gctgatgtaa taataaagta aagctccgat ggataaacga    5160
ggaaaagaac tccaggcgct gatctcctag actcacatgc aggcctgcta atggcaaaaa    5220
atccaatcca ctcccaccca tacccaaatc taattacttt gatattcatc ccacacccaa    5280
ccaaaaatac tagagggaag ttaaacccaa cccatccaat aacattattg attccaaacc    5340
aacccgtaat tgggtggaaa cccgtggaaa acccgtgggt ttagcttatt gtctcacatc    5400
aagccaactg catacacatt ttaaaaatca cattttaaag cagtaaattc atttaaatga    5460
aaaagttttc aactacaaat ttgtataact catcatgatg tacattttat attttgaaca    5520
tttcttcata tgataaacta aaaataaatt tgttaataaa acctatatct ctctcatagt    5580
ttatggaact acgagagata tgtatagaat ttgtgcatat tgttagaact atcatgtgag    5640
atgaacaaat gatcaaacaa ccaaaataaa ctttgtagat cttgaaaagt tatagaagtt    5700
agaagttgac aacttttttca tttgaagtca tattgtcaac gaaaactatg cctgaattta    5760
aaaaatttaa aatttgaatt tgaaaacaa cctcgaagaa aaaaccacc aacatgaaag      5820
ttgtaggtat tgaagagtta tgaaactttg tagttgacaa tgttttgatt tgaaatcatc    5880
ttgccatgca aaactatgtt tgaattttga attttaaatt tttcaaccta catcggatgg    5940
aaaaaccacc aaaataaatg ttgtaggtct tgaaatgtta tgaaactttg taattgtcaa    6000
cttttttgtt tgaaatcatc ttatcattga aaaattcatg tgaagtttca aat           6053
```

```
<210> SEQ ID NO 4
<211> LENGTH: 1542
<212> TYPE: DNA
```

<213> ORGANISM: Zea mays
<220> FEATURE:
<221> NAME/KEY: CDS
<222> LOCATION: (1)...(1542)

<400> SEQUENCE: 4

```
atg acg acg acg acc acg gcg aag cag ctc cgg cgc gtg cgc acg ctc      48
Met Thr Thr Thr Thr Thr Ala Lys Gln Leu Arg Arg Val Arg Thr Leu
 1               5                  10                  15 ggc cgc ggc gcg tcg ggc gcc gtg gtg tgg ctg gcc tcc gac gag gcc      96
Gly Arg Gly Ala Ser Gly Ala Val Val Trp Leu Ala Ser Asp Glu Ala
             20                  25                  30 tcg ggc gag ctg gtg gcg gtc aag tcg gcg cgc gcc gcc ggg gcc gcg     144
Ser Gly Glu Leu Val Ala Val Lys Ser Ala Arg Ala Ala Gly Ala Ala
         35                  40                  45 gcg cag ctg cag cgc gag ggc cgc gtc ctc cgg ggc ctc tcg tcg ccg     192
Ala Gln Leu Gln Arg Glu Gly Arg Val Leu Arg Gly Leu Ser Ser Pro
     50                  55                  60 cac atc gtg ccc tgc ctc ggc tcc cgc gcc gcg gcg ggc ggc gag tac     240
His Ile Val Pro Cys Leu Gly Ser Arg Ala Ala Ala Gly Gly Glu Tyr
 65                  70                  75                  80 cag ctc ctg ctg gag ttc gcg ccg ggc ggg tcg ctg gcc gac gag gcc     288
Gln Leu Leu Leu Glu Phe Ala Pro Gly Gly Ser Leu Ala Asp Glu Ala
                 85                  90                  95 gcc agg agc ggc ggg ggc cgc ctc gcg gag cgc gcc atc ggc gcc tac     336
Ala Arg Ser Gly Gly Gly Arg Leu Ala Glu Arg Ala Ile Gly Ala Tyr
            100                 105                 110 gcc ggg gac gtg gcg cgc ggg ctg gcg tac ctc cac ggc cgg tcg ctc     384
Ala Gly Asp Val Ala Arg Gly Leu Ala Tyr Leu His Gly Arg Ser Leu
        115                 120                 125 gtg cac ggg gac gtc aag gcc cgg aac gtg gtc atc ggc ggc gac ggg     432
Val His Gly Asp Val Lys Ala Arg Asn Val Val Ile Gly Gly Asp Gly
    130                 135                 140 cgc gcc agg ctg acc gac ttc ggg tgc gcg agg ccg gcc ggg ggg tcg     480
Arg Ala Arg Leu Thr Asp Phe Gly Cys Ala Arg Pro Ala Gly Gly Ser
145                 150                 155                 160 acg cgc ccc gtc ggg ggc acc ccg gcc ttc atg gcg ccc gag gtg gcg     528
Thr Arg Pro Val Gly Gly Thr Pro Ala Phe Met Ala Pro Glu Val Ala
                165                 170                 175 cgc ggc cag gag cag ggc ccc gcc gcc gac gtc tgg gcg ctc ggg tgc     576
Arg Gly Gln Glu Gln Gly Pro Ala Ala Asp Val Trp Ala Leu Gly Cys
            180                 185                 190 atg gtc gtc gag ctg gcc acg ggc cgc gcg ccc tgg agc gac gtg gag     624
Met Val Val Glu Leu Ala Thr Gly Arg Ala Pro Trp Ser Asp Val Glu
        195                 200                 205 ggc gac gac ctc ctc gcc gcg ctc cac cgg atc ggg tac acg gac gac     672
Gly Asp Asp Leu Leu Ala Ala Leu His Arg Ile Gly Tyr Thr Asp Asp
    210                 215                 220 gtg ccg gag gtg ccc gcg tgg ctg tcg ccc gag gcc aag gac ttc ctg     720
Val Pro Glu Val Pro Ala Trp Leu Ser Pro Glu Ala Lys Asp Phe Leu
225                 230                 235                 240 gcc ggc tgc ttc gag cgc cgc gcc gcc gcg cgg ccc acg gcc gcg cag     768
Ala Gly Cys Phe Glu Arg Arg Ala Ala Ala Arg Pro Thr Ala Ala Gln
                245                 250                 255 ctc gcg gcg cac ccg ttc gtc gtc gcc tcc gcc tcc gcc gcc gcc gcc     816
Leu Ala Ala His Pro Phe Val Val Ala Ser Ala Ser Ala Ala Ala Ala
            260                 265                 270 atc cgc ggc ccg gcg aag cag gag gtg gtc ccg tca ccc aag agc acg     864
Ile Arg Gly Pro Ala Lys Gln Glu Val Val Pro Ser Pro Lys Ser Thr
        275                 280                 285 ctg cac gac gcg ttc tgg gac tcg gac gcc gag gac gaa gcg gac gag     912
Leu His Asp Ala Phe Trp Asp Ser Asp Ala Glu Asp Glu Ala Asp Glu
```

```
Leu His Asp Ala Phe Trp Asp Ser Asp Ala Glu Asp Glu Ala Asp Glu
        290                 295                 300 atg tcg acg ggc gcg gcg gcc gag agg atc ggg gca ttg gcg tgc gcc      960
Met Ser Thr Gly Ala Ala Ala Glu Arg Ile Gly Ala Leu Ala Cys Ala
305                 310                 315                 320 gcc tcc gcg ctg cct gac tgg gac acc gag gaa ggc tgg atc gac ctc     1008
Ala Ser Ala Leu Pro Asp Trp Asp Thr Glu Glu Gly Trp Ile Asp Leu
                325                 330                 335 cag gac gac cac tcg gcc gga act gcc gac gca ccg ccg gcg ccc gtc     1056
Gln Asp Asp His Ser Ala Gly Thr Ala Asp Ala Pro Pro Ala Pro Val
            340                 345                 350 gcg gac tac ttc atc agc tgg gcg gag ccg tca gac gca gag ctg gaa     1104
Ala Asp Tyr Phe Ile Ser Trp Ala Glu Pro Ser Asp Ala Glu Leu Glu
        355                 360                 365 cca ttc gtc gcc gtc gcc gcc gcc gca ggt ctc ccg cac gtt gca gga     1152
Pro Phe Val Ala Val Ala Ala Ala Ala Gly Leu Pro His Val Ala Gly
    370                 375                 380 gtg gca tta gca ggc gcc acc gcc gtt aac ctg cag ggc agt tat tat     1200
Val Ala Leu Ala Gly Ala Thr Ala Val Asn Leu Gln Gly Ser Tyr Tyr
385                 390                 395                 400 tat tac ccg cct atg cat cta ggc gtc cgc gga aac gag att cca cgc     1248
Tyr Tyr Pro Pro Met His Leu Gly Val Arg Gly Asn Glu Ile Pro Arg
                405                 410                 415 ccg ttg ttg gat cat cat ggc gac ggg tta gaa aag ggg cag gga tcc     1296
Pro Leu Leu Asp His His Gly Asp Gly Leu Glu Lys Gly Gln Gly Ser
            420                 425                 430 cac cgc gtt tgt aac aga gaa aca gaa aag gta aca atg aaa cga att     1344
His Arg Val Cys Asn Arg Glu Thr Glu Lys Val Thr Met Lys Arg Ile
        435                 440                 445 tcg tta aaa aga aga gct gct ttc ctt ctc gac cag cat cac gtg cga     1392
Ser Leu Lys Arg Arg Ala Ala Phe Leu Leu Asp Gln His His Val Arg
    450                 455                 460 tcg ctg gac aaa ctg gaa tat cgt cca cgt cac gac cga atg ctg cgt     1440
Ser Leu Asp Lys Leu Glu Tyr Arg Pro Arg His Asp Arg Met Leu Arg
465                 470                 475                 480 cga cgg caa tct ata tat cgg agc aat agc gtc ctt ggt tac gac gtt     1488
Arg Arg Gln Ser Ile Tyr Arg Ser Asn Ser Val Leu Gly Tyr Asp Val
                485                 490                 495 agc aaa ggt agg cag gtc cgt tgg cgc cgt gcg gtt tgc att gcc gtt     1536
Ser Lys Gly Arg Gln Val Arg Trp Arg Arg Ala Val Cys Ile Ala Val
            500                 505                 510 gct gcc                                                              1542
Ala Ala <210> SEQ ID NO 5
<211> LENGTH: 514
<212> TYPE: PRT
<213> ORGANISM: Zea mays

<400> SEQUENCE: 5

Met Thr Thr Thr Thr Thr Ala Lys Gln Leu Arg Arg Val Arg Thr Leu
1               5                   10                  15

Gly Arg Gly Ala Ser Gly Ala Val Val Trp Leu Ala Ser Asp Glu Ala
            20                  25                  30

Ser Gly Glu Leu Val Ala Val Lys Ser Ala Arg Ala Ala Gly Ala Ala
        35                  40                  45

Ala Gln Leu Gln Arg Glu Gly Arg Val Leu Arg Gly Leu Ser Ser Pro
    50                  55                  60

His Ile Val Pro Cys Leu Gly Ser Arg Ala Ala Ala Gly Gly Glu Tyr
65                  70                  75                  80
```

```
Gln Leu Leu Leu Glu Phe Ala Pro Gly Gly Ser Leu Ala Asp Glu Ala
                 85                  90                  95

Ala Arg Ser Gly Gly Gly Arg Leu Ala Glu Arg Ala Ile Gly Ala Tyr
            100                 105                 110

Ala Gly Asp Val Ala Arg Gly Leu Ala Tyr Leu His Gly Arg Ser Leu
            115                 120                 125

Val His Gly Asp Val Lys Ala Arg Asn Val Val Ile Gly Gly Asp Gly
    130                 135                 140

Arg Ala Arg Leu Thr Asp Phe Gly Cys Ala Arg Pro Ala Gly Gly Ser
145                 150                 155                 160

Thr Arg Pro Val Gly Gly Thr Pro Ala Phe Met Ala Pro Glu Val Ala
                165                 170                 175

Arg Gly Gln Glu Gln Gly Pro Ala Ala Asp Val Trp Ala Leu Gly Cys
            180                 185                 190

Met Val Val Glu Leu Ala Thr Gly Arg Ala Pro Trp Ser Asp Val Glu
        195                 200                 205

Gly Asp Asp Leu Leu Ala Ala Leu His Arg Ile Gly Tyr Thr Asp Asp
210                 215                 220

Val Pro Glu Val Pro Ala Trp Leu Ser Pro Glu Ala Lys Asp Phe Leu
225                 230                 235                 240

Ala Gly Cys Phe Glu Arg Arg Ala Ala Ala Arg Pro Thr Ala Ala Gln
                245                 250                 255

Leu Ala Ala His Pro Phe Val Val Ala Ser Ser Ala Ala Ala Ala Ala
                260                 265                 270

Ile Arg Gly Pro Ala Lys Gln Glu Val Val Pro Ser Pro Lys Ser Thr
            275                 280                 285

Leu His Asp Ala Phe Trp Asp Ser Asp Ala Glu Asp Glu Ala Asp Glu
    290                 295                 300

Met Ser Thr Gly Ala Ala Ala Glu Arg Ile Gly Ala Leu Ala Cys Ala
305                 310                 315                 320

Ala Ser Ala Leu Pro Asp Trp Asp Thr Glu Glu Gly Trp Ile Asp Leu
                325                 330                 335

Gln Asp Asp His Ser Ala Gly Thr Ala Asp Ala Pro Pro Ala Pro Val
            340                 345                 350

Ala Asp Tyr Phe Ile Ser Trp Ala Glu Pro Ser Asp Ala Glu Leu Glu
        355                 360                 365

Pro Phe Val Ala Val Ala Ala Ala Gly Leu Pro His Val Ala Gly
370                 375                 380

Val Ala Leu Ala Gly Ala Thr Ala Val Asn Leu Gln Gly Ser Tyr Tyr
385                 390                 395                 400

Tyr Tyr Pro Pro Met His Leu Gly Val Arg Gly Asn Glu Ile Pro Arg
                405                 410                 415

Pro Leu Leu Asp His His Gly Asp Gly Leu Glu Lys Gly Gln Gly Ser
            420                 425                 430

His Arg Val Cys Asn Arg Glu Thr Glu Lys Val Thr Met Lys Arg Ile
        435                 440                 445

Ser Leu Lys Arg Arg Ala Ala Phe Leu Leu Asp Gln His His Val Arg
    450                 455                 460

Ser Leu Asp Lys Leu Glu Tyr Arg Pro Arg His Asp Arg Met Leu Arg
465                 470                 475                 480

Arg Arg Gln Ser Ile Tyr Arg Ser Asn Ser Val Leu Gly Tyr Asp Val
                485                 490                 495

Ser Lys Gly Arg Gln Val Arg Trp Arg Arg Ala Val Cys Ile Ala Val
```

```
                500            505             510
Ala Ala

<210> SEQ ID NO 6
<211> LENGTH: 4019
<212> TYPE: DNA
<213> ORGANISM: Zea mays

<400> SEQUENCE: 6
gggagacaaa caagggaaaa aaaaacacct cagatcgggg agagatgtag acattagaat     60
aaacccaacc ccggttcaag ttaatagagt tggtgatgag aacactactt acggggttca    120
ggcatgggcc aagtcagcat gtgagtccag ggggaggata aactacttta caaatggcca    180
tgagagcgtg ggttgagtga gttaaaggaa gaagaaaaaa aatctcagct gcgctcagac    240
gccgccgagt aagagacact gactgtcaga ggtcgccttg gcgtgccaaa actgtagcct    300
cgtcgttcgt ccacccgcgc gcaccggcgc tggcgttagt gcttaacgcc gccccggccc    360
cggctacctc tctgaaaaag tcgccagata ccaagaatgg ggagaacaaa cccgtgctgt    420
ttttacaaga gtaaaatata cgcagaagaa gaaaaggtcc tgacagggac gacaacatcc    480
agcctcagca accagtattc agccacgagc gaaagcgtcg gccgtcgccg gggagcgagc    540
aaaatcgcag acccggactc ggttaataat aattcagcca cgagcgagct cgcgcgcgct    600
tggatctttt ttgagtcggt agcgcttttg gacctgtttt tatttaggc aacgaaatgt     660
gcgcacatgc ccaatttgcg taaccgaacg catgtgccag atccgtcacg ccgaacgtac    720
gtacgtacgt tccccggacg gctcagttca gcctgcctaa cgggccataa attagggaaa    780
cggggactac ggaatagata ttaatcgaac tgagccggac agaacgtgcc agtgatttaa    840
agcagaggag atccagctat ccaagcgaag gaaaaccacg ctcgtctcga cgtggcagcc    900
taacaaacca ctccgtatat atatcaaagg aggcgctgat atcatgtgtg ctgtgtctct    960
cgtctcagcg tcacatcaca tcgcgcgtga ggcatcaggg gccggcgacg gcgaggtggc   1020
catccgtccg tcacgaaaaa ggggaaggct gctgcaacgc atcggatctc cccaccgaag   1080
atcgaggatc tcggcgttga catcctagtc gatccagtga tgtccactcc agacatgcaa   1140
tgcaatgcag cctggagcga gcagcggagc acgagcatgt cgcgatagca tagcattcga   1200
tcaggcagca acggcaatgc aaaccgcacg gcgccaacgg acctgcctac ctttgctaac   1260
gtcgtaacca aggacgctat tgctccgata tatagattgc cgtcgacgca gcattcggtc   1320
gtgacgtgga cgatattcca gtttgtccag cgatcgcacg tgatgctggt cgagaaggaa   1380
agcagctctt cttttttaacg aaattcgttt cattgttacc ttttctgttt ctctgttaca   1440
aacgcggtgg gatccctgcc ccttttctaa cccgtcgcca tgatgatcca acaacgggcg   1500
tggaatctcg tttccgcgga cgcctagatg cataggcggg taataataat aactgccctg   1560
caggttaacg gcggtggcgc ctgctaatgc cactcctgca acgtgcggga gacctgcggc   1620
ggcggcgacg gcgacgaatg gttccagctc tgcgtctgac ggctccgccc agctgatgaa   1680
gtagtccgcg acgggcgccg gcggtgcgtc ggcagttccg gccgagtggt cgtcctggag   1740
gtcgatccag ccttcctcgg tgtcccagtc aggcagcgcg gaggcggcgc acgccaatgc   1800
cccgatcctc tcggccgccg cgcccgtcga catctcgtcc gcttcgtcct cggcgtccga   1860
gtcccagaac gcgtcgtgca gcgtgctctt gggtgacggg accacctcct gcttcgccgg   1920
gccgcggatg gcggcggcgg cggaggcgga ggcgacgacg aacgggtgcg ccgcgagctg   1980
cgcggccgtg ggccgggcgg cggcgcggcg ctcgaagcag ccggccagga agtccttggc   2040
```

```
ctcgggcgac agccacgcgg gcacctccgg cacgtcgtcc gtgtacccga tccggtggag    2100
cgcggcgagg aggtcgtcgc cctccacgtc gctccagggc gcgcggcccg tggccagctc    2160
gacgaccatg cacccgagcg cccagacgtc ggcggcgggg ccctgctcct ggccgcgcgc    2220
cacctcgggc gccatgaacg ccggggtgcc cccgacgggg cgcgtcgacc cgccggccgg    2280
cctcgcgcac ccgaagtcgg tcagcctggc gcgcccgtcg ccgccgatga ccacgttccg    2340
ggccttgacg tccccgtgca cgagcgaccg gccgtggagg tacgccagcc cgcgcgccac    2400
gtccccggcg taggcgccga tggcgcgctc cgcgaggcgg ccccgccgc tcctggcggc    2460
ctcgtcggcc agcgacccgc ccggcgcgaa ctccagcagg agctggtact cgccgcccgc    2520
cgcggcgcgg agccgaggc agggcacgat gtgcggcgac gagaggcccc ggaggacgcg    2580
gccctcgcgc tgcagctgcg ccgcggcccc ggcggcgcgc gccgacttga ccgccaccag    2640
ctcgcccgag gcctcgtcgg aggccagcca caccacggcg cccgacgcgc cgcggccgag    2700
cgtgcgcacg cgccggagct gcttcgccgt ggtcgtcgtc gtcattggtt ctgcttctgc    2760
ttgcggctcc cgatgtggag tggaagaggc ccgatggatg cgagttgtga gggcgtgtgg    2820
tgtgcttgcg tgcgtctggc actgtggtgg cgaggggagg ccgggagggg aaggtctatt    2880
tctacgggca gcgcggggc gtggaacacg tgcggaaacc gaggggtggc ggagggaaat    2940
agccgcgtgc gtaagcgttt gcttctgtgc gcgcggcgcg gcagcctctg agcgaaagcc    3000
acgtcgcccg cataccagca gcgcccgtgc ctgagaagga aggtgtaacg aacttgtagg    3060
agcggctctg gtcgtggggt ttcgctctgt ttccggcgtt tcttcctgct gccttttact    3120
acctgcggct gcgacgacgg gttcagaccg tcggtcgcgg tctctcgcag ccgggcaggt    3180
gcatcctctc aacacttgtg cgccggccgc cgggtctgat tggtaaccac gtgcagagcc    3240
ggctgctggg tagttgccct gccctcctc cctcgcagcc gcatgtgacc actgaccagt    3300
actactacta gttccgttgc ccctcttccc tcactgctcc agcggatatg gcctggatct    3360
gatctggaag gagtgaggga ctgatgaacc ggtggtccgt cgcgttacgc actctctttt    3420
cttcaatcgt gcgtgcgtac tgtgtatacc ttcttcacgg gcaatctcac ggcgcgccgc    3480
tccatcatcc cagttcctct cgcgacgtgg atgcctcccg gaagagagcc tgccgtgggg    3540
gcaaggcaag gcgatcgagc ccccagggcg cggcgtctca ggcacagcac gctttttttg    3600
ttcggcagac ggcacggcag gcgcgagtgc gaggtgtcga cctacgctga ccccggccag    3660
cagattcccg ccgtttatag aggatgaaaa aaagatcttt cgtcttccat gtgctccggc    3720
gtgcggtttt ggctaaatga tggttacgca gttttgtttg ttcgtggtac gacacccaac    3780
ggcgtgtgga cgggggcttc caccacgctc cccgacggcc gcctcgcctt gttttactcg    3840
ggctccacca acgcctccgt ccaggtgcag tgcctggccg tgcccgccta cgacgccgat    3900
ctgcttctca ccaactggac caagttcgag ggcatcccgg tgctgttccc gccccggtc    3960
atcgggccct ttgacttccg cgactccatc acggtctgga tcgtcccctt ggacggcgc    4019
```

<210> SEQ ID NO 7
<211> LENGTH: 1662
<212> TYPE: DNA
<213> ORGANISM: Zea mays
<220> FEATURE:
<221> NAME/KEY: CDS
<222> LOCATION: (1)...(1101)

<400> SEQUENCE: 7

```
cca cca tgg agc cag cag tat caa gaa gtt gct ctt cta ttt cat gtt       48
Pro Pro Trp Ser Gln Gln Tyr Gln Glu Val Ala Leu Leu Phe His Val
1               5                   10                  15
```

| | | |
|---|---|---|
| gga act aca aaa tcg cat cca cct ata cct gaa cat cta tcg cca gaa<br>Gly Thr Thr Lys Ser His Pro Pro Ile Pro Glu His Leu Ser Pro Glu<br>20 25 30 | | 96 |
| gcc aaa gat ttt ctg cta aag tgc ctg cag aag gaa cca gag ctg agg<br>Ala Lys Asp Phe Leu Leu Lys Cys Leu Gln Lys Glu Pro Glu Leu Arg<br>35 40 45 | | 144 |
| tct act gca cca gac tta tta aag cat cct ttt gtc act gga gaa ttg<br>Ser Thr Ala Pro Asp Leu Leu Lys His Pro Phe Val Thr Gly Glu Leu<br>50 55 60 | | 192 |
| gat gac ctg cag cca ctc aat cat gct gca cgc aag aac tct ttt aat<br>Asp Asp Leu Gln Pro Leu Asn His Ala Ala Arg Lys Asn Ser Phe Asn<br>65 70 75 80 | | 240 |
| gag att cct tca gat gat atg cca aat ggc ttg ggt ttg aat aag tct<br>Glu Ile Pro Ser Asp Asp Met Pro Asn Gly Leu Gly Leu Asn Lys Ser<br>85 90 95 | | 288 |
| tcc aac tgg tcc act atg aac tcc agt aaa tca tcc aaa atc aag ccc<br>Ser Asn Trp Ser Thr Met Asn Ser Ser Lys Ser Ser Lys Ile Lys Pro<br>100 105 110 | | 336 |
| tta tgg gag ggt ggc tgt gat gat gat gac atg tgt gag ttt gct gac<br>Leu Trp Glu Gly Gly Cys Asp Asp Asp Asp Met Cys Glu Phe Ala Asp<br>115 120 125 | | 384 |
| aag gat gac tat gca gga gtt gga tct agc tat aat cct atg tca gaa<br>Lys Asp Asp Tyr Ala Gly Val Gly Ser Ser Tyr Asn Pro Met Ser Glu<br>130 135 140 | | 432 |
| cca ttt gat aac tgg gaa aac aag ttt gac ata agc cca gag caa aat<br>Pro Phe Asp Asn Trp Glu Asn Lys Phe Asp Ile Ser Pro Glu Gln Asn<br>145 150 155 160 | | 480 |
| tct cat caa cca atg gaa ttt ggt gaa ttg gcc aaa cat gtt gaa agc<br>Ser His Gln Pro Met Glu Phe Gly Glu Leu Ala Lys His Val Glu Ser<br>165 170 175 | | 528 |
| agc ata act ggg aat gat ttt acg ttc cct gtt ggg gga agt tgt gaa<br>Ser Ile Thr Gly Asn Asp Phe Thr Phe Pro Val Gly Gly Ser Cys Glu<br>180 185 190 | | 576 |
| gat gat gat gta ctt aca gag tca aaa ata aag gca ttt ctt gag gag<br>Asp Asp Asp Val Leu Thr Glu Ser Lys Ile Lys Ala Phe Leu Glu Glu<br>195 200 205 | | 624 |
| aag gct ctt gac ctg aaa aag cta caa aca cct ttg tat gag gag ttc<br>Lys Ala Leu Asp Leu Lys Lys Leu Gln Thr Pro Leu Tyr Glu Glu Phe<br>210 215 220 | | 672 |
| tac aac act gtg cat gga ggg agt ttt cag gga gct gat caa act tcc<br>Tyr Asn Thr Val His Gly Gly Ser Phe Gln Gly Ala Asp Gln Thr Ser<br>225 230 235 240 | | 720 |
| aag gga aaa ctc cca att agt cca aaa ttt ccc cct cga gga aag tcg<br>Lys Gly Lys Leu Pro Ile Ser Pro Lys Phe Pro Pro Arg Gly Lys Ser<br>245 250 255 | | 768 |
| cct cca tgc aag aca cgt gta ggt gca tgt gat act tcg aat gac aca<br>Pro Pro Cys Lys Thr Arg Val Gly Ala Cys Asp Thr Ser Asn Asp Thr<br>260 265 270 | | 816 |
| gct cct gaa agc tgc agc aag caa ttt cca aga agc agt gtg gtg gat<br>Ala Pro Glu Ser Cys Ser Lys Gln Phe Pro Arg Ser Ser Val Val Asp<br>275 280 285 | | 864 |
| agc agc cga att ttg aga gaa att gct tct cct caa ctg aat gag ttt<br>Ser Ser Arg Ile Leu Arg Glu Ile Ala Ser Pro Gln Leu Asn Glu Phe<br>290 295 300 | | 912 |
| gcg gat aaa atc cat ctt gat gcc caa gat agc cca agc atc agc ttc<br>Ala Asp Lys Ile His Leu Asp Ala Gln Asp Ser Pro Ser Ile Ser Phe<br>305 310 315 320 | | 960 |
| acc gaa agg cag agg aag tgg aaa gaa gag ttg gac cag gaa ctt gag<br>Thr Glu Arg Gln Arg Lys Trp Lys Glu Glu Leu Asp Gln Glu Leu Glu<br>325 330 335 | | 1008 |

```
agg gag aga gtg ctg aga tta gct ggc tgt ggt aaa gca cca tcc cca     1056
Arg Glu Arg Val Leu Arg Leu Ala Gly Cys Gly Lys Ala Pro Ser Pro
            340                 345                 350 aac aga ggt tcc aac gtg aaa aag gag tat cat gct gac cat tga         1101
Asn Arg Gly Ser Asn Val Lys Lys Glu Tyr His Ala Asp His  *
            355                 360                 365 acaaacagca gcgttcatcg tctctttatt tcatcccaca gaacacaact ggatagtaac   1161
tacacaatgc cacagactgg cagcaacatg agtacagcct gcagcgcctt accgttcgcg   1221
gtattggcca agctatgact gcagatccat ctcgtacaag tggcagattt acgttgaagt   1281
ggactggtac atacaggggc actcgtcgcg aatatcagga tcattgtcgc tgctaccccg   1341
gaggacggcg tgctgacagt ttcctgattt taaggccgcg tttgtcattc tttttgatgc   1401
agtgctatac atgcgacttc ggttatattt ggtttctatt gagaaaaaaa tagtgttgta   1461
aaaattttgt gtttgtaagc gagcttggcg tggggtttgg ttttgtatgg agcttgtttg   1521
tgaaagcgtg taataagata gctatgcaaa ttacaggtca ttctgctggc tggatgaatc   1581
tgagcttttc ggaagctaca actgatcttc tgctgttaat agttgcaatc aaattgtgaa   1641
ccaaaaaaaa aaaaaaaaaa a                                             1662
```

<210> SEQ ID NO 8
<211> LENGTH: 366
<212> TYPE: PRT
<213> ORGANISM: Zea mays

<400> SEQUENCE: 8

```
Pro Pro Trp Ser Gln Gln Tyr Gln Glu Val Ala Leu Leu Phe His Val
 1               5                  10                  15

Gly Thr Thr Lys Ser His Pro Pro Ile Pro Glu His Leu Ser Pro Glu
            20                  25                  30

Ala Lys Asp Phe Leu Leu Lys Cys Leu Gln Lys Glu Pro Glu Leu Arg
        35                  40                  45

Ser Thr Ala Pro Asp Leu Leu Lys His Pro Phe Val Thr Gly Glu Leu
    50                  55                  60

Asp Asp Leu Gln Pro Leu Asn His Ala Ala Arg Lys Asn Ser Phe Asn
65                  70                  75                  80

Glu Ile Pro Ser Asp Asp Met Pro Asn Gly Leu Gly Leu Asn Lys Ser
                85                  90                  95

Ser Asn Trp Ser Thr Met Asn Ser Ser Lys Ser Lys Ile Lys Pro
            100                 105                 110

Leu Trp Glu Gly Gly Cys Asp Asp Asp Met Cys Glu Phe Ala Asp
        115                 120                 125

Lys Asp Asp Tyr Ala Gly Val Gly Ser Ser Tyr Asn Pro Met Ser Glu
    130                 135                 140

Pro Phe Asp Asn Trp Glu Asn Lys Phe Asp Ile Ser Pro Glu Gln Asn
145                 150                 155                 160

Ser His Gln Pro Met Glu Phe Gly Glu Leu Ala Lys His Val Glu Ser
                165                 170                 175

Ser Ile Thr Gly Asn Asp Phe Thr Phe Pro Val Gly Gly Ser Cys Glu
            180                 185                 190

Asp Asp Asp Val Leu Thr Glu Ser Lys Ile Lys Ala Phe Leu Glu Glu
        195                 200                 205

Lys Ala Leu Asp Leu Lys Lys Leu Gln Thr Pro Leu Tyr Glu Glu Phe
    210                 215                 220

Tyr Asn Thr Val His Gly Gly Ser Phe Gln Gly Ala Asp Gln Thr Ser
```

```
                 225                 230                 235                 240
Lys Gly Lys Leu Pro Ile Ser Pro Lys Phe Pro Arg Gly Lys Ser
                245                 250                 255

Pro Pro Cys Lys Thr Arg Val Gly Ala Cys Asp Thr Ser Asn Asp Thr
            260                 265                 270

Ala Pro Glu Ser Cys Ser Lys Gln Phe Pro Arg Ser Ser Val Val Asp
        275                 280                 285

Ser Ser Arg Ile Leu Arg Glu Ile Ala Ser Pro Gln Leu Asn Glu Phe
    290                 295                 300

Ala Asp Lys Ile His Leu Asp Ala Gln Asp Ser Pro Ser Ile Ser Phe
305                 310                 315                 320

Thr Glu Arg Gln Arg Lys Trp Lys Glu Glu Leu Asp Gln Glu Leu Glu
                325                 330                 335

Arg Glu Arg Val Leu Arg Leu Ala Gly Cys Gly Lys Ala Pro Ser Pro
            340                 345                 350

Asn Arg Gly Ser Asn Val Lys Lys Glu Tyr His Ala Asp His
        355                 360                 365

<210> SEQ ID NO 9
<211> LENGTH: 1375
<212> TYPE: DNA
<213> ORGANISM: Zea mays
<220> FEATURE:
<221> NAME/KEY: CDS
<222> LOCATION: (70)...(1248)

<400> SEQUENCE: 9
atcggccaaa gcgagccaag tgattcaaac agacgagccc cgagagaaga ggagataaag        60 cagagcgcc atg gca aca gcg gtc agc ggc agg tgg acg cgc gtc cgc acg       111
           Met Ala Thr Ala Val Ser Gly Arg Trp Thr Arg Val Arg Thr
             1               5                  10 ctc ggc cgc ggc gcg tcg ggc gcg gtg gtg tcg ctc gcc gcc gac gcc        159
Leu Gly Arg Gly Ala Ser Gly Ala Val Val Ser Leu Ala Ala Asp Ala
 15                  20                  25                  30 gcc tcg ggc gcg ctc ttc gcg gtc aag tcc gcc ccc gcg ggg acg cgg        207
Ala Ser Gly Ala Leu Phe Ala Val Lys Ser Ala Pro Ala Gly Thr Arg
                 35                  40                  45 gcc gcg gag aac ctg cgg cgc gag ggg agc atc ctg tcc gcc ctc cgg        255
Ala Ala Glu Asn Leu Arg Arg Glu Gly Ser Ile Leu Ser Ala Leu Arg
             50                  55                  60 tcc ccg cac gtg gtc ccc tgc ctc ggc cac cgc ccc gcg gcc gac ggc        303
Ser Pro His Val Val Pro Cys Leu Gly His Arg Pro Ala Ala Asp Gly
         65                  70                  75 ggg tgc cag ctg ctc ctc gag ttc gcg ccc gga ggc tcg ctc gcg gac        351
Gly Cys Gln Leu Leu Leu Glu Phe Ala Pro Gly Gly Ser Leu Ala Asp
 80                  85                  90 gtg gcg gcg agg agc agc ggc ggg cgc atc ggc gac gag cgc gcc gtc        399
Val Ala Ala Arg Ser Ser Gly Gly Arg Ile Gly Asp Glu Arg Ala Val
 95                 100                 105                 110 gcc gcg tac gca gcg gac gtg gcg cgg ggc ctg gcg tac ctc cac ggg        447
Ala Ala Tyr Ala Ala Asp Val Ala Arg Gly Leu Ala Tyr Leu His Gly
                115                 120                 125 cgc tcg gtc gtg cac ggc gac gtc aag gcg cgg aac gtc gtg gtg ggc        495
Arg Ser Val Val His Gly Asp Val Lys Ala Arg Asn Val Val Val Gly
            130                 135                 140 gcc gac ggc cgc gcc aag ctc gcc gac ttc ggc tgc gcc agg gcc gtg        543
Ala Asp Gly Arg Ala Lys Leu Ala Asp Phe Gly Cys Ala Arg Ala Val
        145                 150                 155 ggc tcc ggg cgc ccc gtc ggc ggc acg ccg gcg ttc atg gcg ccc gag        591
```

```
Gly Ser Gly Arg Pro Val Gly Thr Pro Ala Phe Met Ala Pro Glu
    160                 165                 170 gtg gcg cgc ggg gag gag cag ggc ccc gcc gcc gac gtc tgg gcg ctg      639
Val Ala Arg Gly Glu Glu Gln Gly Pro Ala Ala Asp Val Trp Ala Leu
175             180                 185                 190 ggc tgc acc gtc gtc gag atg gcc acg ggc cgc gcg ccg tgg agc gac      687
Gly Cys Thr Val Val Glu Met Ala Thr Gly Arg Ala Pro Trp Ser Asp
                195                 200                 205 gtg gac agc ctc ccc gcg gca gtg cac cgg atc ggg tac acc gac gcc      735
Val Asp Ser Leu Pro Ala Ala Val His Arg Ile Gly Tyr Thr Asp Ala
            210                 215                 220 gtg ccg gac gcg ccc ggg tgg atg tcc gcc gag gcc aag gac ttc ctg      783
Val Pro Asp Ala Pro Gly Trp Met Ser Ala Glu Ala Lys Asp Phe Leu
        225                 230                 235 gcc cgg tgc ttc gcc agg aac ccg cgc gac cgg tgc acg gcg gcg cag      831
Ala Arg Cys Phe Ala Arg Asn Pro Arg Asp Arg Cys Thr Ala Ala Gln
    240                 245                 250 ctc ctg gag cac ccg ttc ctg gcg tca gcc ggc cgc ggc gtc aag gcg      879
Leu Leu Glu His Pro Phe Leu Ala Ser Ala Gly Arg Gly Val Lys Ala
255                 260                 265                 270 gag gag gct gcg gcg gcg tct ccc acg agc acg ctg gac gcc gcg gtc      927
Glu Glu Ala Ala Ala Ala Ser Pro Thr Ser Thr Leu Asp Ala Ala Val
                275                 280                 285 tgg gag ccc gac tcc gat gac gag ggc gat gcg tca gag agc ccc gcc      975
Trp Glu Pro Asp Ser Asp Asp Glu Gly Asp Ala Ser Glu Ser Pro Ala
            290                 295                 300 cag aga atc aag gca ctg gcc tgc ccc tgc tcg gtc ctg ccg gac tgg     1023
Gln Arg Ile Lys Ala Leu Ala Cys Pro Cys Ser Val Leu Pro Asp Trp
        305                 310                 315 gat tcc gaa gag ggc gac tgg att gaa gtg ctc gac gag caa tgt gaa     1071
Asp Ser Glu Glu Gly Asp Trp Ile Glu Val Leu Asp Glu Gln Cys Glu
    320                 325                 330 gcc acc aac ttg gtg ccg gta cca acc aaa gag gcg gcc ggc gat gac     1119
Ala Thr Asn Leu Val Pro Val Pro Thr Lys Glu Ala Ala Gly Asp Asp
335                 340                 345                 350 gag tgc cag ctc ccg agt gtg gcg ttg gaa aca ggg gtc gac ttc atc     1167
Glu Cys Gln Leu Pro Ser Val Ala Leu Glu Thr Gly Val Asp Phe Ile
                355                 360                 365 gac gcc gat gcg gag ggc gaa gat ccc ggg tgt tgt gta gct gta gga     1215
Asp Ala Asp Ala Glu Gly Glu Asp Pro Gly Cys Cys Val Ala Val Gly
            370                 375                 380 tat gat ccc ggg tgt tgt gta gcc gta gaa taa actactgctt tgtcagttgg   1268
Tyr Asp Pro Gly Cys Cys Val Ala Val Glu  *
        385                 390 gctgttggaa gagcagtgta tgggtaatta cagtaaccca actgtatttc tcgcttacag   1328
tattgaaata tcaagacct ctttactgca aaaaaaaaaa aaaaaaa                  1375

<210> SEQ ID NO 10
<211> LENGTH: 392
<212> TYPE: PRT
<213> ORGANISM: Zea mays

<400> SEQUENCE: 10

Met Ala Thr Ala Val Ser Gly Arg Trp Thr Arg Val Arg Thr Leu Gly
1               5                   10                  15

Arg Gly Ala Ser Gly Ala Val Val Ser Leu Ala Ala Asp Ala Ala Ser
                20                  25                  30

Gly Ala Leu Phe Ala Val Lys Ser Ala Pro Ala Gly Thr Arg Ala Ala
        35                  40                  45
```

Glu Asn Leu Arg Arg Glu Gly Ser Ile Leu Ser Ala Leu Arg Ser Pro
            50                  55                  60

His Val Val Pro Cys Leu Gly His Arg Pro Ala Ala Asp Gly Gly Cys
 65                  70                  75                  80

Gln Leu Leu Leu Glu Phe Ala Pro Gly Gly Ser Leu Ala Asp Val Ala
                85                  90                  95

Ala Arg Ser Ser Gly Gly Arg Ile Gly Asp Glu Arg Ala Val Ala Ala
            100                 105                 110

Tyr Ala Ala Asp Val Ala Arg Gly Leu Ala Tyr Leu His Gly Arg Ser
            115                 120                 125

Val Val His Gly Asp Val Lys Ala Arg Asn Val Val Gly Ala Asp
            130                 135                 140

Gly Arg Ala Lys Leu Ala Asp Phe Gly Cys Ala Arg Ala Val Gly Ser
145                 150                 155                 160

Gly Arg Pro Val Gly Gly Thr Pro Ala Phe Met Ala Pro Glu Val Ala
                165                 170                 175

Arg Gly Glu Glu Gln Gly Pro Ala Ala Asp Val Trp Ala Leu Gly Cys
            180                 185                 190

Thr Val Val Glu Met Ala Thr Gly Arg Ala Pro Trp Ser Asp Val Asp
            195                 200                 205

Ser Leu Pro Ala Ala Val His Arg Ile Gly Tyr Thr Asp Ala Val Pro
            210                 215                 220

Asp Ala Pro Gly Trp Met Ser Ala Glu Ala Lys Asp Phe Leu Ala Arg
225                 230                 235                 240

Cys Phe Ala Arg Asn Pro Arg Asp Arg Cys Thr Ala Ala Gln Leu Leu
                245                 250                 255

Glu His Pro Phe Leu Ala Ser Ala Gly Arg Gly Val Lys Ala Glu Glu
            260                 265                 270

Ala Ala Ala Ala Ser Pro Thr Ser Thr Leu Asp Ala Ala Val Trp Glu
            275                 280                 285

Pro Asp Ser Asp Asp Glu Gly Asp Ala Ser Glu Ser Pro Ala Gln Arg
            290                 295                 300

Ile Lys Ala Leu Ala Cys Pro Cys Ser Val Leu Pro Asp Trp Asp Ser
305                 310                 315                 320

Glu Glu Gly Asp Trp Ile Glu Val Leu Asp Glu Gln Cys Glu Ala Thr
                325                 330                 335

Asn Leu Val Pro Val Pro Thr Lys Glu Ala Ala Gly Asp Asp Glu Cys
            340                 345                 350

Gln Leu Pro Ser Val Ala Leu Glu Thr Gly Val Asp Phe Ile Asp Ala
            355                 360                 365

Asp Ala Glu Gly Glu Asp Pro Gly Cys Cys Val Ala Val Gly Tyr Asp
            370                 375                 380

Pro Gly Cys Cys Val Ala Val Glu
385                 390

<210> SEQ ID NO 11
<211> LENGTH: 2923
<212> TYPE: DNA
<213> ORGANISM: Zea mays

<400> SEQUENCE: 11
cgctacttct aatagtccct tattgttata atagtactta tatttaatta tttattgcat    60
atattttaac aaaagataaa tagtcttttt attatttggt ttatttaata tactgaatag   120
attaaattaa aattttttagt ctattcgagt ttgttcctaa tattattttta aaaacttcga   180

```
ttatatattt taaaacccaa aaaataaaaa ctcccaatac gctggaccaa attaacctac    240
ccgaacgccc acccctgtca cacctaccca cccaaacggc ccaaacctga aaattcccca    300
cgtgatcggc gcccacacca gccacgtatt gatctagcta gcacaggccg cctcctcccc    360
accggtcaat ccacaaggct tgccgctgcg gccgcgcgag ggtccacacg ccagtctccc    420
cgttccgtcc tgttcgcccg cgtagcccac ctgcgcatgc tttccatgcc acagcccgc    480 agaggaatcg tgtacggatg gatggaaggc aacagctttg gatgtgcttc gctctcgcgc    540
ccccgtctta taaatacgcg ccctccactt gaaacaagcg gcaaaccgca ccacaaaaca    600
aatcggccaa agcgagccaa gtgattcaaa cagacgagcc ccgagagaag aggagataaa    660
gcagagcgcc atggcaacag cggtcagcgg caggtggacg cgcgtccgca cgctgggccg    720
cggcgcgtcg ggcgcggtgg tgtcgctcgc cgccgacgcc gcctctggcg cgctcttcgc    780
ggtgaagtcc gccccccgcgt gggccgcgga gcagctgcgg cgcgagggga gcatcctgtc    840
gtccctccgg tccccgcacg tggtcccctg cctcggccac cgccccgcgg ccgacggcgg    900
gtggcagctg ctcctcgagt tcgcgcccgg cggctcgctc gcggacgtgg cggcgaggag    960
cggcggcggg cgcatcggcg acgagcgcgc cgtcgcggcg tacgcagcgg acgtggcgcg   1020
gggcctggcg tacctccacg ggcggtcggt cgtgcacggc gacgtcaagg cgcggaacgt   1080
cgtggtgggc gccgacggcc gcgccaagct cgcggacttc gggtgcgcca gggcgtggg   1140 ctccgggcgc cccgtcggcg gcacgccggc gttcatggcg cccgaggtgg cgcgcgggga   1200
ggagcagggc cccgccgccg acgtctgggc gctgggctgc accgtcgtcg agatggccac   1260
gggccgcgcg ccgtggagcg acgtggacag cctccccgcg gcagtgcacc ggatcgggta   1320
caccgacgcc gtgccggacg cgcccgggtg gatgtccgcc gaggccaagg acttcctggc   1380
ccggtgcttc gccaggaacc cgcgcgaccg gtgcacggcg gcgcagctcc tggagcaccc   1440
gttcctggcg tcagccggcc gcggcgtcaa ggcggaggag gctgcggcgg cgtctcccac   1500
gagcacgctg gacgccgcgg tctgggagcc cgactccgat gacgagggcg atgcgtcaga   1560
gagccccgcc cagagaatca aggcactggc ctgcccctgc tcggtcctgc cggactggga   1620
ttccgaagag ggcgactgga ttgaagtgct cgacgagcaa tgtgaagcca ccaacttggt   1680
gccggtacca accaaagagg cggcggcga tgacgagtgc cagctcccga gtgtggcgtt   1740
ggaaacaggg gtcgacttca tcgacgccga tgcggagggc gaagatcccg ggtgttgtgt   1800
agctgtagga tatgatcccg ggtgttgtgt agccgtagga ttaactactg ctttgtcagt   1860
tgggctgttg gaagagcagt gtatgggtga ttacagtaac ccaactgtat ttctcgctta   1920
cagtattgaa atatcaaaga cctctttact gcgaaactgt cccctctttg tcctgttcta   1980
ctaccactac cgtctaccag tttcacattg tctacataga aaaagcctct acaactgcct   2040
aactggtgcg acgcgacaat tccagaaaca ttgttctaga ccgaggcggc gacggtgacg   2100
gcgaccgcga ggcgtgagct gggaatggcc gggagagcac atcccctct cctcccatgg   2160 ggggccatgg cgctaatgct aaagcagtgg acagaatgga cagatcacgc cagtagaaag   2220
gcaattggga agcatcgcaa tctggggatt cctggccact ctgtatctca tcaaccaccc   2280
tttgctttcc tttccttttc ttttcggtca gggcattggc ctctggccac tattttaca    2340 aaccgtgaaa tcctcaccca ttctcctcca gctgataacg atgagctccg gcggccttga   2400
tggtggcgtc cgagtcccga tcgatcgagc tagcgaaacg gagcactcct gctgcgtaac   2460
taccagtggg gtctctcgtc tcgtcgggga cgctggccat gagctactgg caaaattaaa   2520
atttctacta ctccgcttca tctggataag tctggacatg tgtggcgcgt ggcctgatgc   2580
```

```
gcgatgcgag tgacggccaa gtggcgcttt cttccaaaac ctggtggtgt gggcgtggtg    2640
tgctcctcat gcaaagatga aagatatata tattaaaaaa acgaagttgg cgtacacgtt    2700
tgttacatac agtaggtgct acctggcaca cgtgggaacc gattcgggac acggggagag    2760
agatcttgag actgtgcagt acagttcctc acggtttgct caccagtcac cccggcacgt    2820
gtcacggcct ctcggctcgg gaagctcagc ttctgggaag gctcttcgct ggcgttttgg    2880
gaaagaagat gaaagccgca gcttagcata gaagtagagg gat                      2923
```

<210> SEQ ID NO 12
<211> LENGTH: 21
<212> TYPE: DNA
<213> ORGANISM: Artificial Sequence
<220> FEATURE:
<223> OTHER INFORMATION: Synthesized Forward Primer for ZmNPK1b

<400> SEQUENCE: 12

```
atccatcggg cctcttccac t                                                21
```

<210> SEQ ID NO 13
<211> LENGTH: 22
<212> TYPE: DNA
<213> ORGANISM: Artificial Sequence
<220> FEATURE:
<223> OTHER INFORMATION: Synthesized Reverse Primer for ZmNPK1b

<400> SEQUENCE: 13

```
tgtccactcc agacatgcaa tg                                               22
```

<210> SEQ ID NO 14
<211> LENGTH: 404
<212> TYPE: PRT
<213> ORGANISM: Oryza sativa

<400> SEQUENCE: 14

```
Met Ala Lys Gln Leu Arg Arg Val Arg Thr Leu Gly Arg Gly Ala Ser
 1               5                  10                  15

Gly Ala Val Val Trp Leu Ala Ser Asp Asp Asp Ser Gly Glu Leu Met
                20                  25                  30

Ala Val Lys Ser Ala Ser Ala Gly Gly Ala Ala Gln Leu Arg Arg
            35                  40                  45

Glu Gly Arg Val Leu Ser Gly Leu Cys Ser Pro His Ile Val Pro Cys
        50                  55                  60

Leu Gly Ser Arg Ala Ala Ala Gly Gly Glu Tyr Gln Leu Phe Leu Glu
    65                  70                  75                  80

Phe Ala Pro Gly Gly Ser Leu Ala Asp Glu Ala Ala Arg Asn Gly Gly
                85                  90                  95

Cys Leu Pro Glu Pro Ala Ile Arg Ala Tyr Ala Ala Asp Val Ala Arg
            100                 105                 110

Gly Leu Ala Tyr Leu His Gly Asn Ser Leu Val His Gly Asp Val Lys
        115                 120                 125

Ala Arg Asn Val Val Ile Gly Ser Asp Gly Arg Ala Arg Leu Thr Asp
    130                 135                 140

Phe Gly Cys Ala Arg Val Met Asp Ser Ala Gly Pro Ile Gly Gly Thr
145                 150                 155                 160

Pro Ala Phe Met Ala Pro Glu Val Ala Arg Gly Glu Glu Gln Gly Pro
                165                 170                 175

Ala Ala Asp Val Trp Ala Leu Gly Cys Thr Ile Ile Glu Met Ala Thr
            180                 185                 190
```

-continued

```
Gly Arg Ala Pro Trp Ser Asp Met Asp Asp Ile Leu Ala Ala Val His
            195                 200                 205

Arg Ile Gly Tyr Thr Asn Ala Val Pro Glu Val Pro Gly Trp Leu Ser
        210                 215                 220

Ala Glu Ala Lys Asp Phe Leu Asp Gly Cys Phe Glu Arg Asn Ala Ser
225                 230                 235                 240

Asp Arg Ser Thr Ala Ala Gln Leu Leu Glu His Pro Phe Val Ala Ser
                245                 250                 255

Ala Ala Ala Leu Asp Arg Trp Pro Glu Pro Ala Lys Gln Glu Arg Ala
            260                 265                 270

Ser Pro Lys Ser Thr Leu His Asp Ala Phe Trp Asp Ser Asp Thr Asp
        275                 280                 285

Asp Glu Asp Asp Glu Met Pro Thr Gly Ala Ala Glu Arg Ile Gly Ala
290                 295                 300

Leu Ala Cys Ala Ala Ser Ala Leu Pro Asp Trp Asp Ser Asp Glu Gly
305                 310                 315                 320

Trp Ile Glu Val His Asp Glu Val Ser Phe Ala Ala Val Thr Pro Pro
                325                 330                 335

Ala Ser Asp Ala Asp Tyr Phe Val Trp Ala Glu Leu Ser Asp Pro Glu
            340                 345                 350

Met Glu Gln Phe Ala Val Ala Ala Asp Gly Val Asn His Val Pro Arg
        355                 360                 365

Asn Glu Ala Glu Ala Ile Glu Ser Ser Ile Arg Gln Gly Ser Tyr Leu
370                 375                 380

His Leu Met Phe Pro Ala Ile Arg Ile Gly Val Val Ser Glu Arg Gln
385                 390                 395                 400

Ser Ile Pro Phe

<210> SEQ ID NO 15
<211> LENGTH: 474
<212> TYPE: PRT
<213> ORGANISM: Oryza sativa

<400> SEQUENCE: 15

Met Ala Ile Ala Val Ser Gly Arg Trp Thr Arg Leu Arg Thr Leu Gly
1               5                   10                  15

Arg Gly Ala Ser Gly Ala Val Val Ser Leu Ala Glu Asp Gly Ala Ser
            20                  25                  30

Gly Glu Leu Phe Ala Val Lys Thr Ala Ala Ala Glu Ala Ala Met
        35                  40                  45

Leu Arg Arg Glu Arg Gly Met Met Ser Gly Leu Ser Ser Pro His Val
50                  55                  60

Val Pro Cys Ile Gly Gly Asp Gly Pro Asp Gly Ser Tyr Asn Leu
65                  70                  75                  80

Phe Leu Glu Phe Ala Pro Gly Gly Ser Leu Ala Asn Glu Val Ala Arg
                85                  90                  95

Asp Gly Gly Arg Leu Glu Glu Arg Ala Ile Arg Val Tyr Ala Ala Asp
            100                 105                 110

Val Leu Arg Gly Leu Thr Tyr Leu His Gly Met Ser Leu Val His Gly
        115                 120                 125

Asp Val Lys Ala Asp Asn Ile Val Ile Gly Val Asp Gly Leu Ala Lys
130                 135                 140

Leu Ala Asp Phe Gly Cys Ala Lys Thr Met Asp Ser Glu Arg Pro Val
145                 150                 155                 160

Ser Gly Thr Pro Ala Phe Met Ala Pro Glu Val Ala Arg Gly Glu Glu
```

```
                165                 170                 175
Gln Gly Pro Ala Ala Asp Val Trp Ala Leu Gly Cys Thr Val Ile Glu
            180                 185                 190

Met Ala Thr Gly Arg Ala Pro Trp Ser Asp Met Asp Asp Val Leu Ala
            195                 200                 205

Ala Val His Arg Ile Gly Tyr Thr Asp Ala Val Pro Glu Val Pro Val
            210                 215                 220

Trp Leu Ser Ala Glu Ala Lys Asp Phe Leu Ala Met Cys Phe Ala Arg
225                 230                 235                 240

Asn Ala Gly Asp Arg Ser Thr Ala Ala Gln Leu Leu Glu His Pro Phe
                245                 250                 255

Val Ala Phe Ala Cys His Glu Val Lys Ala Ala Gln Pro Lys Pro Arg
            260                 265                 270

Trp Val Ser Pro Lys Ser Thr Leu Asp Ala Ala Phe Trp Glu Ser Glu
            275                 280                 285

Thr Asp Asp Glu Glu Glu Val Asp Glu Ile Thr Glu Ser Leu Cys Asp
            290                 295                 300

Arg Ile Lys Ser Leu Ala Cys Pro Val Ser Ala Leu Pro Asp Trp Asp
305                 310                 315                 320

Ser Asp Glu Gly Trp Ile Asp Leu Leu Gly Glu Gln Cys Glu Ala Cys
                325                 330                 335

Asp Ser Glu Ala Ala Arg Glu Ser Ile Asp Val Ala Arg Ser Ala Pro
            340                 345                 350

Ser Lys Val Ser Ser Ala Ala Thr Val Pro Ala Ala Glu Val Val Leu
            355                 360                 365

Val Gly Gly Gly Cys Cys Pro Ser Asn Glu Ala Asp Ala Phe Asp Gln
            370                 375                 380

Ser Ile Gly Gly Asp Ile Gln Ala Ala Asp Arg Ser Ile Glu Arg Arg
385                 390                 395                 400

Asn Lys Val Cys Ala Gly Ser Asp Asn Asp Val Leu Pro Phe Arg Leu
                405                 410                 415

Arg Leu Ala Leu Leu Gly Pro Ser Arg Pro Ser Thr Ala His Ile Arg
            420                 425                 430

Lys Pro Pro Pro Asn Pro Arg Gly Arg Ser Ala Leu Thr Ala Ser Ala
            435                 440                 445

Ser Ile Ser Ser Pro Arg Arg Ala Cys Val Asp Val Lys Arg Gly Val
            450                 455                 460

Cys Val Ala Pro Arg Pro His Arg Leu Thr
465                 470

<210> SEQ ID NO 16
<211> LENGTH: 653
<212> TYPE: PRT
<213> ORGANISM: Oryza sativa

<400> SEQUENCE: 16

Met Arg Arg Asp Asp Ala Gly Gly Gly Phe Gly Asp Leu Phe Asp
1               5                   10                  15

Ser Val Arg Arg Ser Ile Ala Phe Arg Thr Ser Thr Ala Pro Glu Thr
            20                  25                  30

Pro Gly Pro Leu Gly Gly Gly Gly Ile Gly Val Arg Ile Ser Ser
            35                  40                  45

Cys Leu Arg Lys Ser Arg Gly Met Gly Leu Leu Gly Leu Ile Ser Lys
    50                  55                  60

Ser Pro Ser Pro Pro Arg Arg Leu Leu Pro Pro Ala Pro Glu Phe Ser
```

```
                65                  70                  75                  80
Gly Gly Gly Gly Gly Gly Arg Gly Gly Gly Gly Glu Ser
                    85                  90                  95

Pro Gln Ile Arg Trp Arg Lys Gly Glu Leu Ile Gly Ser Gly Ala Phe
                100                 105                 110

Gly Gln Val Tyr Leu Gly Met Asn Leu Asp Thr Gly Glu Leu Leu Ala
                115                 120                 125

Val Lys Gln Val Leu Ile Gly Ser Asn Asn Ala Thr Arg Glu Lys Ala
    130                 135                 140

Gln Ala His Ile Arg Glu Leu Glu Glu Val Lys Leu Leu Lys Asn
145                 150                 155                 160

Leu Ser His Pro Asn Ile Val Arg Tyr Leu Gly Thr Val Arg Glu Glu
                165                 170                 175

Asp Thr Leu Asn Ile Leu Leu Glu Phe Val Pro Gly Gly Ser Ile Gln
                180                 185                 190

Ser Leu Leu Gly Lys Leu Gly Ser Phe Pro Glu Ala Val Ile Arg Lys
                195                 200                 205

Tyr Thr Lys Gln Ile Leu Gln Gly Leu Glu Tyr Leu His Asn Asn Ala
    210                 215                 220

Ile Ile His Arg Asp Ile Lys Gly Ala Asn Ile Leu Val Asp Asn Lys
225                 230                 235                 240

Gly Cys Ile Lys Leu Ala Asp Phe Gly Ala Ser Lys Gln Val Ala Lys
                245                 250                 255

Leu Ala Thr Ile Thr Ala Ala Lys Thr Met Lys Gly Thr Pro His Trp
                260                 265                 270

Met Ala Pro Glu Val Ile Val Gly Ser Gly His Asn Phe Ser Ala Asp
                275                 280                 285

Ile Trp Ser Val Gly Cys Thr Val Ile Glu Met Ala Thr Gly Lys Pro
    290                 295                 300

Pro Trp Ser Gln Gln Tyr Gln Glu Val Ala Leu Leu Phe His Val Gly
305                 310                 315                 320

Thr Thr Lys Ser His Pro Pro Ile Pro Glu His Leu Ser Pro Glu Ala
                325                 330                 335

Lys Asp Phe Leu Leu Lys Cys Leu Gln Lys Glu Pro Glu Leu Arg Ser
                340                 345                 350

Thr Ala Ser Asp Leu Leu Lys His Pro Phe Val Thr Gly Glu Ser Glu
                355                 360                 365

Asn Leu Gln Pro Leu Asn Cys Ala Ala Gln Glu Thr Cys Val Asn
    370                 375                 380

Glu Leu Pro Ala His Asp Val Ser Ser Gly Leu Gly Leu Asn His Ser
385                 390                 395                 400

Val Asn Trp Pro Thr Ile Ser Ser Asn Arg Ser Ser Lys Ile Lys Pro
                405                 410                 415

Leu Trp Glu Gly Ser Cys Asp Glu Asp Met Cys Glu Phe Ala Asp
                420                 425                 430

Lys Asp Asp Cys Pro Ala Val Gly Ser Ser Tyr Asn Pro Met Ser Glu
                435                 440                 445

Pro Phe Asp Asn Trp Glu Ser Lys Phe Asp Ala Ser Pro Glu Gln Thr
                450                 455                 460

Ser His Gln Ser Met Glu Phe Gly Gly Leu Ala Lys His Ala Glu Ser
465                 470                 475                 480

Ser Met Thr Glu Asn Asp Phe Thr Phe Pro Cys Glu Gly Ser Cys Glu
                485                 490                 495
```

```
Asp Asp Asp Val Leu Thr Glu Ser Lys Ile Lys Ala Phe Leu Asp Glu
            500                 505                 510

Lys Ala Leu Asp Leu Lys Lys Leu Gln Thr Pro Leu Tyr Glu Glu Phe
        515                 520                 525

Tyr Asn Thr Val Asn Ala Gly Asn Ser Gln Val Ala Asp His Thr Ser
    530                 535                 540

Asn Gly Ile Phe Ser Asn Ser Pro Lys Leu Pro Pro Arg Gly Lys Ser
545                 550                 555                 560

Pro Thr Ser Lys Met Arg Gly Ala Ala Ala Ser Thr Cys Asp
                565                 570                 575

Asn Ser Asn Asn Thr Arg Pro Glu Ser Cys Ser Asn Gln Leu Ser Glu
            580                 585                 590

Asp Thr Val Gln Ser Ser Arg Ile Leu Arg Glu Ile Ala Ser Pro Gln
        595                 600                 605

Leu Asp Glu Leu Gly Asn Lys Ile His Ser Asp Val Gln Asp Ser Pro
    610                 615                 620

Ser Val Ser Phe Ala Glu Arg Gln Arg Lys Trp Lys Glu Glu Leu Val
625                 630                 635                 640

Gln Glu Leu Glu Arg Glu Arg Gly Asn Asp Glu Ile Ser
                645                 650

<210> SEQ ID NO 17
<211> LENGTH: 666
<212> TYPE: PRT
<213> ORGANISM: Arabidopsis thaliana

<400> SEQUENCE: 17

Met Gln Asp Phe Phe Gly Ser Val Arg Arg Ser Leu Val Phe Arg Pro
1               5                   10                  15

Ser Ser Asp Asp Asp Asn Gln Glu Asn Gln Pro Pro Phe Pro Gly Val
            20                  25                  30

Leu Ala Asp Lys Ile Thr Ser Cys Ile Arg Lys Ser Lys Ile Phe Ile
        35                  40                  45

Lys Pro Ser Phe Ser Pro Pro Pro Ala Asn Thr Val Asp Met Ala
    50                  55                  60

Pro Pro Ile Ser Trp Arg Lys Gly Gln Leu Ile Gly Arg Gly Ala Phe
65                  70                  75                  80

Gly Thr Val Tyr Met Gly Met Asn Leu Asp Ser Gly Glu Leu Leu Ala
                85                  90                  95

Val Lys Gln Val Leu Ile Ala Ala Asn Phe Ala Ser Lys Glu Lys Thr
            100                 105                 110

Gln Ala His Ile Gln Glu Leu Glu Glu Glu Val Lys Leu Leu Lys Asn
        115                 120                 125

Leu Ser His Pro Asn Ile Val Arg Tyr Leu Gly Thr Val Arg Glu Asp
    130                 135                 140

Asp Thr Leu Asn Ile Leu Leu Glu Phe Val Pro Gly Gly Ser Ile Ser
145                 150                 155                 160

Ser Leu Leu Glu Lys Phe Gly Pro Phe Pro Glu Ser Val Val Arg Thr
                165                 170                 175

Tyr Thr Arg Gln Leu Leu Leu Gly Leu Glu Tyr Leu His Asn His Ala
            180                 185                 190

Ile Met His Arg Asp Ile Lys Gly Ala Asn Ile Leu Val Asp Asn Lys
        195                 200                 205

Gly Cys Ile Lys Leu Ala Asp Phe Gly Ala Ser Lys Gln Val Ala Glu
    210                 215                 220
```

-continued

```
Leu Ala Thr Met Thr Gly Ala Lys Ser Met Lys Gly Thr Pro Tyr Trp
225                 230                 235                 240

Met Ala Pro Glu Val Ile Leu Gln Thr Gly His Ser Phe Ser Ala Asp
            245                 250                 255

Ile Trp Ser Val Gly Cys Thr Val Ile Glu Met Val Thr Gly Lys Ala
                260                 265                 270

Pro Trp Ser Gln Gln Tyr Lys Glu Val Ala Ala Ile Phe Phe Ile Gly
            275                 280                 285

Thr Thr Lys Ser His Pro Pro Ile Pro Asp Thr Leu Ser Ser Asp Ala
290                 295                 300

Lys Asp Phe Leu Leu Lys Cys Leu Gln Glu Val Pro Asn Leu Arg Pro
305                 310                 315                 320

Thr Ala Ser Glu Leu Leu Lys His Pro Phe Val Met Gly Lys His Lys
                325                 330                 335

Glu Ser Ala Ser Thr Asp Leu Gly Ser Val Leu Asn Asn Leu Ser Thr
            340                 345                 350

Pro Leu Pro Leu Gln Ile Asn Asn Thr Lys Ser Thr Pro Asp Ser Thr
        355                 360                 365

Cys Asp Asp Val Gly Asp Met Cys Asn Phe Gly Ser Leu Asn Tyr Ser
370                 375                 380

Leu Val Asp Pro Val Lys Ser Ile Gln Asn Lys Asn Leu Trp Gln Gln
385                 390                 395                 400

Asn Asp Asn Gly Gly Asp Glu Asp Met Cys Leu Ile Asp Asp Glu
            405                 410                 415

Asn Phe Leu Thr Phe Asp Gly Glu Met Ser Ser Thr Leu Glu Lys Asp
            420                 425                 430

Cys His Leu Lys Lys Ser Cys Asp Asp Ile Ser Asp Met Ser Ile Ala
        435                 440                 445

Leu Lys Ser Lys Phe Asp Glu Ser Pro Gly Asn Gly Glu Lys Glu Ser
450                 455                 460

Thr Met Ser Met Glu Cys Asp Gln Pro Ser Tyr Ser Glu Asp Asp Asp
465                 470                 475                 480

Glu Leu Thr Glu Ser Lys Ile Lys Ala Phe Leu Asp Gly Lys Ala Ala
            485                 490                 495

Asp Leu Lys Lys Leu Gln Thr Pro Leu Tyr Glu Glu Phe Tyr Asn Ser
            500                 505                 510

Leu Ile Thr Phe Ser Pro Ser Cys Met Glu Ser Asn Leu Ser Asn Ser
        515                 520                 525

Lys Arg Glu Asp Thr Ala Arg Gly Phe Leu Lys Leu Pro Pro Lys Ser
530                 535                 540

Arg Ser Pro Ser Arg Gly Pro Leu Gly Gly Ser Pro Arg Ala Thr
545                 550                 555                 560

Asp Ala Thr Ser Cys Ser Lys Ser Pro Gly Ser Gly Gly Ser Arg Glu
            565                 570                 575

Leu Asn Ile Asn Asn Gly Gly Asp Glu Ala Ser Gln Asp Gly Val Ser
            580                 585                 590

Ala Arg Val Thr Asp Trp Arg Gly Leu Val Val Asp Thr Lys Gln Glu
        595                 600                 605

Leu Ser Gln Cys Val Ala Leu Ser Glu Ile Glu Lys Lys Trp Lys Glu
610                 615                 620

Glu Leu Asp Gln Glu Leu Glu Arg Lys Arg Gln Glu Ile Met Arg Gln
625                 630                 635                 640

Ala Gly Leu Gly Ser Ser Pro Arg Asp Arg Gly Met Ser Arg Gln Arg
            645                 650                 655
```

Glu Lys Ser Arg Phe Ala Ser Pro Gly Lys
            660             665

<210> SEQ ID NO 18
<211> LENGTH: 615
<212> TYPE: DNA
<213> ORGANISM: Zea mays
<220> FEATURE:
<221> NAME/KEY: promoter
<222> LOCATION: (1)...(615)
<223> OTHER INFORMATION: rab17 promoter

<400> SEQUENCE: 18

```
ctatagtatt ttaaaattgc attaacaaac atgtcctaat tggtactcct gagatactat      60
accctcctgt tttaaaatag ttggcattat cgaattatca ttttactttt taatgttttc     120
tcttctttta atatatttta tgaattttaa tgtattttaa aatgttatgc agttcgctct     180
ggacttttct gctgcgccta cacttgggtg tactgggcct aaattcagcc tgaccgaccg     240
cctgcattga ataatggatg agcaccggta aaatccgcgt acccaacttt cgagaagaac     300
cgagacgtgg cgggccgggc caccgacgca cggcaccagc gactgcacac gtcccgccgg     360
cgtacgtgta cgtgctgttc cctcactggc cgcccaatcc actcatgcat gcccacgtac     420
acccctgccg tggcgcgccc agatcctaat cctttcgccg ttctgcactt ctgctgccta     480
taaatggcgg catcgaccgt cacctgcttc accaccggcg agccacatcg agaacacgat     540
cgagcacaca agcacgaaga ctcgtttagg agaaaccaca aaccaccaag ccgtgcaagc     600
accatggacg ccgcc                                                     615
```

<210> SEQ ID NO 19
<211> LENGTH: 1625
<212> TYPE: DNA
<213> ORGANISM: Arabidopsis thaliana
<220> FEATURE:
<221> NAME/KEY: promoter
<222> LOCATION: (1)...(1625)
<223> OTHER INFORMATION: rd29a promoter

<400> SEQUENCE: 19

```
agcttggttg ctatggtagg gactatgggg ttttcggatt ccggtggaag tgagtgggga      60
ggcagtggcg gaggtaaggg agttcaagat tctggaactg aagatttggg gttttgcttt     120
tgaatgtttg cgttttttgta tgatgcctct gtttgtgaac tttgatgtat tttatctttg     180
tgtgaaaaag agattgggtt aataaaatat ttgcttttt ggataagaaa ctcttttagc     240
ggcccattaa taaaggttac aaatgcaaaa tcatgttagc gtcagatatt taattattcg     300
aagatgattg tgatagattt aaaattatcc tagtcaaaaa gaaagagtag gttgagcaga     360
aacagtgaca tctgttgttt gtaccataca aattagttta gattattggt taacatgtta     420
aatggctatg catgtgacat ttagacctta tcggaattaa tttgtagaat tattaattaa     480
gatgttgatt agttcaaaca aaaattttat attaaaaaat gtaaacgaat attttgtatg     540
ttcagtgaaa gtaaacaaa ttaaattaac aagaaactta tagaagaaaa ttttttactat     600
ttaagagaaa gaaaaaaatc tatcatttaa tctgagtcct aaaaactgtt atacttaaca     660
gttaacgcat gatttgatgg aggagccata gatgcaattc aatcaaactg aaatttctgc     720
aagaatctca aacacggaga tctcaaagtt tgaagaaaa tttatttctt cgactcaaaa     780
caaacttacg aaatttaggt agaacttata tacattatat gtaatttttt tgtaacaaaa     840
tgttttttatt attattatag aattttactg gttaaattaa aaatgaatag aaaaggtgaa     900
```

```
ttaagaggag agaggaggta aacattttct tctattttt  catattttca ggataaatta      960
ttgtaaaagt ttacaagatt tccatttgac tagtgtaaat gaggaatatt ctctagtaag     1020
atcattattt catctacttc ttttatcttc taccagtaga ggaataaaca atatttagct     1080
cctttgtaaa tacaaattaa ttttccttct tgacatcatt caattttaat tttacgtata     1140
aaataaaaga tcatacctat tagaacgatt aaggagaaat acaattcgaa tgagaaggat     1200
gtgccgtttg ttataataaa cagccacacg acgtaaacgt aaaatgacca catgatgggc     1260
caatagacat ggaccgacta ctaataatag taagttacat tttaggatgg aataaatatc     1320
ataccgacat cagttttgaa agaaaaggga aaaaagaaa  aaataaataa aagatatact     1380
accgacatga gttccaaaaa gcaaaaaaaa agatcaagcc gacacagaca cgcgtagaga     1440
gcaaaatgac tttgacgtca caccacgaaa acagacgctt catacgtgtc cctttatctc     1500
tctcagtctc tctataaact tagtgagacc ctcctctgtt ttactcacaa atatgcaaac     1560
tagaaaacaa tcatcaggaa taaagggttt gattacttct attggaaaga aaaaaatctt     1620
tggac                                                                1625

<210> SEQ ID NO 20
<211> LENGTH: 811
<212> TYPE: DNA
<213> ORGANISM: Zea mays
<220> FEATURE:
<221> NAME/KEY: promoter
<222> LOCATION: (1)...(811)
<223> OTHER INFORMATION: eep5 promoter

<400> SEQUENCE: 20
ccggtagtgc tagtggctac ctcagttagg tgccaggcta taacttcgtc tagcggctac       60
ctctattcag gtgccgagtg ttttccaggc tttgccgagt gctttcgaca ctcagcaaag      120
aggttgattc cggtggtgct tccgacgact caagtcagct gttagctgta ggaaattaat      180
ctaactttcg acggctgttg ttaagacagt agaaaattaa tgtaatttac aacggctgac      240
tttgtcccca ttcaaaattg tttaggccat ggaaagtcca cgatttttcct gtatttatct     300 aatattattt gtcacctgta agagatccat gaggattacg tatttacgtt cacaaattaa      360
caaatttgct atatcacacc agggtgattt ttcattatta ttattttccg tgtgaagtat      420
ctgtccagag caaatcgaat aagtgcatgc cgccagtaga aatgtttccc gtactactca      480
ttaattaaag gtatccatcc tccatcctct ggctgatcaa gaataatttc atgaatcctc      540
actcgtgcag tttttgagtt aggattctgt tgcattaaaa acgatcatct ttgattcaga      600
tacacttgca ttctacatga attaatgatt gcatatctat cttgaccata tcttggaaaa      660
aagattatgt gcatctccag cattatatta aacccacaga agctagctat ctaccagtat      720
atatagagag aggcgctgtc acatatagaa acaaaacatt atcagtatct tccacaagca      780
cctgctatag ttgtgtggtg caaacaccaa a                                    811
```